US012595511B2

(12) United States Patent
Lo et al.

(10) Patent No.: US 12,595,511 B2
(45) Date of Patent: *Apr. 7, 2026

(54) METHODS USING CHARACTERISTICS OF URINARY AND OTHER DNA

(71) Applicants: The Chinese University of Hong Kong, Shatin (HK); GRAIL, Inc., Menlo Park, CA (US)

(72) Inventors: Yuk-Ming Dennis Lo, Hong Kong SAR (CN); Kwan Chee Chan, Hong Kong SAR (CN); Peiyong Jiang, Hong Kong SAR (CN); Suk Hang Cheng, Hong Kong SAR (CN); Ze Zhou, Hong Kong SAR (CN); Tingting Xie, Hong Kong SAR (CN); Guangya Wang, Hong Kong SAR (CN); Chen Ding, Hong Kong SAR (CN)

(73) Assignees: The Chinese University of Hong Kong, Shatin (HK); GRAIL, Inc., Menlo Park, CA (US)

( * ) Notice: Subject to any disclaimer, the term of this patent is extended or adjusted under 35 U.S.C. 154(b) by 93 days.

This patent is subject to a terminal disclaimer.

(21) Appl. No.: 17/544,354

(22) Filed: Dec. 7, 2021

(65) Prior Publication Data

US 2022/0177971 A1 Jun. 9, 2022

Related U.S. Application Data

(60) Provisional application No. 63/193,508, filed on May 26, 2021, provisional application No. 63/122,669, filed on Dec. 8, 2020.

(51) Int. Cl.
*C12Q 1/68* (2018.01)
*C12P 19/34* (2006.01)
*C12Q 1/6816* (2018.01)
*C12Q 1/6883* (2018.01)
*G16B 40/20* (2019.01)

(52) U.S. Cl.
CPC ......... *C12Q 1/6883* (2013.01); *C12Q 1/6816* (2013.01); *G16B 40/20* (2019.02); *C12Q 2600/154* (2013.01)

(58) Field of Classification Search
CPC .................. C12Q 1/688; C12Q 1/6816; C12Q 2600/154; C12Q 1/6869
See application file for complete search history.

(56) References Cited

U.S. PATENT DOCUMENTS

2020/0056245 A1 2/2020 Lo et al.

FOREIGN PATENT DOCUMENTS

WO 2016127944 A1 8/2016
WO 2018081130 A1 5/2018
WO 2018099418 A1 6/2018

OTHER PUBLICATIONS

Bone Health and Osteoporosis—A Report of the Surgeon General, "Chapter 3: Disease of Bone", (2004) U.S. Dept. of Health and Human Services, Public Health Service, Office of the Surgeon General (Year: 2004).*
Kelly M. Harkins, et al. "A novel NGS library preparation method to characterize native termini of fragmented DNA" Nucleic Acids Research, 2020, vol. 48, No. 8 (Published online Feb. 29, 2020). (Year: 2020).*
ClaretBio—Commentary "Single-Stranded Approaches for cfDNA Fragmentomics"| www.ClaretBio.com, Nov. 20, 2019. (Year: 2019).*
Jonathan C. Dudley, et al. "Detection and Surveillance of Bladder Cancer Using Urine Tumor DNA", Cancer Discov (2019) 9 (4): 500-509 (Year: 2019).*
Jiang et al., Detection and Characterization of Jagged Ends of Double-Stranded DNA in Plasma, Genome Research, vol. 30, No. 8, Aug. 14, 2020, pp. 1144-1153.
International Application No. PCT/CN2021/136087, International Search Report and Written Opinion mailed on Mar. 9, 2022, 9 pages.
Xu et al., High Levels of Circulating Cell-Free DNA are a Biomarker of Active SLE, European Journal of Clinical Investigation, vol. 48, Aug. 5, 2018, 10 pages.
Extended European Search Report dated Nov. 13, 2024 in EP Patent Application No. 21902599.6. 7 pages.

* cited by examiner

*Primary Examiner* — Stephen T Kapushoc
(74) *Attorney, Agent, or Firm* — Kilpatrick Townsend & Stockton LLP

(57) ABSTRACT

The ends of cell-free DNA fragments may be used for analysis of a biological sample. In some embodiments, DNA from a urine sample may be analyzed. Cell-free DNA fragments often include jagged ends, where one end of one strand of double-stranded DNA extends beyond the other end of the other strand. The length and amount of these jagged ends may be used to determine a level of a condition of an individual. The density of ends of fragments in certain regions may also be used in classifying the level of a condition. Additionally, DNA fragments may show a periodic pattern with the amount of DNA fragments corresponding to a length of the overhang. The periodicity may be analyzed to determine properties of a biological sample. Jagged ends may also be analyzed with a technique that avoids trimming overhanging 3' ends of a double-stranded DNA.

20 Claims, 38 Drawing Sheets

600

601 Receiving a urine sample

602 Measuring a characteristic for each nucleic acid molecule of a plurality of nucleic acid molecules 604 Determining a jagged index value using the measured characteristics of the plurality of nucleic acid molecules 606 Determining a level of a condition of an individual using the jagged index value

1100

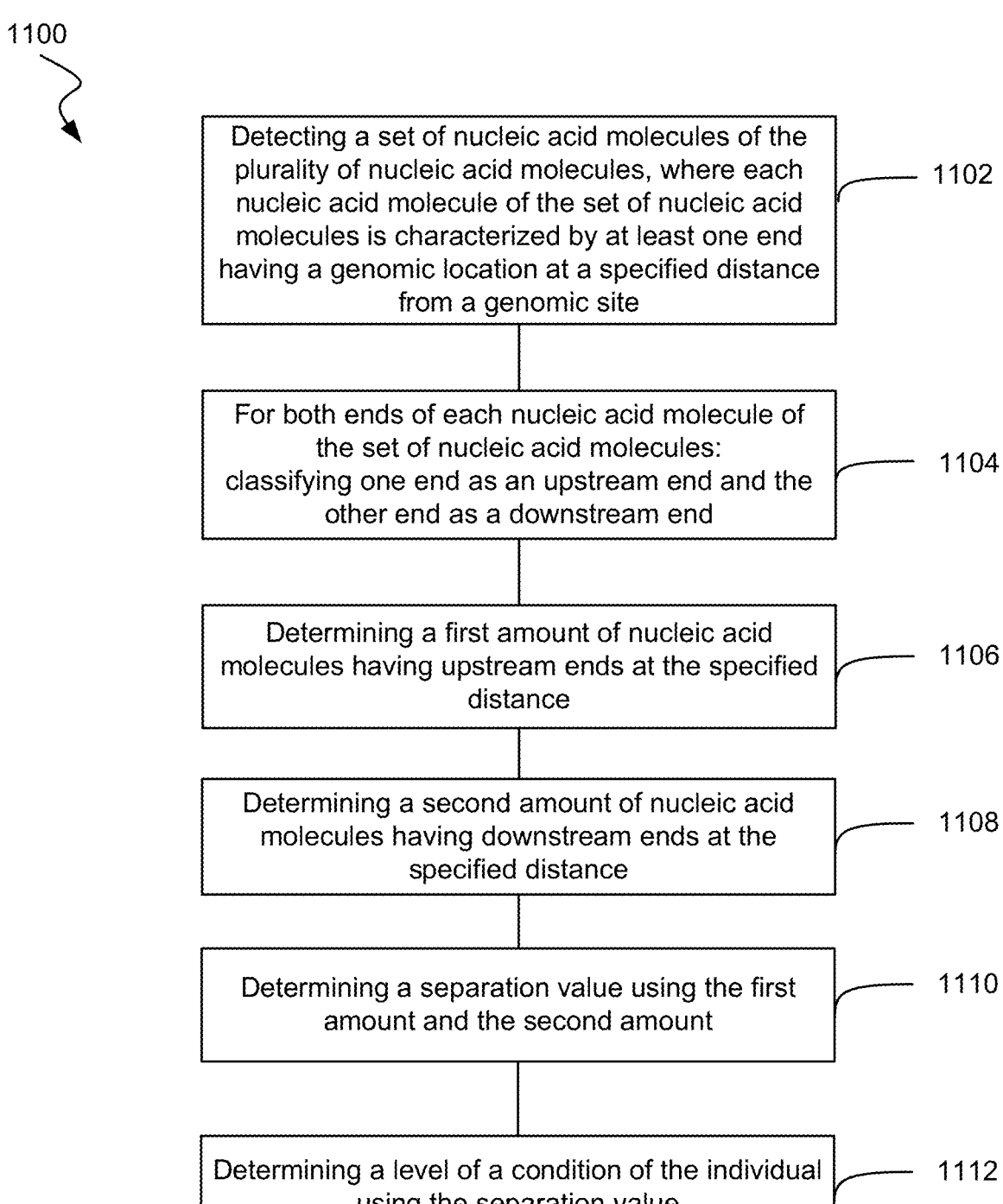

Detecting a set of nucleic acid molecules of the plurality of nucleic acid molecules, where each nucleic acid molecule of the set of nucleic acid molecules is characterized by at least one end having a genomic location at a specified distance from a genomic site    1102

For both ends of each nucleic acid molecule of the set of nucleic acid molecules: classifying one end as an upstream end and the other end as a downstream end    1104

Determining a first amount of nucleic acid molecules having upstream ends at the specified distance    1106

Determining a second amount of nucleic acid molecules having downstream ends at the specified distance    1108

Determining a separation value using the first amount and the second amount    1110

Determining a level of a condition of the individual using the separation value    1112

*FIG. 11*

1400
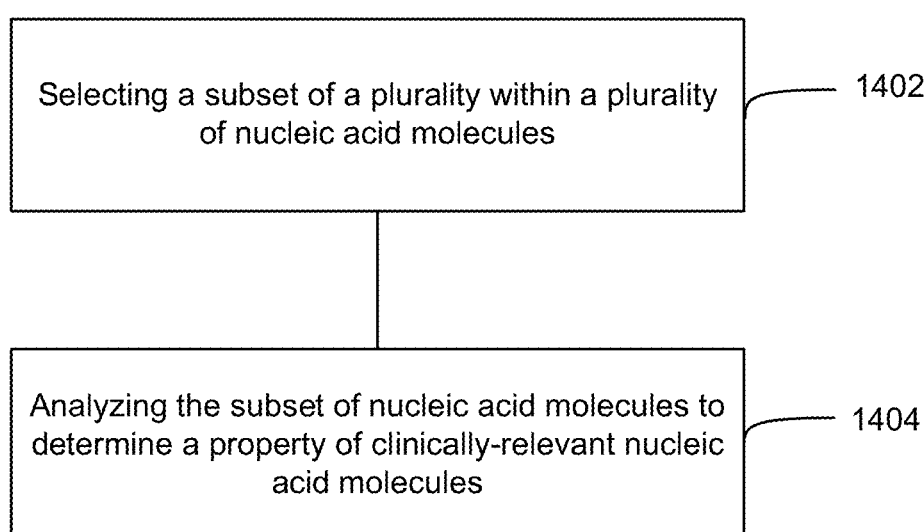
Selecting a subset of a plurality within a plurality of nucleic acid molecules ⎯⎯ 1402
Analyzing the subset of nucleic acid molecules to determine a property of clinically-relevant nucleic acid molecules ⎯⎯ 1404
*FIG. 14*

1600

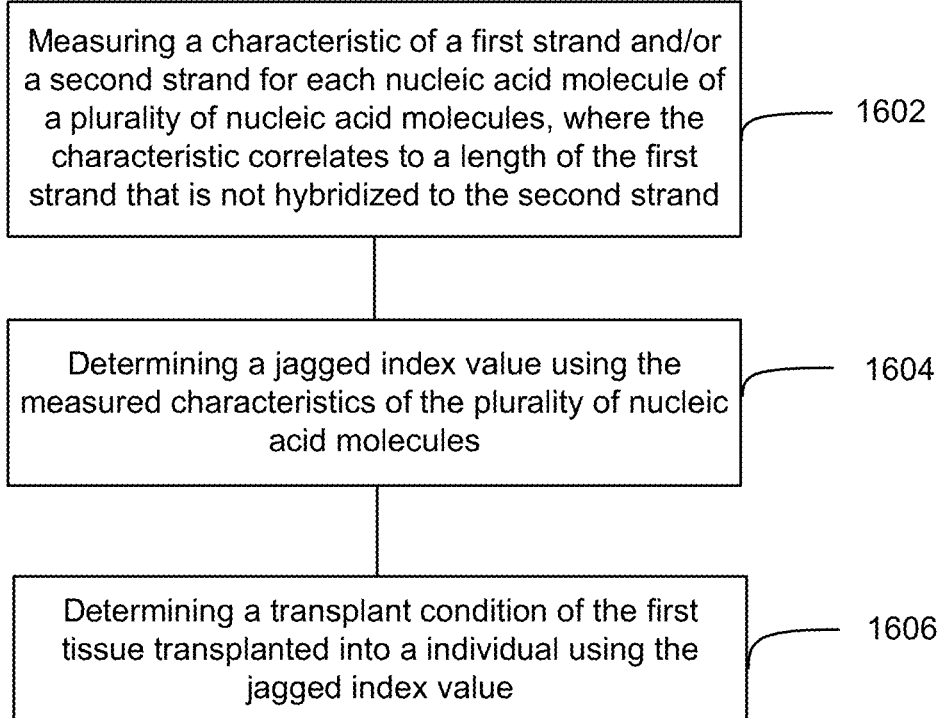

Measuring a characteristic of a first strand and/or a second strand for each nucleic acid molecule of a plurality of nucleic acid molecules, where the characteristic correlates to a length of the first strand that is not hybridized to the second strand —— 1602

Determining a jagged index value using the measured characteristics of the plurality of nucleic acid molecules —— 1604

Determining a transplant condition of the first tissue transplanted into a individual using the jagged index value —— 1606

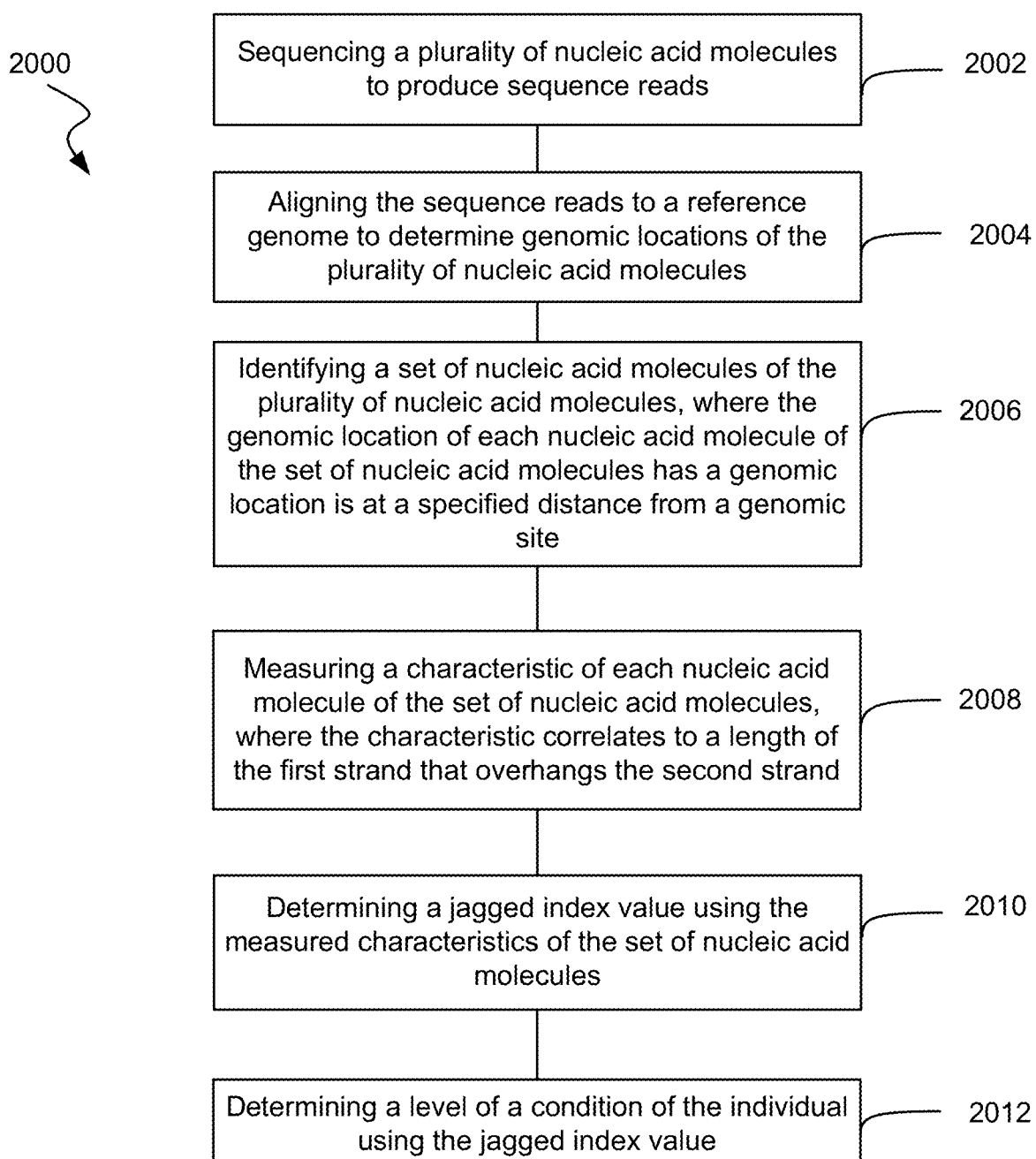

2000

Sequencing a plurality of nucleic acid molecules to produce sequence reads — 2002

Aligning the sequence reads to a reference genome to determine genomic locations of the plurality of nucleic acid molecules — 2004

Identifying a set of nucleic acid molecules of the plurality of nucleic acid molecules, where the genomic location of each nucleic acid molecule of the set of nucleic acid molecules has a genomic location is at a specified distance from a genomic site — 2006

Measuring a characteristic of each nucleic acid molecule of the set of nucleic acid molecules, where the characteristic correlates to a length of the first strand that overhangs the second strand — 2008

Determining a jagged index value using the measured characteristics of the set of nucleic acid molecules — 2010

Determining a level of a condition of the individual using the jagged index value — 2012

*FIG. 20*

1 nt 5' jagged end

5'   GGTACTCAAAGAATAGGCGACCTTTCCGAGAACCTGTCCTC   3'
3'   CCATGAGTTTCTTATCCGCTGGAAAGGCTCTTGGACAGGAGG   5'

14 nt 5' jagged end

5'   TCACATTGCTAGCCAAATTGCGCTCTTGCCCC                              3'
3'   AGTGTAACGATCGGTTTAACGCGAGAACGGGGGTGTCATACTACGA   5'

2600

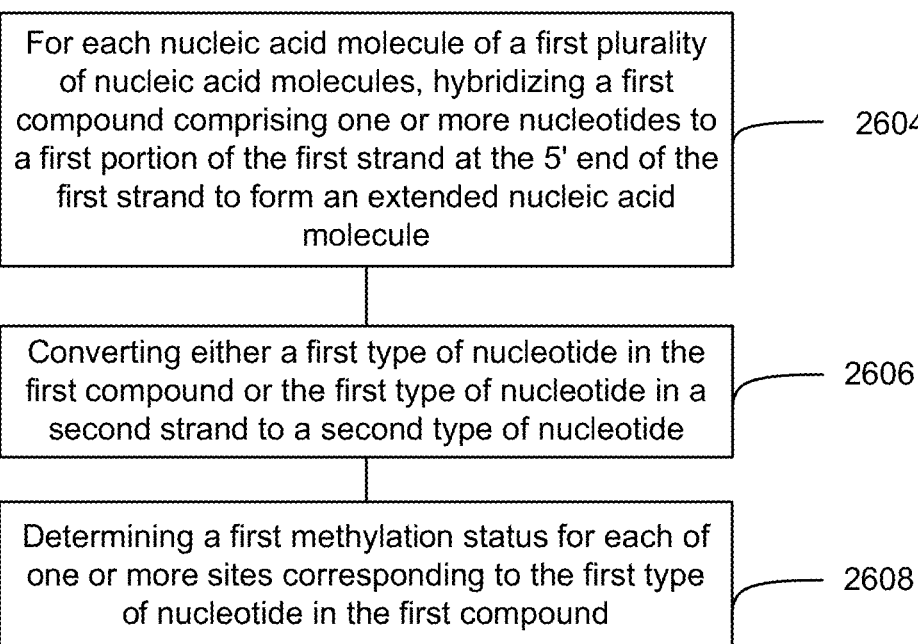

For each nucleic acid molecule of a first plurality of nucleic acid molecules, hybridizing a first compound comprising one or more nucleotides to a first portion of the first strand at the 5' end of the first strand to form an extended nucleic acid molecule — 2604

Converting either a first type of nucleotide in the first compound or the first type of nucleotide in a second strand to a second type of nucleotide — 2606

Determining a first methylation status for each of one or more sites corresponding to the first type of nucleotide in the first compound — 2608

*FIG. 26*

3300

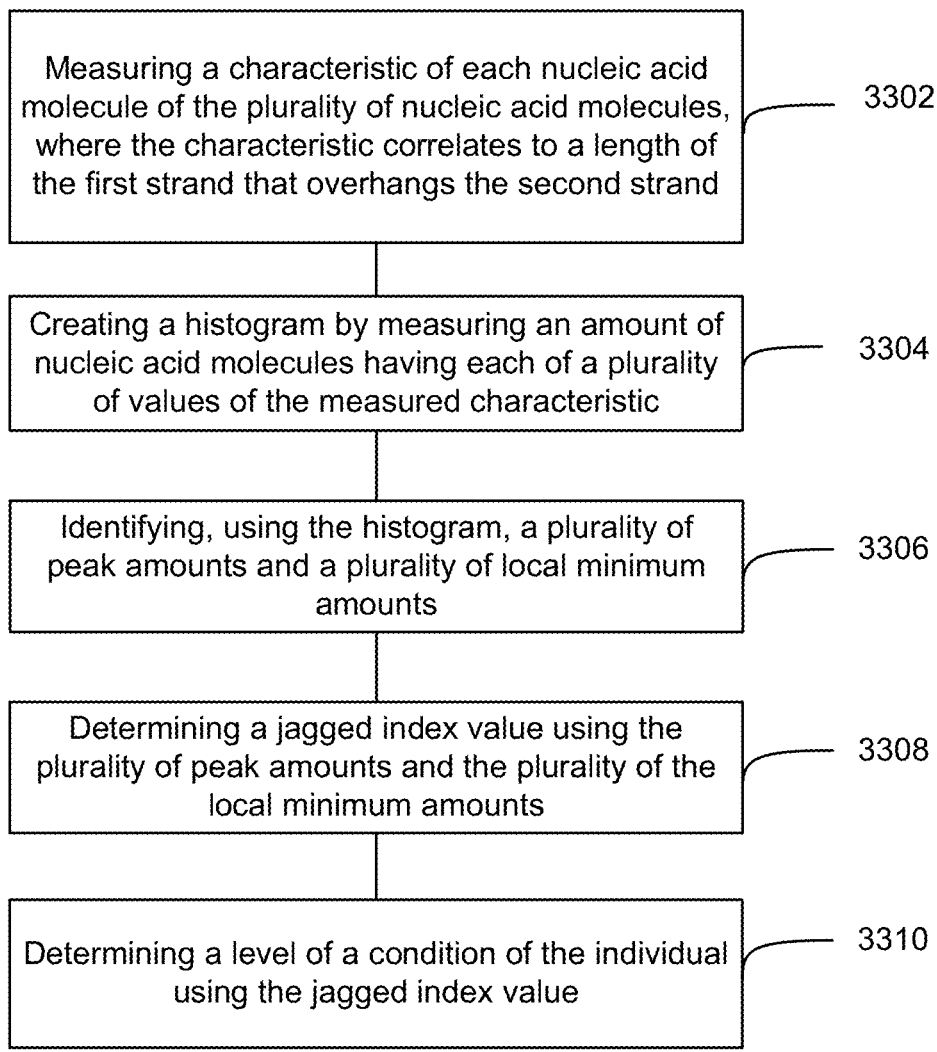

Measuring a characteristic of each nucleic acid molecule of the plurality of nucleic acid molecules, where the characteristic correlates to a length of the first strand that overhangs the second strand — 3302

Creating a histogram by measuring an amount of nucleic acid molecules having each of a plurality of values of the measured characteristic — 3304

Identifying, using the histogram, a plurality of peak amounts and a plurality of local minimum amounts — 3306

Determining a jagged index value using the plurality of peak amounts and the plurality of the local minimum amounts — 3308

Determining a level of a condition of the individual using the jagged index value — 3310

*FIG. 33*

METHODS USING CHARACTERISTICS OF URINARY AND OTHER DNA

CROSS-REFERENCES TO RELATED APPLICATIONS

This application claims priority from and is a non-provisional application of U.S. Provisional Application No. 63/193,508, entitled "METHODS USING CHARACTER-ISTICS OF URINARY AND OTHER DNA," filed on May 26, 2021, and U.S. Provisional Application No. 63/122,669, entitled "METHODS USING CHARACTERISTICS OF URINARY AND OTHER DNA," filed on Dec. 8, 2020, each of which are herein incorporated by reference in their entirety for all purposes.

BACKGROUND

Cell-free DNA has been proven to be particularly useful for molecular diagnostics and monitoring. The cell-free based applications include noninvasive prenatal testing (Chiu R K W et al. Proc Natl Acad Sci USA. 2008; 105:20458-63), cancer detection and monitoring (Chan K C A et al. Clin Chem. 2013; 59:211-24; Chan K C A et al. Proc Natl Acad Sci USA. 2013; 110:1876-8; Jiang P et al. Proc Natl Acad Sci USA. 2015; 112:E1317-25), transplantation monitoring (Zheng Y W et al. Clin Chem. 2012; 58:549-58) and tracing tissue of origin (Sun K et al. Proc Natl Acad Sci USA. 2015; 112:E5503-12; Chan K C A; Snyder M W et al. Cell. 2016; 164:57-68). Cell-free nucleic acid analysis approaches developed to date include those based on the analysis of single nucleotide variants (SNVs), copy number aberrations (CNAs), cell-free DNA ending positions in the human genome, or methylation markers. It would be beneficial to identify new nucleic acid analysis approaches for detection of new properties and to add accuracy to existing approaches.

BRIEF SUMMARY

Double-stranded cell-free DNA fragments may often have two strands that are not exactly complementary to each other. One strand may extend beyond the other strand, creating an overhang. These overhangs are often repaired to form blunt ends in analysis. However, the "jagged ends" created by these overhangs may be useful in analyzing biological samples. This document describes how jagged ends may be used in analysis and how to measure the jagged ends. As an example, jagged ends in cell-free DNA from a urine sample may be used to diagnose or detect a condition noninvasively and accurately.

The degree of jagged ends, which may be the quantity or the length of jagged ends, in a sample may reflect the level of a condition in an individual. For example, the degree of jagged ends may be related to a disease (e.g., cancer), a disorder, a pregnancy-related condition, or a transplant condition. In some embodiments, the degree of jagged ends may determine a likelihood of rejection of a transplant. In some embodiments, the jagged ends at a particular genomic location may be useful in classifying the level of a condition. For example, the jagged ends at a certain distance from a site (e.g., CTCF binding site or DNASE1 hypersensitive site [DHS]) may be used in classifying the level of a condition.

In some embodiments, the density of ends of fragments may be used in classifying the level of a condition. A fragment may have an end that is upstream and another end that is downstream, based on genomic coordinates. At certain genomic locations (e.g., at certain distances from a specific site), the number of upstream ends and the number of downstream ends may be used in classifying the level of a condition. A difference between the amounts of upstream and downstream ends may be used.

In some embodiments, jagged ends may be analyzed with an improved technique. The technique avoids trimming overhanging 3' ends of a double stranded DNA. Avoiding trimming the overhanging 3' ends unexpectedly improves analysis of 5' overhanging ends, particularly short protruding ends. With a more accurate count of short protruding ends, the analysis of jagged end lengths will be more accurate and may provide improved analysis of biological samples.

In some embodiments, DNA fragments show a periodic pattern with the amount of DNA fragments corresponding to a length of the overhang. The periodicity of amounts of DNA at different jagged end lengths can be analyzed to determine properties of a biological sample. For instance, the periodicity may be used to determine a level of a condition.

A better understanding of the nature and advantages of embodiments of the present invention may be gained with reference to the following detailed description and the accompanying drawings.

BRIEF DESCRIPTION OF THE DRAWINGS

FIG. 11 shows a method of analyzing a biological sample obtained from an individual to classify a level of a condition using end density information according to embodiment of the present invention.

FIG. 14 shows a method of enriching a biological sample by selecting DNA with certain jagged index values according to embodiments of the present invention.

FIG. 16 shows a method of analyzing a biological sample from an individual to classify a transplant condition according to embodiments of the present invention.

FIG. 20 shows a method of analyzing a biological sample obtained from an individual to classify a level of a condition using JI-U values at certain genomic locations according to embodiments of the present invention.

FIG. 26 is a method of analyzing a biological sample obtained from an individual without trimming 3' ends of fragments in the sample according to embodiments of the present invention.

FIG. 33 is a method of analyzing a biological sample using periodicity of jagged end lengths in DNA fragment according to embodiments of the present invention.

TERMS

Figure 1:
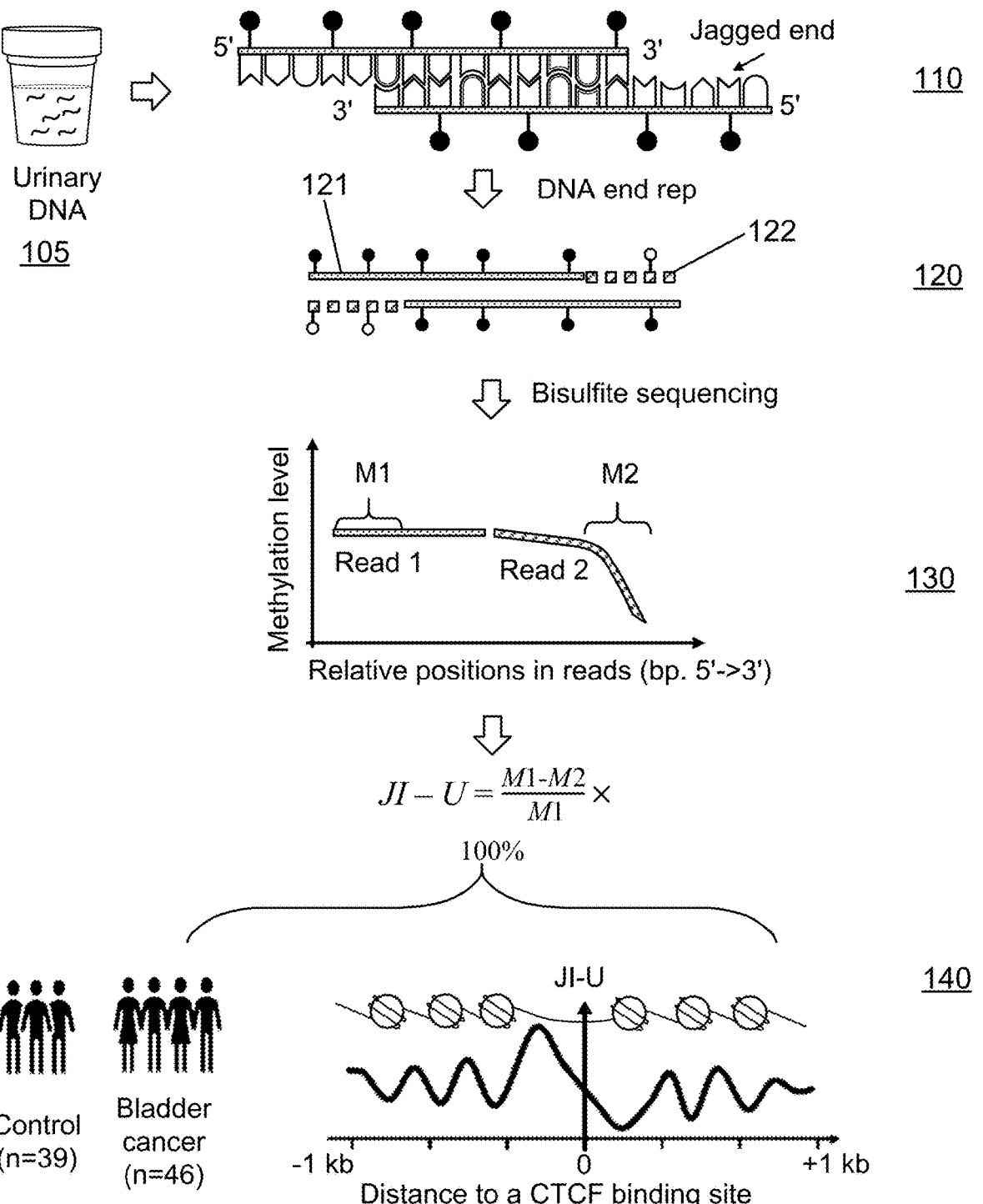
FIG. 1 shows a schematic of workflow for urinary DNA jagged end analysis according to embodiments of the present invention.

A "tissue" corresponds to a group of cells that group together as a functional unit. More than one type of cells can be found in a single tissue. Different types of tissue may consist of different types of cells (e.g., hepatocytes, alveolar cells or blood cells), but also may correspond to tissue from different organisms (mother vs. fetus) or to healthy cells vs. tumor cells. "Reference tissues" can correspond to tissues used to determine tissue-specific methylation levels. Multiple samples of a same tissue type from different individuals may be used to determine a tissue-specific methylation level for that tissue type.

An "organ" corresponds to a group of tissues with similar functions. One or more types of tissue can be found in a single organ. Organs may be a part of different organ systems, including the cardiovascular system, digestive system, endocrine system, excretory system, lymphatic system, integumentary system, muscular system, nervous system, reproductive system, respiratory system, and skeletal system.

A "biological sample" refers to any sample that is taken from a subject (e.g., a human, such as a pregnant woman, a person with cancer, or a person suspected of having cancer, an organ transplant recipient or a subject suspected of having a disease process involving an organ (e.g., the heart in myocardial infarction, or the brain in stroke, or the hematopoietic system in anemia) and contains one or more nucleic acid molecule(s) of interest. The biological sample can be a bodily fluid, such as blood, plasma, serum, urine, vaginal fluid, fluid from a hydrocele (e.g. of the testis), vaginal flushing fluids, pleural fluid, ascitic fluid, cerebrospinal fluid, saliva, sweat, tears, sputum, bronchoalveolar lavage fluid, discharge fluid from the nipple, aspiration fluid from different parts of the body (e.g. thyroid, breast), etc. Stool samples can also be used. In various embodiments, the majority of DNA in a biological sample that has been enriched for cell-free DNA (e.g., a plasma sample obtained via a centrifugation protocol) can be cell-free, e.g., greater than 50%, 60%, 70%, 80%, 90%, 95%, or 99% of the DNA can be cell-free. The centrifugation protocol can include, for example, 3,000 g×10 minutes, obtaining the fluid part, and re-centrifuging at for example, 30,000 g for another 10 minutes to remove residual cells.

A "sequence read" refers to a string of nucleotides sequenced from any part or all of a nucleic acid molecule. For example, a sequence read may be a short string of nucleotides (e.g., 20-150) sequenced from a nucleic acid fragment, a short string of nucleotides at one or both ends of a nucleic acid fragment, or the sequencing of the entire nucleic acid fragment that exists in the biological sample. A sequence read may be obtained in a variety of ways, e.g., using sequencing techniques or using probes, e.g., in hybridization arrays or capture probes, or amplification techniques, such as the polymerase chain reaction (PCR) or linear amplification using a single primer or isothermal amplification.

A "site" (also called a "genomic site") corresponds to a single site, which may be a single base position or a group of correlated base positions, e.g., a CpG site or larger group of correlated base positions. A "locus" may correspond to a region that includes multiple sites. A locus can include just one site, which would make the locus equivalent to a site in that context.

The "methylation index" or "methylation status" for each genomic site (e.g., a CpG site) can refer to the proportion of DNA fragments (e.g., as determined from sequence reads or probes) showing methylation at the site over the total number of reads covering that site. A "read" can correspond to information (e.g., methylation status at a site) obtained from a DNA fragment. A read can be obtained using reagents (e.g. primers or probes) that preferentially hybridize to DNA fragments of a particular methylation status. Typically, such reagents are applied after treatment with a process that differentially modifies or differentially recognizes DNA molecules depending of their methylation status, e.g. bisulfite conversion, or methylation-sensitive restriction enzyme, or methylation binding proteins, or anti-methylcytosine antibodies, or single molecule sequencing techniques that recognize methylcytosines and hydroxymethylcytosines.

The "methylation density" of a region can refer to the number of reads at sites within the region showing methylation divided by the total number of reads covering the sites in the region. The sites may have specific characteristics, e.g., being CpG sites. Thus, the "CpG methylation density" of a region can refer to the number of reads showing CpG methylation divided by the total number of reads covering CpG sites in the region (e.g., a particular CpG site, CpG sites within a CpG island, or a larger region). For example, the methylation density for each 100-kb bin in the human genome can be determined from the total number of cytosines not converted after bisulfite treatment (which corresponds to methylated cytosine) at CpG sites as a proportion of all CpG sites covered by sequence reads mapped to the 100-kb region. This analysis can also be performed for other bin sizes, e.g. 500 bp, 5 kb, 10 kb, 50-kb or 1-Mb, etc. A region could be the entire genome or a chromosome or part of a chromosome (e.g. a chromosomal arm). The methylation index of a CpG site is the same as the methylation density for a region when the region only includes that CpG site. The "proportion of methylated cytosines" can refer the number of cytosine sites, "C's", that are shown to be methylated (for example unconverted after bisulfite conversion) over the total number of analyzed cytosine residues, i.e. including cytosines outside of the CpG context, in the region. The methylation index, methylation density and proportion of methylated cytosines are examples of "methylation levels." Apart from bisulfite conversion, other processes known to those skilled in the art can be used to interrogate the methylation status of DNA molecules, including, but not limited to enzymes sensitive to the methylation status (e.g. methylation-sensitive restriction enzymes), methylation binding proteins, single molecule sequencing using a platform sensitive to the methylation status (e.g. nanopore sequencing (Schreiber et al. Proc Natl Acad Sci 2013; 110: 18910-18915) and by the Pacific Biosciences single molecule real time analysis (Flusberg et al. Nat Methods 2010; 7: 461-465)).

The term "sequencing depth" refers to the number of times a locus is covered by a sequence read aligned to the locus. The locus could be as small as a nucleotide, or as large as a chromosome arm, or as large as the entire genome. Sequencing depth can be expressed as 50×, 100×, etc., where "x" refers to the number of times a locus is covered by a sequence read. Sequencing depth can also be applied to multiple loci, or the whole genome, in which case x can refer to the mean number of times the loci or the haploid genome, or the whole genome, respectively, is sequenced. Ultra-deep sequencing can refer to at least 100× in sequencing depth.

A "separation value" corresponds to a difference or a ratio involving two values, e.g., two fractional contributions or two methylation levels. The separation value could be a simple difference or ratio. As examples, a direct ratio of x/y is a separation value, as well as x/(x+y). The separation value can include other factors, e.g., multiplicative factors. As other examples, a difference or ratio of functions of the values can be used, e.g., a difference or ratio of the natural logarithms (ln) of the two values. A separation value can include a difference and a ratio.

The term "classification" as used herein refers to any number(s) or other characters(s) that are associated with a particular property of a sample. For example, a "+" symbol (or the word "positive") could signify that a sample is classified as having deletions or amplifications. The classification can be binary (e.g., positive or negative) or have more levels of classification (e.g., a scale from 1 to 10 or 0 to 1). The terms "cutoff" and "threshold" refer to predetermined numbers used in an operation. For example, a cutoff size can refer to a size above which fragments are excluded. A threshold value may be a value above or below which a particular classification applies. Either of these terms can be used in either of these contexts.

The term "damage" when describing DNA molecules may refer to DNA nicks, single strands present in double-stranded DNA, overhangs of double-stranded DNA, oxidative DNA modification with oxidized guanines, abasic sites, thymidine dimers, oxidized pyrimidines, blocked 3' end, or a jagged end.

The term "jagged end" may refer to sticky ends of DNA, overhangs of DNA, or where a double-stranded DNA includes a strand of DNA not hybridized to the other strand of DNA. "Jagged end value" or "jagged index" is a measure of the extent of a jagged end. The jagged end value may be correlated (e.g., proportional) to an average length of one strand that overhangs a second strand in double-stranded DNA. The jagged end value of a plurality of DNA molecules may include consideration of blunt ends among the DNA molecules.

In some instances, the jagged index value can provide a collective measure that a strand overhangs another strand in a plurality of cell-free DNA molecules. The collective measure of jaggedness can be determined based on an estimated length of overhang in the plurality of cell-free DNA molecules, e.g., an average, median, or other collective measure of individual measurements of each of the cell-free DNA molecules. In some instances, the collective measure of jaggedness is determined for a particular fragment size range (e.g., 130-160 bps, 200-300 bps). In some instances, the collective measure of jaggedness can be determined based on the methylation signal changes proximal to the ends of the plurality of cell-free DNA molecules.

The term "alignment" and related terms may refer to matching a sequence to a reference sequence. The reference sequence may be a reference genome (e.g., human genome) or a sequence of a particular molecule. Such a reference sequence can comprise at least 100 kb, 1 Mb, 10 Mb, 50 Mb, 100 Mb, and more. Such alignment methods cannot be performed manually and are performed by specialized computer software. Alignment may involve lengthy and numerous sequences (e.g., at least 1,000, 10,000, 100,000, 1 million, 10 million, or 100 million sequences). Additionally, alignment may involve variability within the sequence itself or errors within sequence reads. Alignment with such variability or errors therefore may not require an exact match with a reference sequence.

The term "real-time" may refer to computing operations or processes that are completed within a certain time constraint. The time constraint may be 1 minute, 1 hour, 1 day, or 7 days.

DETAILED DESCRIPTION

Cell-free DNA is reported to be non-randomly fragmented (Lo et al., Sci Transl Med. 2010; 2:61ra91). Most recently, the double-stranded plasma cell-free DNA was found to carry single-stranded ends, termed jagged ends. The characteristics of plasma DNA jagged end may serve as biomarkers for noninvasive prenatal testing and cancer detection. The fragmentation patterns of plasma DNA and urinary DNA are different. For instance, the urinary DNA molecules are shorter than plasma DNA molecules (Tsui et al. PLoS One. 2012; 7:e48319). Furthermore, aspects of urinary DNA molecules for additional investigation include: (1) the extent of jagged ends in urinary DNA; (2) the use of urinary DNA jagged ends as a biomarker (e.g., for bladder cancer detection); and (3) the implementation of urinary DNA jagged ends in additional clinical contexts. Without intending to be bound by any particular theory, it is thought that the jagged ends may be related to how cell-free DNA is fragmented. For example, DNA may fragment in stages, and the size of the jagged end may reflect the stage of fragmentation. The number of jagged ends and/or the size of an overhang in a jagged end may be used to analyze a biological sample with cell-free DNA and provide information of about the sample and/or the individual from which the sample is obtained.

Different pathogenic reasons causing cell deaths in a particular organ or tissue might result in alterations in the relative presentation of DNA damages present in cell-free DNA molecules. For example, the overhangs of double-stranded DNA would bear the relationship with the tissue of origin. Therefore, embodiments of the present invention for analyzing cell-free DNA damages would offer new possibilities for detecting or monitoring, but not limited to, cancer detection, organ damages, immune diseases, and transplant status, as well as performing noninvasive prenatal testing.

Embodiments include using the degree of jagged ends, the density of jagged ends, and/or the periodicity of jagged ends to analyze a biological sample. The jagged ends may be analyzed at certain locations, which may be at a certain genomic sites or at a certain distance from certain genomic sites. The genomic sites may sites that are associate with a modification of a protein in chromatin or associated with protein interaction. These analyses of jagged ends may improve the accuracy in determining a level of a condition of an individual.

Unconventional techniques may be used to measure jagged ends in analysis of biological samples. In some embodiments, we used DNA end repair to introduce differential methylation signals between the original sequence and the jagged ends depending on whether unmethylated or methylated cytosines were used in the DNA end-repair procedure, followed by bisulfate sequencing.

In some embodiments, when overhanging 5' ends are analyzed, overhanging 3' ends may not be blunt ended. Unexpectedly, avoiding blunt ending of the 3' ends increases the amount of overhanging 5' ends available to be analyzed. As a result, analysis of biological samples may be improved.

I. Detecting Jagged Ends

Jagged ends of urinary DNA can be detected in several ways, including indirectly and directly. The urinary DNA may be intentionally methylated or unmethylated at a nucleotide. The jagged ends may be repaired using nucleotides that have an opposite methylation status as the DNA fragment without the end repair. The methylation level then gives an indication of the extent of jagged ends for the urinary DNA fragments. Synthetic probes that hybridize to certain lengths of known sequences in the fragments may be used. Additionally, jagged lengths may be directly determined by adding adaptors to the ends of double-stranded DNA, sequencing the single strands of the double-stranded DNA, and then aligning the sequences of one strand to the other strand to determine the overhang.

A. Using Methylation

FIG. 1 shows a schematic of a workflow for urinary DNA jagged end analysis. In one embodiment, 5'-protruding jagged ends of urinary DNA could be deduced on the basis of unmethylated cytosines incorporated during an end-repair process of the jagged ends. In some embodiments, the 3' end may be the protruding jagged end. Jagged ends may also be called overhangs or sticky ends.

At stage 110, DNA molecules with jagged ends may be extracted from a biological sample, including a urine sample. The urine sample may be voided from an individual. Filled lollipops represent methylated CpG sites.

At stage 120, the DNA molecules may undergo end repair. The jagged ends were filled up with nucleotides (i.e. dNTP). Unfilled lollipops represent unmethylated CpG sites. The dashed line represents newly filled-up nucleotides. The end-repaired DNA molecules were further subjected to bisulfite sequencing. The unmethylated Cs in the newly filled-up nucleotides may be converted to Uracils (Us) that are amplified by PCR as Ts, while the original methylated Cs residing within the molecules remain unmodified. Hence, the CpG cytosines in the original DNA molecule may be generally methylated, whereas the CpG cytosines incorporated by the end-repair process into the newly synthesized strand proximal to 3' termini (or 5' termini in other embodiments) of urinary DNA may be unmethylated. Thus, the repairing of the jagged ends would lower the methylation levels in regions close to 3' ends (or 5' ends in other embodiments). Bisulfite sequencing of the end repaired molecules may provide a measure of the methylation levels at both ends to provide a measure of the length of the jagged end.

In some embodiments, at least 1,000 cell-free DNA molecules are repaired. In other embodiments, at least 10,000 or 50,000 or 100,000 or 500,000 or 1,000,000 or 5,000,000 cell-free DNA molecules or more can be repaired.

At stage 130, the jaggedness of the DNA is analyzed. To quantify the jaggedness based on CpG methylation signals, we took advantage of the difference in unmethylated cytosines across CpG sites between read1 and read2 to reflect the jaggedness, referred to as Jagged Index-Unmethylated (JI-U). Read1 corresponds to the end of the top strand 121 in stage 120. Read2 corresponds to the dashed end of the top strand 122 in stage 120. JI-U was calculated by the formula below:

$$JI - U = \frac{M1 - M2}{M1} \times 100\%,$$

where $M_1$ represents the methylation density contributed by 30 bases from positions in a fragment proximal to 5' urinary DNA end, and $M_2$ represents the methylation density contributed by 30 bases from positions in a fragment proximal to 3' urinary DNA end. In some embodiments, one could use, but not limited to, 1 base, 2 bases, 3 bases, 4 bases, 5 bases, 10 bases, 20 bases, 40 bases, 50 bases, etc. proximal to 3' urinary DNA end for assessing the urinary jagged ends, as well as combinations thereof. The methylation densities $M_1$ and $M_2$ may be a statistical value (e.g., mean, median, mode, or percentile) of the methylation densities across different DNA fragments. A higher JI-U corresponds to an increased difference in methylation between read1 and read2. A higher JI-U may indicate more jagged ends for the DNA fragments.

At stage 140, the JI-U patterns are analyzed. As an example, we studied the JI-U distributions of urinary DNA between patients with bladder cancer (n=46) and without bladder cancer (control, n=39) and JI-U patterns surrounding CTCF binding sites. The JI-U is seen to vary with the distance to a CTCF binding site. The relationship between JI-U and binding sites is discussed later in this disclosure. Additionally, the JI-U is observed to depend on the type of biological sample (e.g., plasma vs. urinary). With subjects having a transplanted tissue, JI-U varies based on the type of tissue transplanted and the likelihood of rejection.

In some embodiments, the nucleotides (e.g., cytosines) of the original DNA fragment may be unmethylated. The jagged ends may be filled with nucleotides (e.g., cytosines) that are methylated. Under these conditions, a Jagged Index-Methylated (JI-M) may be used. In stage 130, read1 is unmethylated so $M_1$ is 0 or close to 0. Read2 is methylated and is non-zero or significantly above 0. Accordingly, JI-M can then be equivalent to (or proportional to) the methylation level of read2.

B. Using Probes

In some embodiments the jaggedness of the DNA may be determined without using methylation signals. For example, synthetic probes may be used. A synthetic probe may include a portion that hybridizes to a certain length of a known sequences in the fragments. A plurality of probes may be used, with complementary portions of varying lengths. The probe may include a molecular tag that identifies the length of the complementary portion and therefore the length of a jagged end hybridized to the probe. The molecular tag may be sequenced to determine the size of the jagged end.

As an example, jagged ends may be known to occur in the 24-bp common sequence of Alu. Different length probes may be designed to be complementary to at least a portion of the common sequence. For example, one probe may include a sequence complementary to 13 consecutive nucleotides of the common sequence, and another probe may include a sequence complementary to 22 consecutive nucleotides of the common sequence (with the 22 consecutive nucleotides including the 13 consecutive nucleotides). Other probe lengths from 1 to 24 nucleotides may be used. These complementary sequences may further be linked with a molecular tag. The molecular tag may be a string of a number of nucleotides (e.g., 6) that allows one to differentiate the synthetic DNA with 13-nt jagged end from the synthetic DNA with 22-nt jagged end, similar to a bar code. The hybridized DNA may be sequenced and aligned. The number of reads associated with each molecular tag may indicate the number of fragments with a certain length jagged end.

C. Alignment of Adaptors

In some embodiments, the lengths of the jagged ends may be directly determined. Directly determining the lengths of jagged end may include adding adaptors to the ends of a double-stranded DNA, forming single-stranded DNA from the double-stranded DNA, sequencing the resulting single-stranded DNA, and then aligning the sequence of one strand to the other strand. The alignment of the adaptors can be used to determine the amount of overhang in a jagged end.

Figure 2:
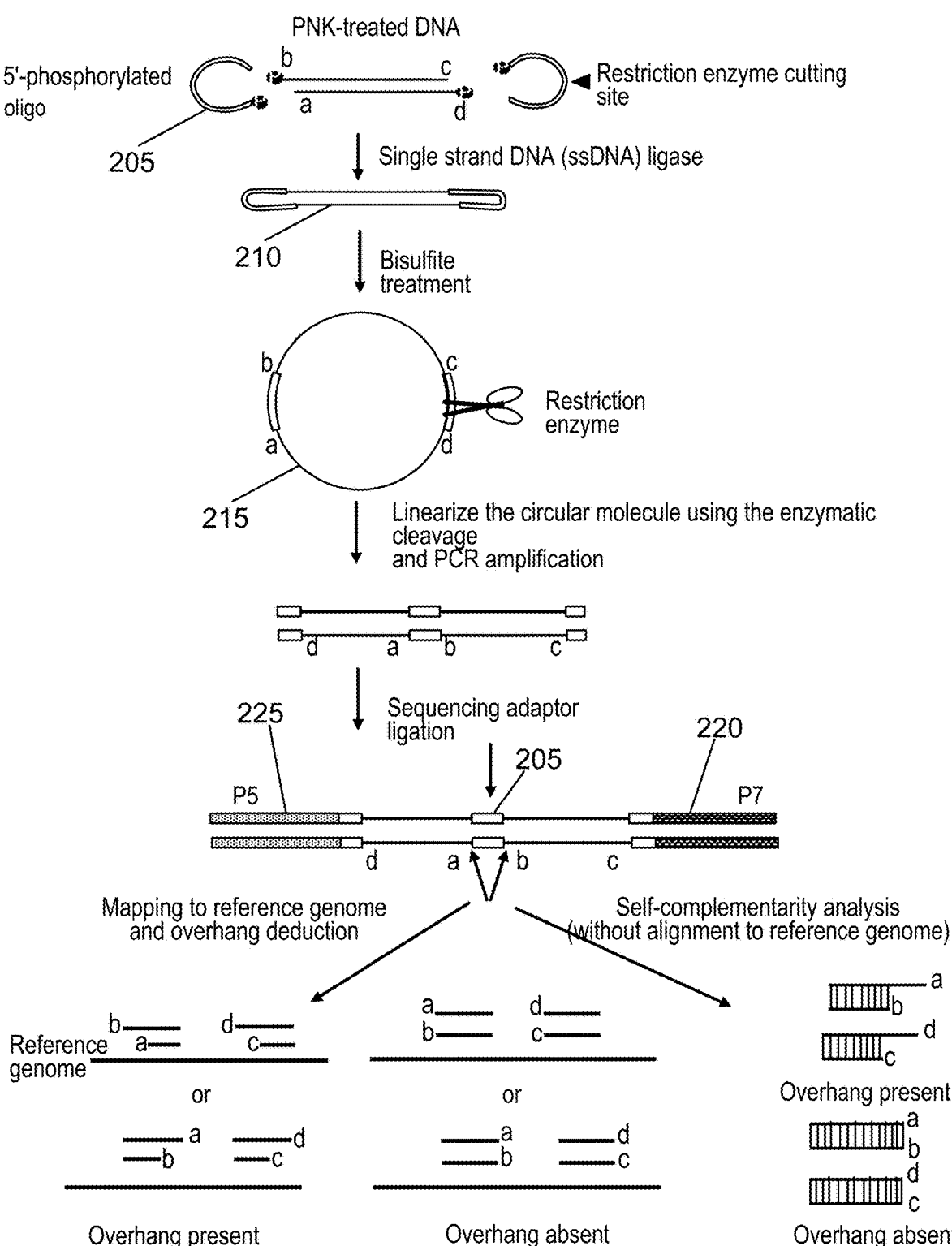
FIG. 2 shows direct assessment of plasma DNA jagged ends through circularization of plasma DNA according to embodiments of the present invention

FIG. 2 shows an embodiment of direct assessment of plasma DNA sticky ends/overhangs through circularization of plasma DNA. The plasma DNA is ligated with single strand DNA adaptors 205 through single-strand DNA (ssDNA) ligase 210. The bisulfite treatment makes the Watson (top strand) and Crick stands (bottom strand) no longer complementary because almost all cytosines from non-CpG sites in both strands are converted to uracils, forming circularized single strand DNA molecules 215. Such circularized single strand DNA 215 may be amplified using random primers (e.g. 5-mers) tagged with 3' sequencing adaptors (e.g. Illumina P7 220, producing a number of linear DNA molecules which may include the single strand DNA adaptor 205. The DNA sequences flanking the originally ligated single strand adaptor would allow for inferring the jagged ends. To enable the linear DNA molecules to be suited for sequencing, the 5' sequencing adaptor (e.g. Illumina P5) 225 is incorporated via annealing and PCR-based extension. Then the molecules tagged with P5 and P7 adaptors 220, 225 will be amplified and sequenced. The sequences ("a" and "b") flanking the original single strand adaptor 205 will be determined through alignment or self-complementarity analysis by studying the relative positions of "a" and "b" sequences as shown in the schematic. The "c" and "d" sequences in circularized molecules can be analyzed through the similar strategy as it is used for analyzing "a" and "b" sequences. Other techniques circularizing DNA and using self-complementarity analysis are possible.

In embodiments not involving measuring methylation levels, the lengths of jagged ends may be used to determine an index. A statistical value of the lengths may be used as the index, including a mean, median, mode, or percentile.

II. Difference in Jaggedness Between Plasma and Urinary DNA

Urinary DNA is observed to exhibit different jaggedness than plasma DNA. Urinary DNA showed a higher jaggedness generally than plasma DNA. Additionally, urinary DNA showed more jaggedness at most sizes of DNA fragments than plasma DNA. Urinary DNA also was observed to show periodicity of jaggedness for different sizes.

A. Jagged End and Methylation Level Comparisons

Figure 3A:
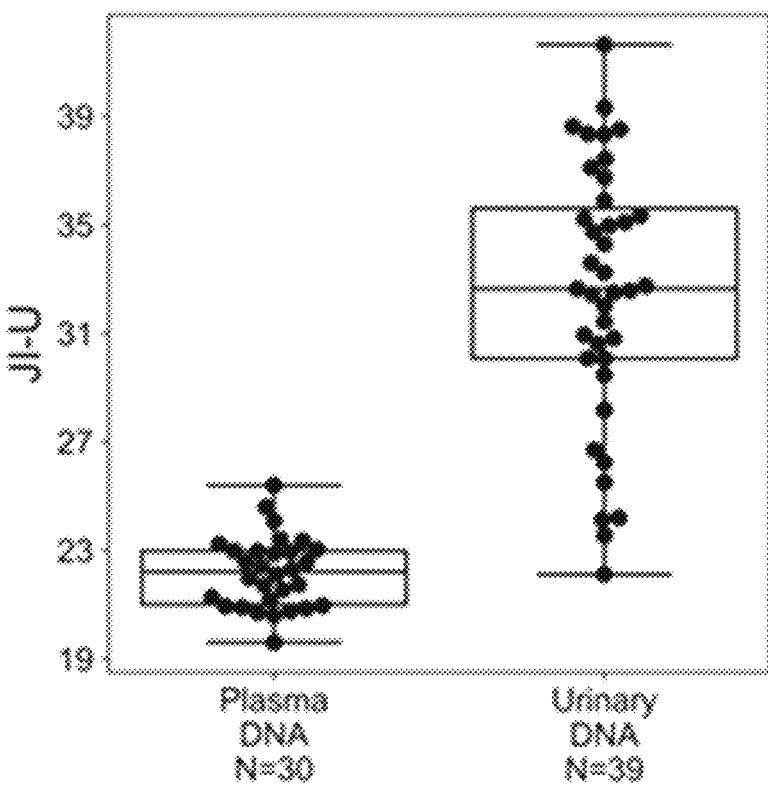
FIGS. 3A and 3B show a comparison of jaggedness between plasma and urinary DNA according to embodiments of the present invention.
Figure 3B:
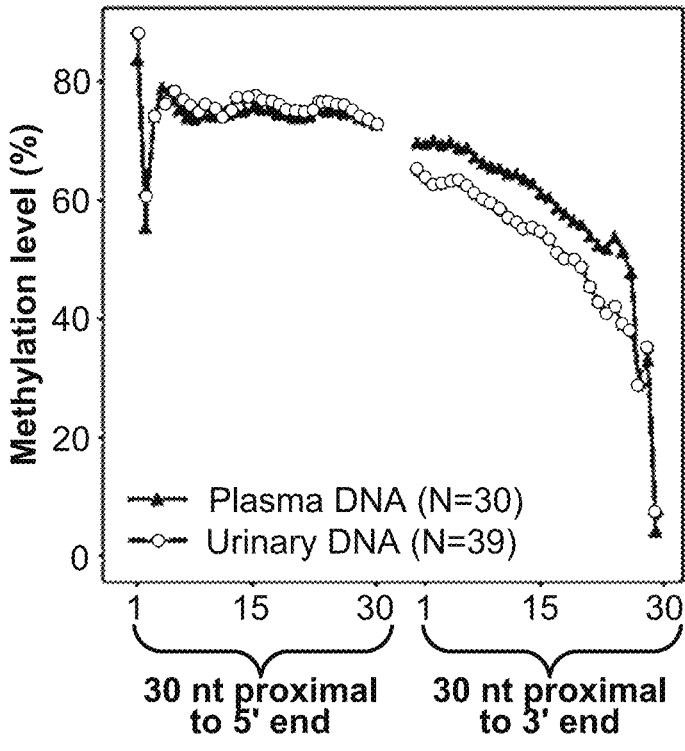

FIG. 3A and FIG. 3B show a comparison of jaggedness between plasma and urinary DNA. FIG. 3A graphs JI-U values between the plasma DNA of pregnant women and urinary DNA of control subjects with hematuria. The y-axis is the jagged index-unmethylated (JI-U). The x-axis shows results for plasma DNA (for 30 subjects) and for urinary DNA (for 39 subjects). FIG. 3A shows that the JI-U values of urinary DNA of control subjects with hematuria (median: 35.8; range: 21.3-60.0) were 1.6 times higher than that of plasma DNA of pregnant women (median: 21.7; range: 14.7-26.2) (P value <0.0001, Mann-Whitney U test).

FIG. 3B graphs methylation levels between plasma (triangles) and urinary (circles) DNA across different loci at the first 30 nucleotides and the last 30 nucleotides of a cell-free DNA fragment. The y-axis shows the methylation level as a percentage of all CpG sites. The x-axis shows the nucleotide position of both 5' and 3' ends of a strand of a fragment. The "nt" stands for nucleotides. In this application "nt" and nucleotides may be used interchangeably with bases. For the "30 nt proximal to 5' end," the higher nucleotide number is farther from the 5' end than a lower nucleotide number. For the "30 nt proximal to 3' end," the lower nucleotide number is farther from the 3' end than a higher nucleotide number. By analyzing methylation levels across different CpG sites in read1 and read2 after pooling all aligned paired-end reads, we observed that the methylation levels proximal to the 3' end of urinary DNA molecules declined more than that of plasma DNA molecules. These results demonstrated that urinary DNA bore more jagged ends when compared with plasma DNA.

B. Size Analysis with Jagged Ends

Figure 4A:
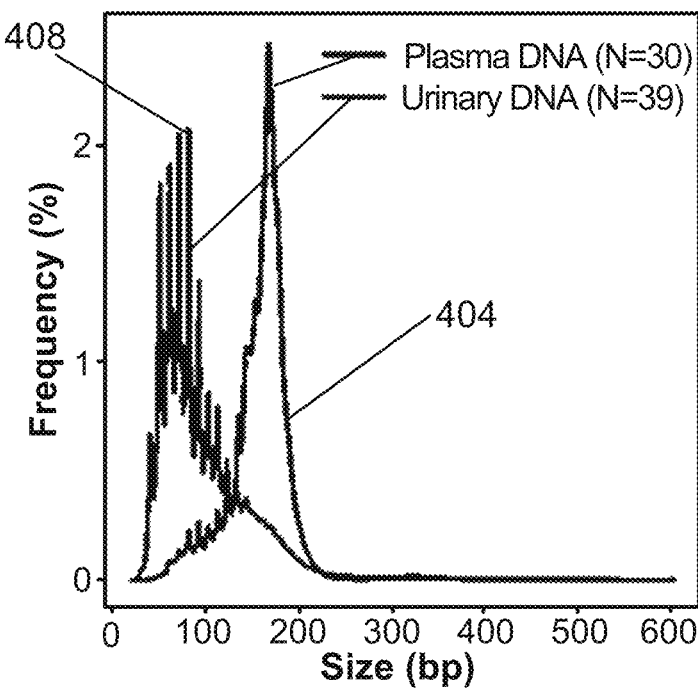
FIGS. 4A and 4B show fragmentation patterns between plasma and urinary DNA according to embodiments of the present invention.
Figure 4B:
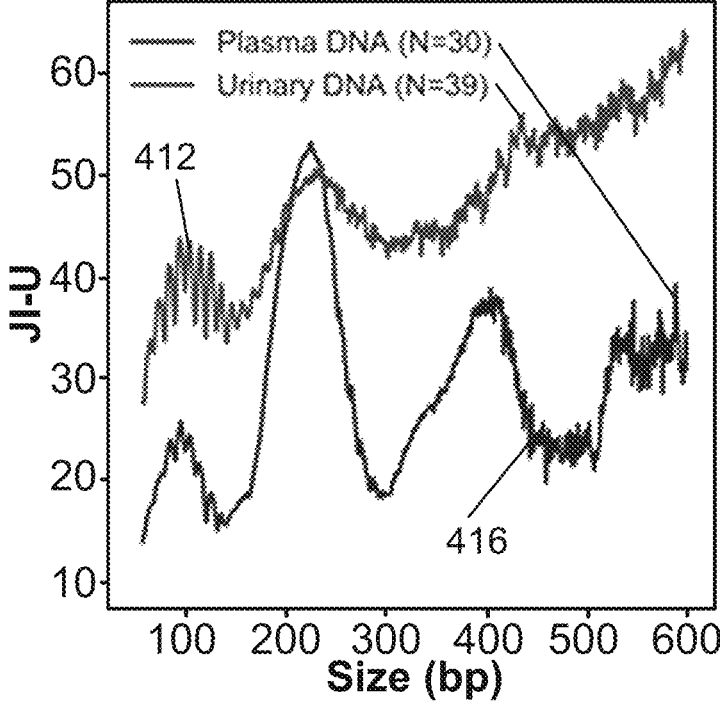

FIG. 4A and FIG. 4B show fragmentation patterns between plasma and urinary DNA. FIG. 4A shows size distributions of plasma DNA of pregnant women (line 404) and urinary DNA of control subjects (line 408). The subjects are the same subjects analyzed in FIG. 3A and FIG. 3B. The x-axis shows the size of the fragment in base pairs. The size of a fragment may be based on the outermost nucleotides of molecules after end repair unless context dictates otherwise. The y-axis shows the frequency of the particular size fragment. FIG. 4A shows that size profiles between urinary and plasma DNA were markedly different. The urinary DNA was more fragmented than plasma DNA.

FIG. 4B shows JI-U values across fragment sizes. The x-axis shows the size of the fragment in base pairs. The y-axis shows JI-U. The JI-U values of urinary DNA (line 412) across each size ranging from 60 to 600 bp were nearly all higher than those of plasma DNA (line 416). Interestingly, the JI-U profile of plasma DNA displayed several strongly-oscillating major peaks in ~165 bp intervals (i.e. approximately one nucleosome unit) and a series of weakly-oscillating minor peaks in ~10 bp periodicities for small molecules, whereas urinary DNA showed weakly-oscillating major peaks but with the presence of strongly-oscillating minor peaks. This different behavior may suggest that urinary DNA jagged ends and plasma DNA jagged ends can be implemented in different ways clinically. For example, the selective analysis of jagged ends in certain size ranges may enhance the performance for urinary DNA jagged end based testing in some embodiments.

III. Differential Jaggedness Between Cancer and Non-Cancer

As bladder tumor DNA molecules were present in urinary DNA from patients with bladder cancer (Cheng et al., Clin Chem. 2019; 65:927-936), we explored the feasibility of using jaggedness of urinary DNA to assess patients with bladder cancer. The jaggedness of urinary DNA was found to vary across different levels of bladder cancer, including for different size ranges of DNA fragments. Results show that different levels of disorders can be classified using measures of jaggedness. Additionally, looking at specific sizes of fragments or specific locations of fragments can improve sensitivity and/or specificity of determining the level of a disorder.

A. Results Showing Differences in Index Value

Figure 5A:
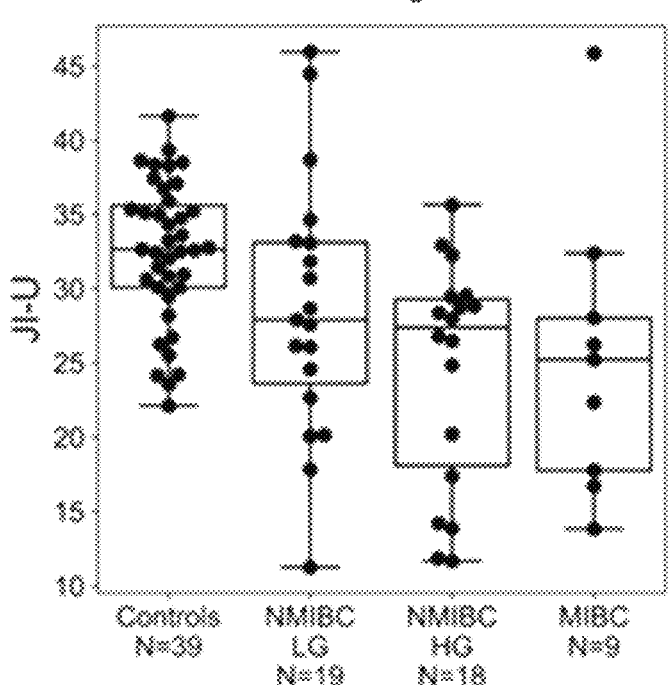
FIGS. 5A, 5B, 5C, and 5D show the relationship of jagged index-unmethylated (JI-U) values in the urinary DNA with bladder cancer according to embodiments of the present invention.

FIGS. 5A, 5B, 5C, and 5D show JI-U values in the urinary DNA of patients with bladder cancer. FIG. 5A shows a boxplot of JI-U across control subjects with hematuria but without bladder cancer, low-grade non-muscle invasive bladder cancer (NMIBC LG), high-grade non-muscle invasive bladder cancer (NMIBC HG), and muscle invasive bladder cancer (MIBC). The x-axis of FIG. 5A shows the control subjects and subjects with bladder cancer. The number of subjects in each group is shown in the x-axis label. The JI-U is shown on the y-axis. As shown in FIG. 5A, compared with cancer-free controls with hematuria (median: 33.9; range 21.3-50.7), the jagged end index (JI-U) of urinary DNA was significantly lower in patients with bladder cancer who frequently presented with hematuria (median: 26.6; range: 3.5-50.7) (P value <0.0001, Mann-Whitney U test). The patients with MIBC showed the lowest median JI-U value.

Figure 5B:
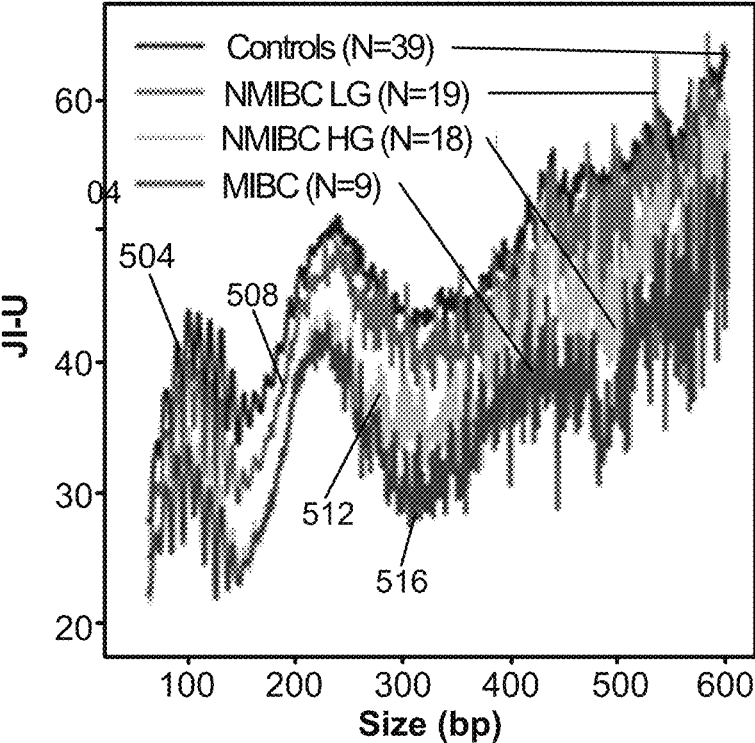

FIG. 5B shows JI-U values varying across different sizes for different types of samples. FIG. 5B shows JI-U on the y-axis and size of fragments in base pairs on the x-axis. Line 504 shows control subjects with hematuria but without bladder cancer. Line 508 shows low-grade non-muscle invasive bladder cancer (NMIBC LG). Line 512 shows high-grade non-muscle invasive bladder cancer (NMIBC HG). Line 516 shows muscle invasive bladder cancer (MIBC). The reduction of jaggedness of urinary DNA in patients with bladder cancer presents regularly across different size ranges.

Figure 5C:
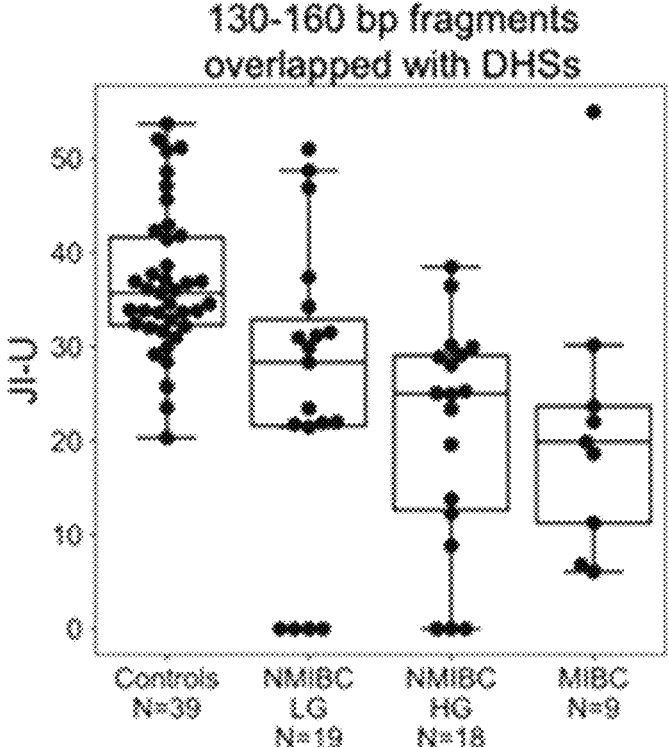

FIG. 5C shows a boxplot of JI-U across control subjects with hematuria but without bladder cancer, low-grade non-muscle invasive bladder cancer (NMIBC LG), high-grade non-muscle invasive bladder cancer (NMIBC HG), and muscle invasive bladder cancer (MIBC), similar to FIG. 5A. However, FIG. 5C shows results for fragments of 130 to 160 bp and overlapping with DNASE1 hypersensitive sites (DHSs). The x-axis of FIG. 5A shows the control subjects and subjects with bladder cancer. The number of subjects in each group is shown in the x-axis label. The JI-U is shown on the y-axis. FIG. 5C shows greater separation between JI-U for control subjects and subjects with bladder cancer compared to FIG. 5A. FIG. 5C also shows that JI-U for 130 to 160 bp shows more differentiation between the different bladder cancer grades compared to the results shown in FIG. 5A.

Based on the fact that DNASE1 activity in urine was much higher than in plasma (Nadano et al., Clin Chem. 1993; 39:448-52), in one embodiment, one could employ urinary DNA molecules that overlapping DHSs for jagged end analysis. A DHS was defined as a genomic region showing an overrepresentation of DNASE I cleavage sites. DHSs were downloaded from ENCODE (encyclopedia of DNA elements) database (encodeproject.org). Differentiating cancer using 130 to 160 bp fragments overlapped with DHSs was improved compared to differentiating with all fragments (P value: 0.02, DeLong test).

B. Classification Accuracy

Figure 5D:
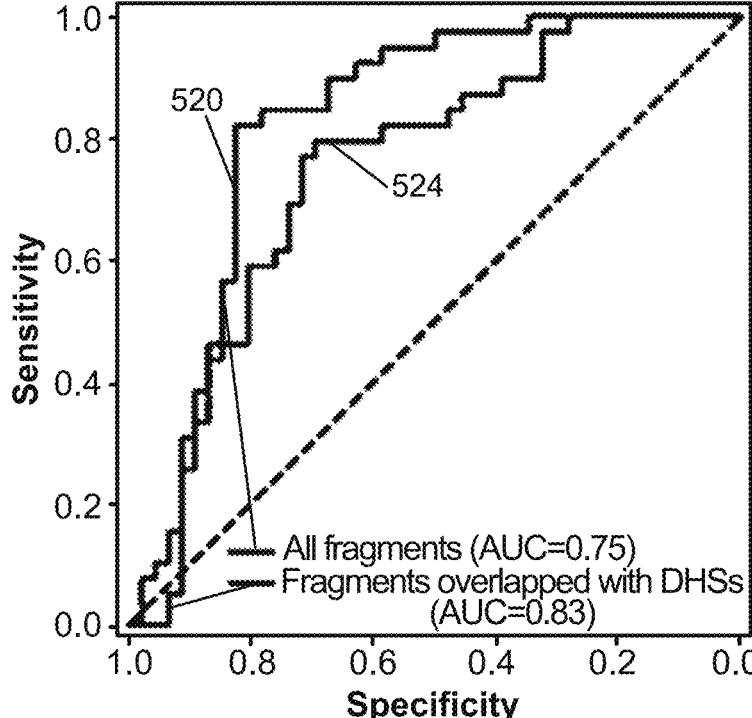

FIG. 5D shows receiver operating characteristic (ROC) curves for using JI-U to determine bladder cancer. Sensitivity is shown on the y-axis, and specificity is shown on the x-axis. Curve 520 is for using JI-U with on all fragment sizes. Curve 524 is for using JI-U with fragment sizes within a range of 130 to 160 bp and overlapping with DNASE1 hypersensitive sites (DHSs). The area under the ROC curve (AUC) was 0.75 when using all fragments. These results suggested that jagged ends of urinary DNA could be served as a biomarker for bladder cancer. The observation for the jaggedness of urinary DNA in patients with bladder cancer was opposite to that observed for plasma DNA jagged ends. The jaggedness of tumoral DNA in plasma of patients with HCC was higher than that DNA of hematopoietic origin (Jiang et al., Genome Res. 2020; 30:1144-1153), further suggesting the different properties of jagged ends of plasma and urinary DNA molecules.

As a result, we observed an enhanced performance of differentiating patients with and without bladder cancer (AUC: 0.83) (FIG. 5D). In some embodiments, one could use, but not limited to, a size range of 40 to 70 bp, 70 to 100 bp, 100 to 130 bp, 130 to 160 bp, 160 to 190 bp, etc. and/or size ranges, including combinations of these size ranges.

C. Example Methods

Figure 6:
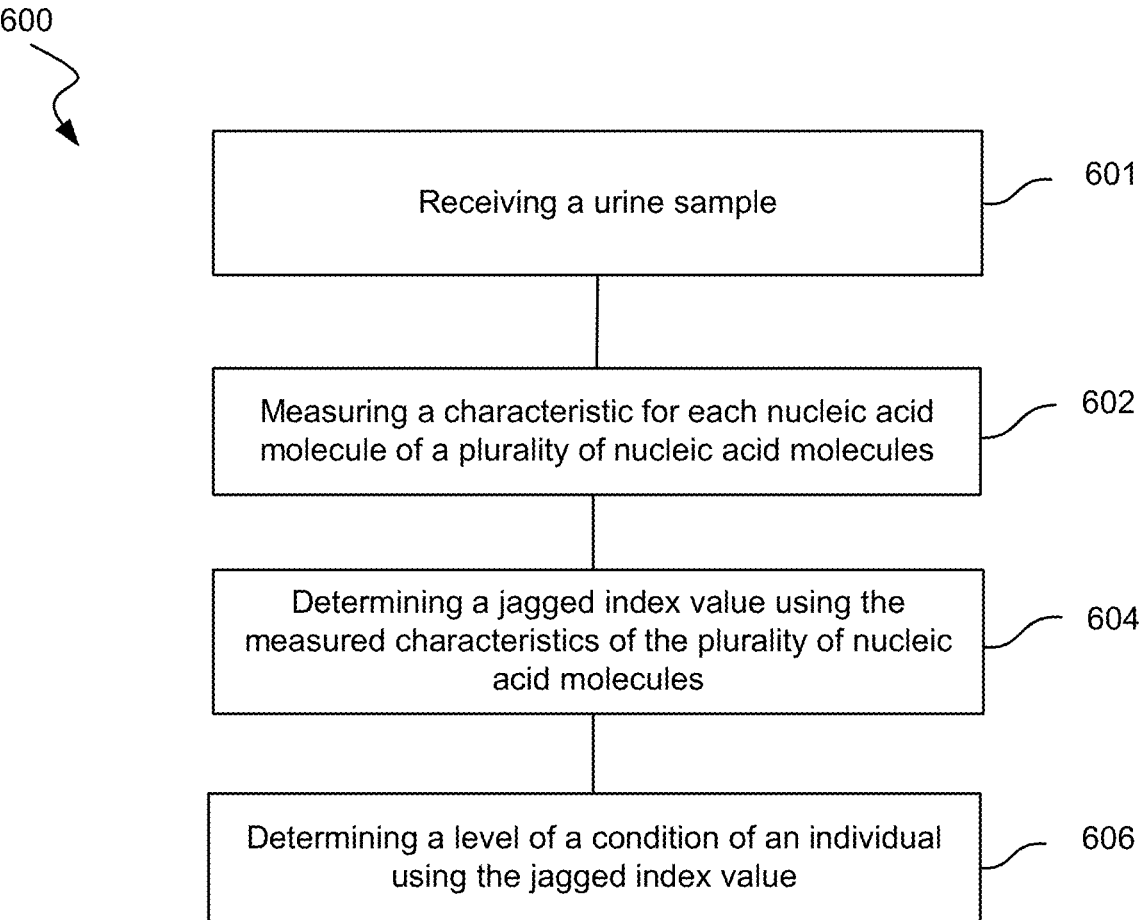
FIG. 6 shows a method using jagged end index values to analyze a urine sample according to embodiments of the present invention.

FIG. 6 shows a method 600 using jagged end index values to analyze a urine sample.

At block 601, a urine sample may be received. The urine sample may be obtained from an individual. The urine sample may include a plurality of nucleic acid molecules, which are cell-free. Each nucleic acid molecule of the plurality of nucleic acid molecules may be double-stranded with a first strand having a first portion and a second strand. The first portion of the first strand of at least some of the plurality of nucleic acid molecules may overhang the second strand, may not be hybridized to the second strand. The first portion may be at a first end of the first strand. The first end may be a 3' end or a 5' end.

A statistically significant number of cell-free nucleic acid molecules can be analyzed so as to provide an accurate determination the proportional contribution from the first tissue type. In some embodiments, at least 1,000 cell-free nucleic acid molecules are analyzed. In other embodiments, at least 10,000 or 50,000 or 100,000 or 500,000 or 1,000,000 or 5,000,000 cell-free nucleic acid molecules, or more, can be analyzed. As a further example, at least 10,000 or 50,000 or 100,000 or 500,000 or 1,000,000 or 5,000,000 sequence reads can be generated. The number of cell-free nucleic acid molecules analyzed may apply to any method described herein.

At block 602, method 600 may include measuring a characteristic of each nucleic acid molecule of the plurality of nucleic acid molecules. Measuring may include measuring a characteristic of a first strand, a second strand, or the first strand and the second strand that correlates to (e.g., is proportional to) a length of the first strand that overhangs or is not hybridized to the second strand. The characteristic may also correlate to a length of the first strand that overhangs the second strand. The characteristic may be measured for each nucleic acid of a plurality of nucleic acids. The characteristic may be a methylation status at one or more sites at end portions of the first and/or second strands of each of the plurality of nucleic acid molecules. The characteristic may be measured by any technique described. In some embodiments, the characteristic may be the length of the first strand that overhangs or is not hybridized to the second strand. The length may be directly determined.

In some embodiments, method 600 may include measuring sizes of nucleic acid molecules. The plurality of nucleic acid molecules may have sizes within a specified range. The specified range may be from 40 to 70 bp, 70 to 100 bp, 100 to 130 bp, 130 to 160 bp, 160 to 190 bp, 190 to 250 bp, greater than 250 bp, any range less than the entire range of sizes present in the biological sample, any range described herein, or any combination of ranges (including discontinuous ranges) described herein. The specified range may be based on previous data showing statistically significant separation between different condition levels. The size range may be based on the size of the shorter strand or the longer strand. The size range may be based on the outermost nucleotides of molecules after end repair. If the 5' end protrudes, then 5' to 3' polymerase mediated elongation will occur and the size may be the longer strand. If the 3' end protrudes, without a DNA polymerase with a 3' to 5' synthesis function, the 3' protruded single-strand may be trimmed and the size may then be the shorter strand.

In embodiments, method 600 may include analyzing nucleic acid molecules to produce reads. The reads may be aligned to a reference genome. The plurality of nucleic acid molecules may be reads within a certain distance range relative to a transcription start site or a binding site, including a CTCF site or a DNASE1 hypersensitive sites (DHS) site. Methods related to distances from certain sites are discussed in further detail elsewhere in this disclosure.

At block 604, a jagged index value using the measured characteristics of the plurality of nucleic acid molecules may be determined. The jagged index value may be a jagged end value, including Jagged Index-Unmethylated (JI-U) or Jagged Index-Methylated (JI-M), as described later. The jagged index value may include a methylation level over the plurality of nucleic acid molecules at one or more sites of end portions of the first and/or second strands. In some embodiments, the jagged index value may be a statistical value (e.g., mean, median, mode, percentile) of the lengths of jagged ends of the plurality of nucleic acid molecules.

If the first plurality of nucleic acid molecules are in a specified size range, methods may include measuring the characteristic of each nucleic acid molecule of a second plurality of nucleic acid molecules. The second plurality of nucleic acid molecules may have sizes with a second specified size range. Determining the jagged index value may include calculating a ratio using the measured characteristics of the first plurality of nucleic acid molecules and the measured characteristics of the second plurality of nucleic acid molecules.

The jagged index value may be compared to a reference value. The reference value or the comparison may be determined using machine learning with training data sets.

At block 606, a level of a condition of an individual may be determined using the jagged index value. In some embodiments, the level of condition may be determined based on the comparison of the jagged index value to the reference value. The level of the condition may be classified as being present, likely, or severe when the jagged index value exceeds the reference value. The condition may include a disease, a disorder, or a pregnancy. The condition may be cancer, an auto-immune disease, a pregnancy-related condition, or any condition described herein. As examples, cancer may include bladder cancer, hepatocellular carcinoma (HCC), colorectal cancer (CRC), leukemia, lung cancer, or throat cancer. The auto-immune disease may include systemic lupus erythematosus (SLE). In some embodiments, the disease may include a urological problem, urinary tract infection, inflammation of kidneys, or inflammation of the bladder (i.e., cystitis). Various data below provides examples for determined a levels of a condition.

The method may further include treating the disease or condition in the patient after determining the level of the disease or condition in the patient. Treatment can be provided according to a determined level of cancer, the identified mutations, and/or the tissue of origin. For example, an identified mutation (e.g., for polymorphic implementations) can be targeted with a particular drug or chemotherapy. The tissue of origin can be used to guide a surgery or any other form of treatment. And, the level of cancer can be used to determine how aggressive to be with any type of treatment, which may also be determined based on the level of cancer. A cancer may be treated by chemotherapy, drugs, diet, therapy, and/or surgery. In some embodiments, the more the value of the parameter exceeds the reference value, the more aggressive the treatment may be.

Treatments may include transurethral bladder tumor resection (TURBT). This procedure is used for diagnosis, staging and treatment. During TURBT, a surgeon inserts a cystoscope through the urethra into the bladder. The tumor is then removed using a tool with a small wire loop, a laser, or high-energy electricity. For patients with NMIBC, TURBT may be used for treating or eliminating the cancer. Another treatment may include radical cystectomy and lymph node dissection. Radical cystectomy is the removal of the whole bladder and possibly surrounding tissues and organs. Treatment may also include urinary diversion. Urinary diversion is when a physician creates a new path for urine to pass out of the body when the bladder is removed as part of treatment.

Treatment may include chemotherapy, which is the use of drugs to destroy cancer cells, usually by keeping the cancer cells from growing and dividing. The drugs may involve, for example but are not limited to, mitomycin-C (available as a generic drug), gemcitabine (Gemzar), and thiotepa (Tepadina) for intravesical chemotherapy. The systemic chemotherapy may involve, for example but not limited to, cisplatin gemcitabine, methotrexate (Rheumatrex, Trexall), vinblastine (Velban), doxorubicin, and cisplatin.

In some embodiments, treatment may include immunotherapy. Immunotherapy may include immune checkpoint inhibitors that block a protein called PD-1. Inhibitors may include but are not limited to atezolizumab (Tecentriq), nivolumab (Opdivo), avelumab (Bavencio), durvalumab (Imfinzi), and pembrolizumab (Keytruda).

Treatment embodiments may also include targeted therapy. Targeted therapy is a treatment that targets the cancer's specific genes and/or proteins that contributes to cancer growth and survival. For example, erdafitinib is a drug given orally that is approved to treat people with locally advanced or metastatic urothelial carcinoma with FGFR3 or FGFR2 genetic mutations that has continued to grow or spread of cancer cells.

Some treatments may include radiation therapy. Radiation therapy is the use of high-energy x-rays or other particles to destroy cancer cells. In addition to each individual treatment, combinations of these treatments described herein may be used. In some embodiments, when the value of the parameter exceeds a threshold value, which itself exceeds a reference value, a combination of the treatments may be used. Information on treatments in the references are incorporated herein by reference.

The classification of a condition may also be based on other clinical factors. For example, an individual may be considered to be at risk of a particular condition because of genetic factors or because of age. In some examples, the individual may be exhibiting symptoms of the condition.

When block 606 is implemented, the reference value can be determined using one or more reference samples of subjects that have the condition. As another example, the reference value is determined using one or more reference samples of subjects that do not have the condition. Multiple reference values can be determined from the reference samples, potentially with the different reference values distinguishing between different levels of the condition. The reference value may be any reference value described herein.

In some embodiments, the comparison to the reference can involve a machine learning model, e.g., trained using supervised learning. The jagged index values (and potentially other criteria, such as copy number, size of DNA fragments, and methylation levels) and the known conditions of training subjects from whom training samples were obtained can form a training data set. The parameters of the machine learning model can be optimized based on the training set to provide an optimized accuracy in classifying the level of the condition. Example machine learning models include neural networks, decision trees, clustering, and support vector machines.

IV. Nucleosomal Footprints with End Densities

The end densities near a CTCF binding site were studied. The end densities may be offset between the U-ends and the D-ends of DNA fragments. We investigated whether the difference between the densities of the different ends may be used to determine a level of a condition. The differences in densities of the different ends of urinary DNA was used to accurately determine different levels of bladder cancer.

A. Differences in End Densities

Figure 7A:
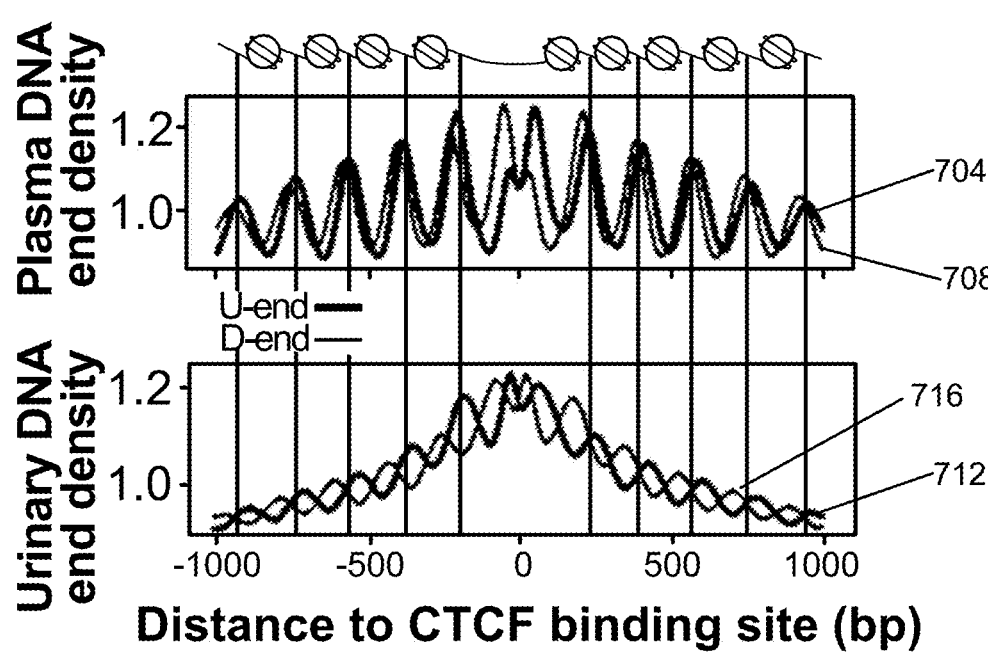
FIGS. 7A and 7B show relationships between end density and nucleosome tracks according to embodiments of the present invention.

FIG. 7A shows the U-end and D-end densities near CTCF binding sites for plasma and urinary DNA molecules. The y-axis is the plasma DNA end density. The end density is the value of end occurrence normalized by the median of those values across loci spanning 1-kb up/downstream relative to CTCF binding sites. The top graph shows end density for plasma DNA. Line 704 represents the upstream end. Line 708 represents the downstream end. The bottom graph shows end density of urinary DNA. Line 712 represents the upstream end. Line 716 represents the downstream end. The x-axis is the distance in base pairs from a CTCF binding site. A positive number is downstream of the CTCF binding site. A negative number is upstream of the CTCF binding site. The cartoon above the top graph illustrates a possible nucleosomal structure associated with the results for the end density with plasma DNA and with urinary DNA. The data for FIG. 7A comes from both subjects with cancer and subjects without cancer.

As seen in FIG. 7A, for plasma DNA molecules derived from the Watson strand (i.e., the strand identical to the strand shown in the reference genome), both the U-end and D-end densities near CTCF binding sites displayed periodic signals with a ~180 bp interval, resembling well-organized patterns of nucleosomal arrays. The distance between two consecutive peaks of end density may facilitate the determination of a nucleosome footprint. The peaks of end density were suggestive of preferred cutting during the plasma DNA generation. The orientation patterns of U-end and D-end densities were also observed nearby CTCF binding sites (up-/downstream 300), which was consistent with a previous report (Sun et al. Genome Res. 2019; 29:418-27). The small offset (~20 bp) between U-end and D-end density tracks outside the range of upstream and downstream 300 bp of CTCF binding sites was likely due to partial degradation of the linker DNA. In contrast, for urinary DNA molecules, the patterns of nucleosomal arrays became less evident while the offset became wider, likely suggesting that there was further DNA degradation during the generation of urinary DNA fragments in comparison to plasma DNA generation.

Figure 7B:
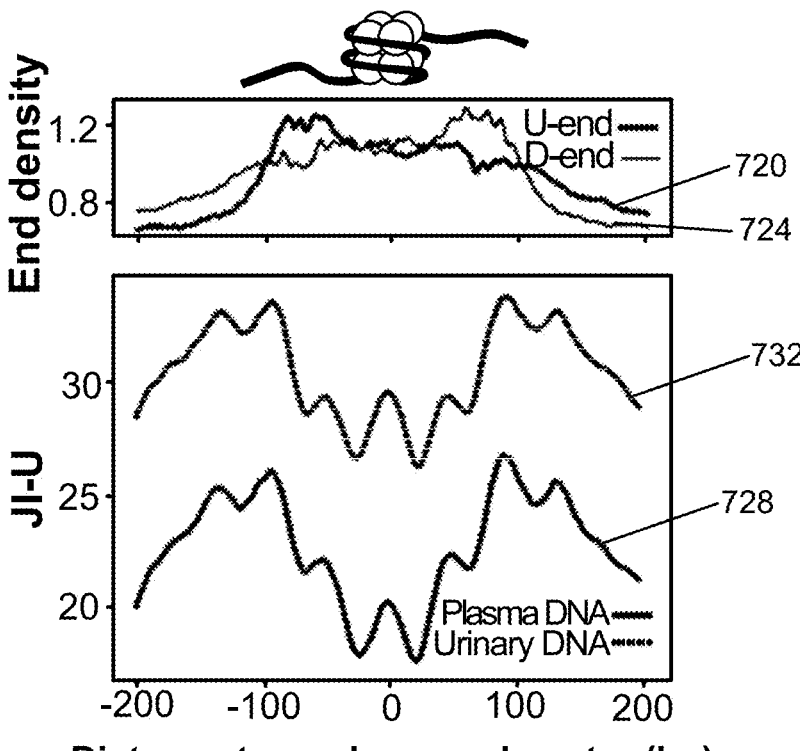

FIG. 7B graphs end densities and JI-U values were distributed across loci relative to nucleosomal centers. The x-axis for both graphs is the distance to a nucleosomal center. The top graph shows end density on the y-axis. The top graph plots the end densities of U-ends (line 720) and D-ends (line 724) based on plasma DNA molecules. The bottom graph shows JI-U values for both plasma DNA (line 728) and urinary DNA (line 732). The cartoon above the top graph illustrates the position of the nucleosomal center relative to the x-axis. The top graph shows that the U-end and D-end densities were enriched in regions proximal to the linker regions, which was in line with the previous report (Sun et al., Proc Natl Acad Sci USA. 2018; 115: E5106-14). The bottom graph shows that the JI-U values were observed to be relatively higher in regions proximal to linker regions than other locations. A rise of 22.4% in the average JI-U of plasma DNA was observed in linker DNA regions compared with nucleosomal core regions. For urinary DNA, the average JI-U in the linker DNA region was increased by 13.1%.

Figure 8:
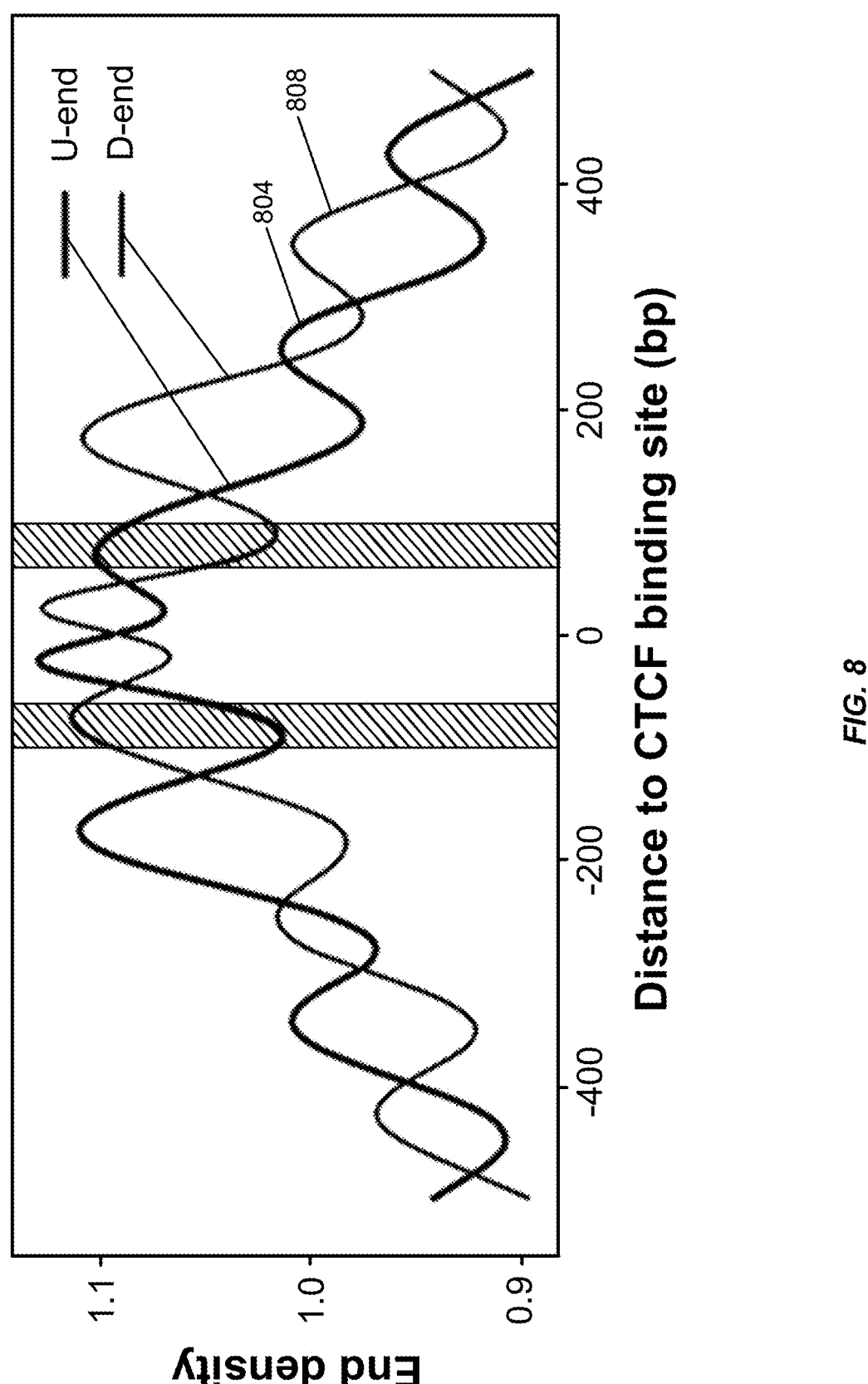
FIG. 8 is a graph of the end densities for urinary DNA relative to a CTCF binding site according to embodiments of the present invention.

FIG. 8 is a graph of the end densities for urinary DNA relative to a CTCF binding site. The y-axis shows the occurrence of urinary DNA ends (i.e., end density). The x-axis shows the distance in base pairs from a CTCF binding site. The end density was the value of end occurrence normalized by the median of those values across loci spanning 1-kb up/downstream relative to CTCF binding sites. Line 804 represents the upstream end. Line 808 represents the downstream end. The vertical columns in the graph highlight distance ranges of −80±20 bp and +80±20 bp. The U-end and D-end density of urinary DNA show periodic signals surrounding CTCF binding sites. The densities of U-end and D-end may be used as biomarkers for informing pathophysiologic states within open chromatin regions. The data for FIG. 8 is based on subjects without cancer.

We used a cumulative difference ($\Delta C1$) in end density between D-end and U-end within a distance range of −80±20 bp and a cumulative difference ($\Delta C2$) between U-end and D-end within a distance range of +80±20 bp to as measurements. In one embodiment, the sum of $\Delta C1$ and $\Delta C2$ ($\Delta C$) may be used as a molecular indicator for assessing whether a patient may have a cancer. The size ranges of −80±20 bp and +80±20 bp showed an offset between U-end and D-end end densities. In other embodiments, the size ranges may include, but are not limited to, −40±20 bp, −50±20 bp, −60±20 bp, −70±20 bp, −100±20 bp, +40±20 bp, +50±20 bp, +60±20 bp, +70±20 bp, +100±20 bp, or combinations of these ranges.

Figure 9:
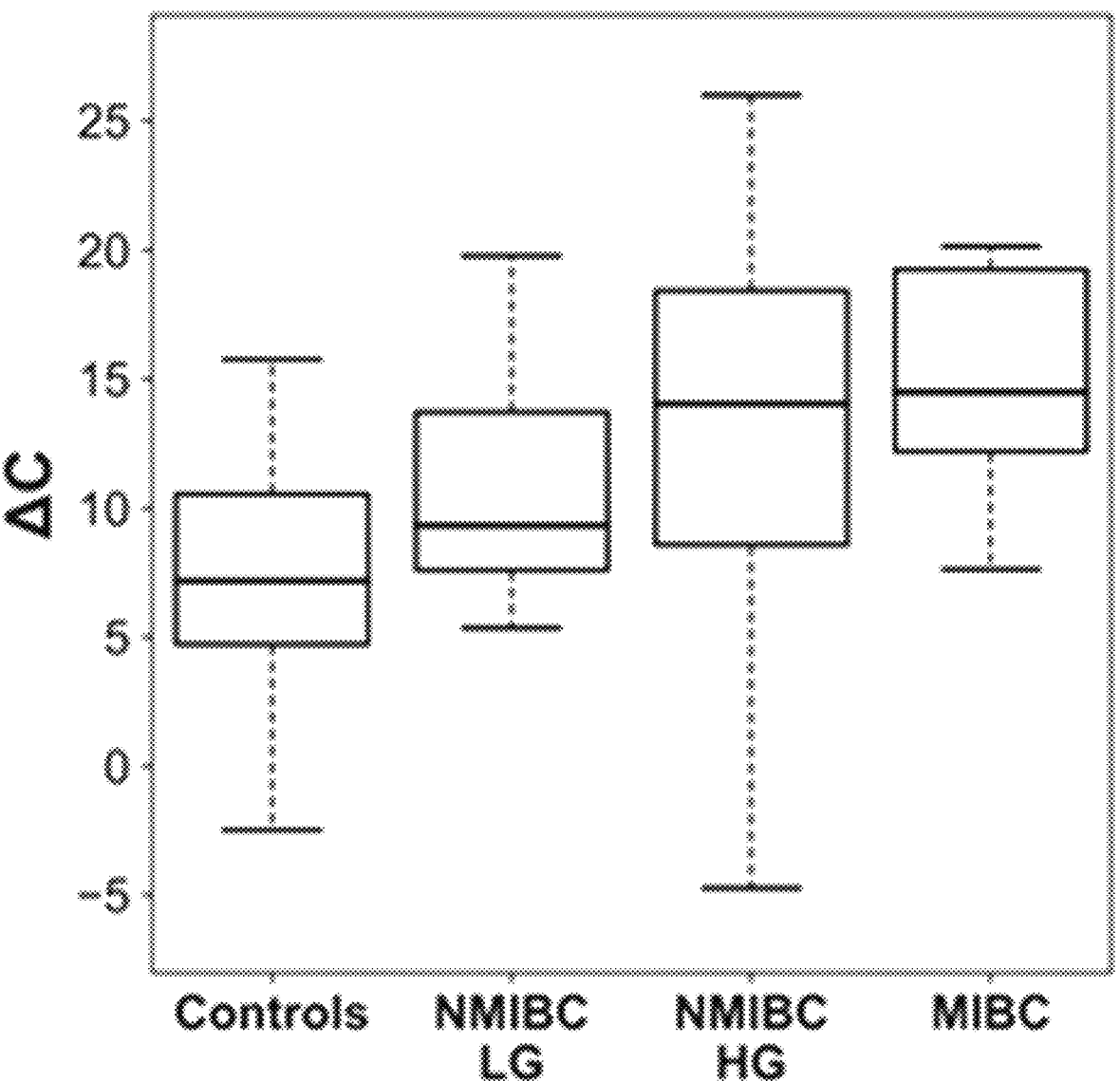
FIG. 9 is a boxplot of cumulative difference of end density across different bladder cancer conditions according to embodiments of the present invention.

FIG. 9 shows a boxplot of cumulative difference of end density ($\Delta C$) across control subjects with hematuria, and patients with low-grade non-muscle invasive bladder cancer (NMIBC-LG), high-grade non-muscle invasive bladder cancer (NMIBC-HG) and muscle invasive bladder cancer (MIBC). The y-axis shows the cumulative difference of end density ($\Delta C$). The x-axis shows the different groups of subjects. The $\Delta C$ values of urinary DNA were significantly higher in patients with bladder cancer (median: 12.8; range: −36.1-25.9), compared with subjects without cancer (median: 7.2; range: −4.9-22.77) (P value <0.0001, Mann Whitney U test). The results suggested that $\Delta C$ may be used for detecting cancer in a noninvasive way.

B. Classification Accuracy

Figure 10B:
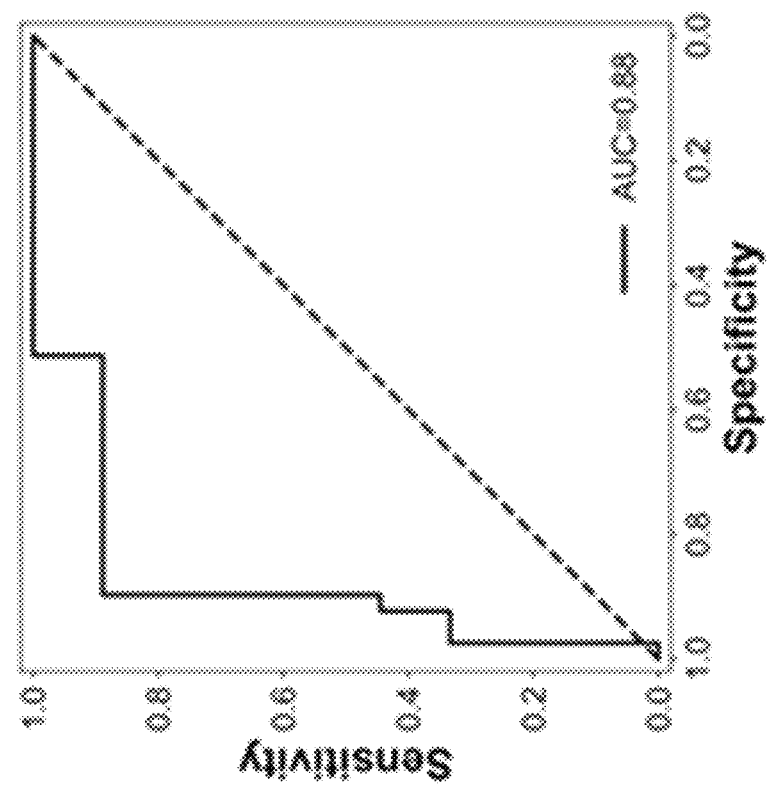
FIGS. 10A and 10B show ROC curves for differentiating between patients with and without cancer using an end density metric according to embodiment of the present invention.
Figure 10A:
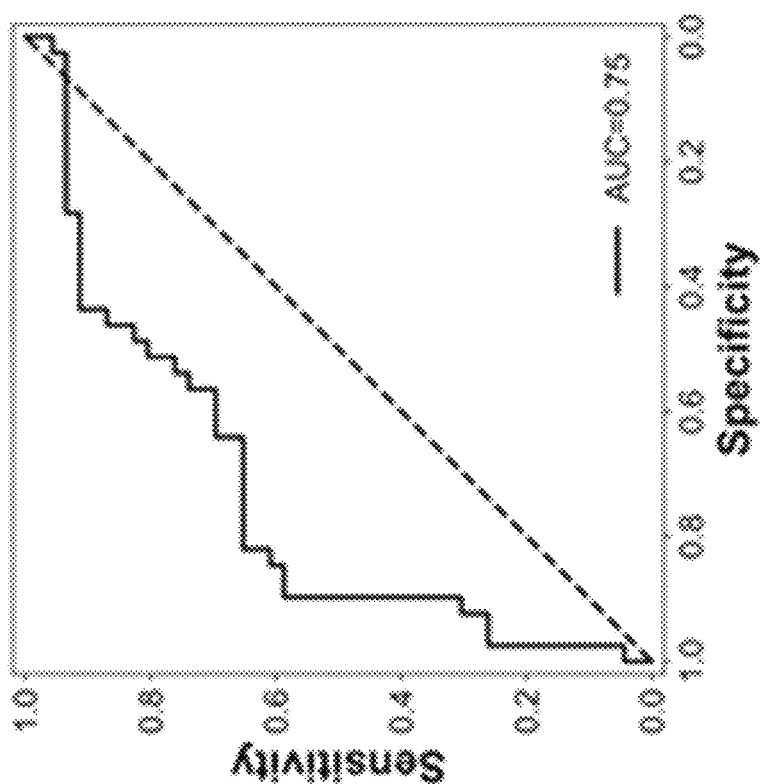

FIG. 10A and FIG. 10B show ROC curves for differentiating between patients with and without cancer using the $\Delta C$ metric. Both graphs have sensitivity on the y-axis and specificity on the x-axis. FIG. 10A is an ROC curve using all patients with any level of bladder cancer versus control subjects. The AUC is 0.75 for distinguishing subjects with any level of bladder cancer from control subject. FIG. 10B is an ROC curve using patients with muscle invasive bladder cancer (MIBC) versus control subjects. The AUC is 0.88 for distinguishing subjects with MIBC from control subjects. These data suggest that the power of $\Delta C$ metric for cancer detection may vary based on the cancer stage. A more advanced stage of cancer may result in a larger $\Delta C$ metric and a higher AUC. The data also suggest that different stages of cancer may be distinguished based on the $\Delta C$ metric.

C. Example Methods

FIG. 11 shows a method 1100 of analyzing a biological sample obtained from an individual. The biological sample may be any biological sample described herein. In some embodiments, the biological sample may be a urine sample. The biological sample may include a plurality of nucleic acid molecules. The plurality of nucleic acid molecules being cell-free.

At block 1102, a set of nucleic acid molecules of the plurality of nucleic acid molecules may be detected. Each nucleic acid molecule of the set of nucleic acid molecules may be characterized by at least one end having a genomic location at a specified distance from a predetermined type of genomic site. The predetermined type may be associated with a modification of a protein in chromatin at the genomic site or a protein interaction at the genomic site. Predetermined may mean that the type of site is determined before sequencing and/or aligning. The genomic site may be a CTCF binding site or a DNASE1 hypersensitive site (DHS). In some embodiments, the genomic site may be a nucleosomal center, an edge of nucleosome, or a region corresponding to a nucleosome.

Identifying the set of nucleic acid molecules may include sequencing each nucleic acid molecule of the set of nucleic acid molecules to produce one or more reads. The sequencing may be performed in various ways, e.g., as described herein. The one or more reads may be aligned to a reference genome (e.g., a human reference genome). The genomic location of the nucleic acid molecule may be determined from the one or more reads.

At block 1104, one end of each nucleic acid molecule of the set of nucleic acid molecules may be classified as an upstream end and the other end as a downstream end. The classification may include aligning each nucleic acid molecule. The alignment may result in determining genomic coordinates at or near the ends of the nucleic acid molecule. The downstream end may be identified based on the end that has a higher value for the genomic location (e.g., a higher genomic coordinate). In some embodiments, the 5' end may be determined by being upstream of DNA polymerase extension direction (i.e. 5'→3' DNA synthesis). In some embodiments, the 5' and 3' ends may be determined by the chemical structure of the nucleotide. For example, the fifth carbon of the deoxyribose ring generally carries a phosphate group (i.e., 5' end), while the third carbon of the deoxyribose ring generally carries a hydroxyl group (i.e., 3' end). As a result, both ends may be classified.

At block 1106, a first amount of nucleic acid molecules having upstream ends at the specified distance may be determined. The first amount may be a number, a total length, or a total mass of nucleic acid molecules.

At block 1108, a second amount of nucleic acid molecules having downstream ends at the specified distance may be determined. The second amount may be a number, a total length, or a total mass of nucleic acid molecules.

At block 1110, a separation value using the first amount and the second amount may be determined. The separation value may be a difference or a ratio of the amounts.

The separation value may be compared to a reference value. The reference value may be determined from one or more control samples from subjects not having the condition or from one or more control samples from subjects that have the condition. The reference value may be determined as any reference value described herein.

At block 1112, a level of a condition of the individual may be determined using the separation value. The determination may be based on comparing the separation value to the reference value. The condition may be any condition described herein. A more severe level of the condition may be associated with a larger separation value. When the separation value exceeds the reference value, the individual may be classified as having the condition or having a high likelihood of the condition. Methods may include treating the condition with a treatment described herein.

In some embodiments, the classification can be performed using a machine learning model, e.g., as described for block 606 of FIG. 6.

V. Enrichment of Clinically-Relevant DNA

Certain types of tissues or samples may have different jaggedness properties than others. For example, fetal DNA may be more jagged than maternal DNA. For recipients of transplanted tissues, the DNA of the recipient may have a different jaggedness than the DNA of the donor. Accordingly, enriching or filtering (either physically or in silico) DNA for certain amounts or ranges of jaggedness can be used to enhance the signal of a particular type of tissue. The enriched DNA can then be used for different analysis.

A. Jagged Ends Between Maternal and Fetal Urinary DNA Molecules of Pregnant Women We also studied the difference of jaggedness between maternal- and fetal-derived molecules in the urinary DNA of pregnant women. We genotyped the maternal buffy coat and placental tissue using a microarray platform (Human Omni2.5, Illumina). Voided urine samples from 5 pregnant women were collected.

There were a median of 191,143 informative single nucleotide polymorphism (SNP) loci (range: 311-207,363) for which the mother was homozygous (i.e. AA) and the fetus was heterozygous (i.e. AB), allowing for defining the fetal-specific alleles. We obtained a median of 191,655 informative SNP loci (range: 8,764-214,815) for which the mother was heterozygous (i.e. AB) and the fetus was homozygous (i.e. AA), allowing for defining the maternal-specific alleles. Urinary DNA molecules that carried the maternal- and fetal-specific alleles were deemed as maternal-derived and fetal-derived urinary DNA molecules.

A median of 45 million (range: 25-93 million) mapped paired-end urinary DNA reads were obtained from each pregnancy plasma subject. The median fetal DNA fraction among those samples was 0.5% (range: 0.4%-0.9%). All the maternal- and fetal-specific DNA molecules were pooled respectively and used for calculating the jagged end index (JI-U) according to the embodiments in this disclosure.

Figure 12:
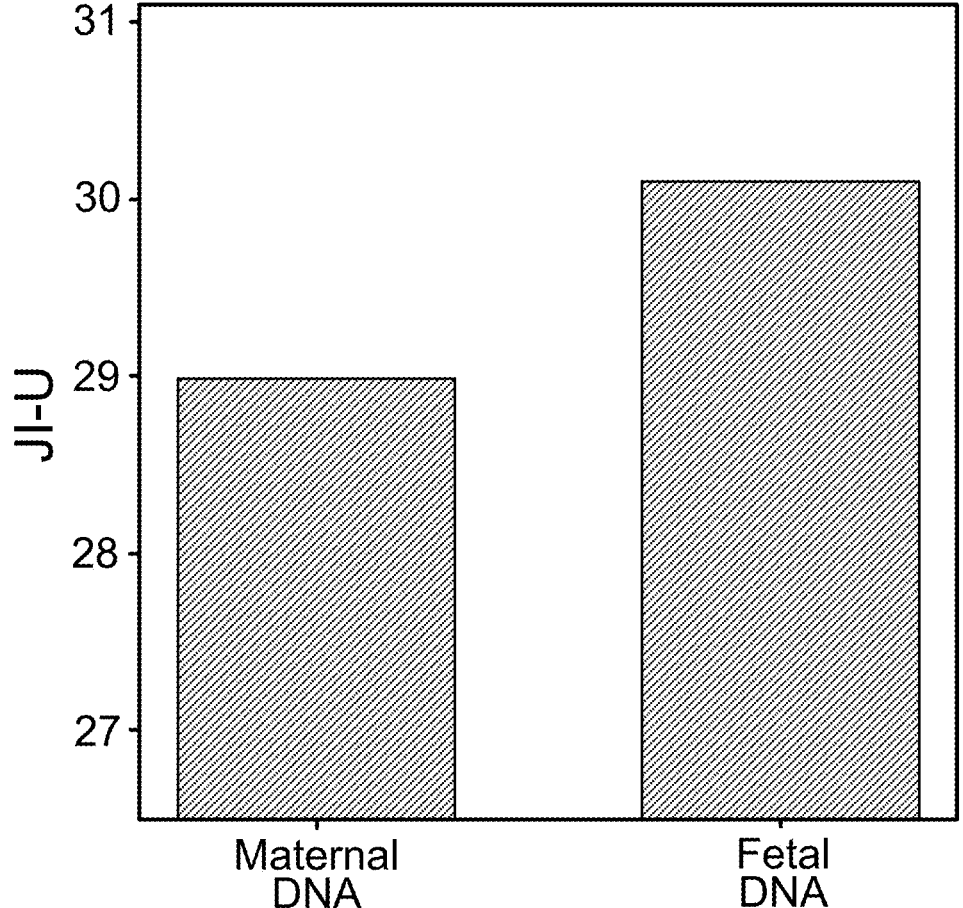
FIG. 12 shows JI-U values between maternal-derived and fetal-derived urinary DNA of pregnant women according to embodiments of the present invention.

FIG. 12 shows JI-U values between maternal-derived and fetal-derived urinary DNA of pregnant women. The y-axis shows JI-U. The x-axis shows maternal-derived DNA and fetal-derived DNA. As shown in FIG. 12, the JI-U of fetal urinary DNA (JI-U: 30.1) is higher than that of maternal DNA (JI-U: 28.9) in the urine of pregnant women. In other words, a 4.1% increase of JI-U values was observed in fetal-derived urinary DNA, compared with the maternal-derived urinary DNA. These results suggested that the jagged ends of urinary DNA may reflect the tissues of origin. The jaggedness of urinary DNA may be useful for non-invasive prenatal testing. For example, the DNA molecules with a higher jaggedness index would enrich the fetal DNA. Such a selection based on urinary DNA jagged ends would facilitate the detection of fetal disorders using urinary DNA molecules, as the higher the fetal DNA fraction in the urinary DNA pool, the more sensitive the detection of fetal disorders using urinary DNA would be.

B. Jagged Ends in Patients with Transplantation

We analyzed JI-U of urinary DNA in 12 patients with transplantation, including renal transplantation (n=10), a hematopoietic stem cell transplantation (HSCT, n=1) and liver transplantation (n=1). We obtained a median of 54 million paired-end reads (range: 29-296 million) using massively parallel bisulfite sequencing. There was a median of 201,499 donor-specific informative SNP loci (range: 14,091-328,861) for which the recipient was homozygous (i.e. AA) and the donor was heterozygous (i.e. AB) or for which both recipient and donor were homozygous but in different genotype (i.e. AA vs. BB), allowing for defining donor-specific alleles. There was a median of 195,475 recipient-specific informative SNP loci (range: 2,913-334, 122) for which the recipient was heterozygous (i.e. AB) and the donor was homozygous (i.e. AA) or for which both recipient and donor were homozygous but in different genotype (i.e. AA v.s. BB), allowing for defining recipient-specific alleles. Urinary DNA molecules that carried the recipient- and donor-specific alleles were deemed as recipient-derived and donor-derived urinary DNA molecules. The median donor DNA fraction among those samples was 32.9% (range: 2.5%-94.0%). The JI-U patterns for the recipient-derived and donor-derived DNA molecules in urine were deduced respectively for each sample according to the embodiments in this disclosure.

Figures 13A, 13B, 13C:
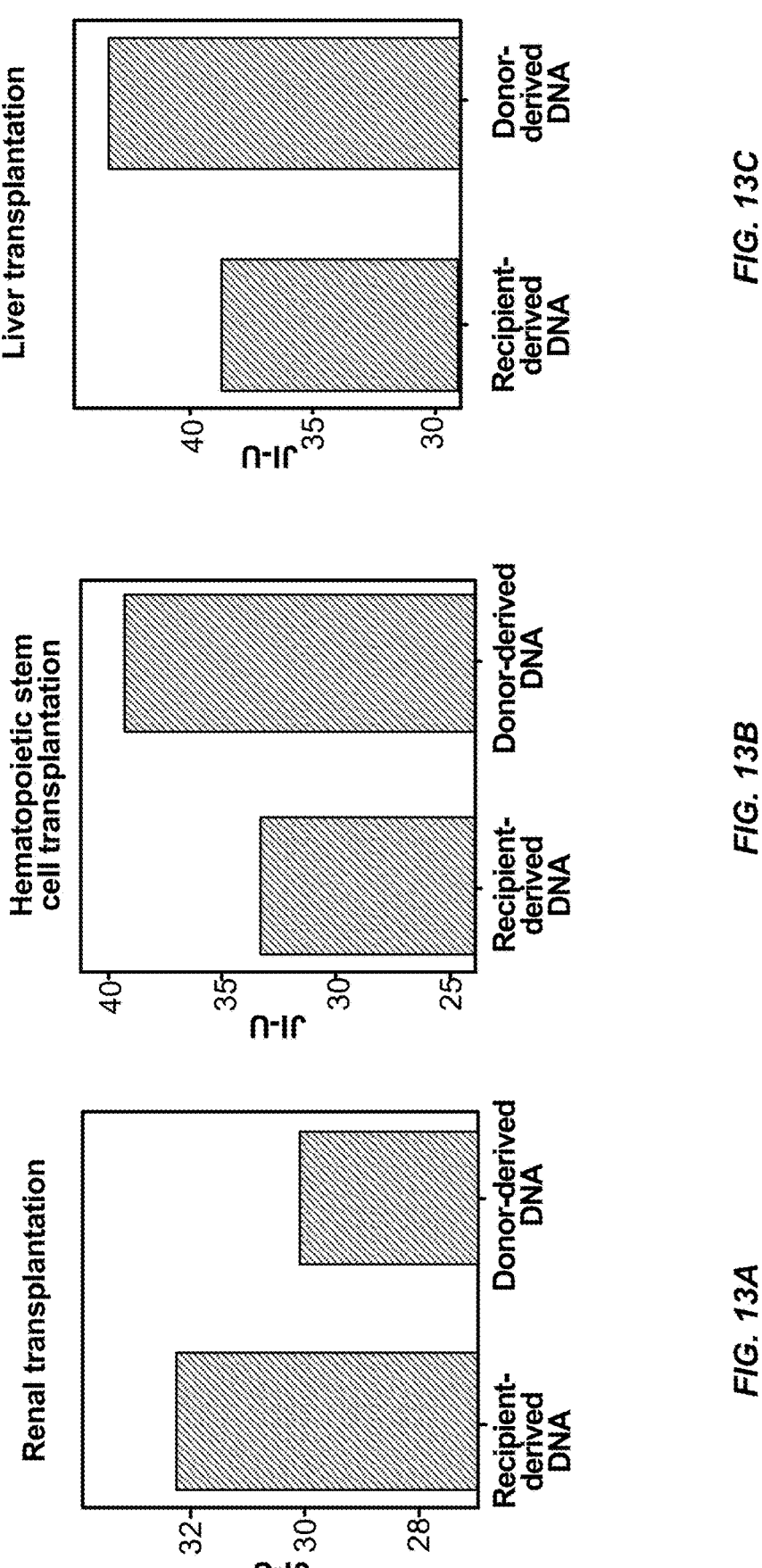
FIGS. 13A, 13B, and 13C show JI-U values between recipient- and donor-derived DNA in patients with renal transplantation, hematopoietic stem cell transplantation (HSCT), and liver transplantation according to embodiments of the present invention.

FIGS. 13A, 13B, and 13C show JI-U values between recipient- and donor-derived DNA in different transplant patients. FIG. 13A shows patients with renal transplantation. FIG. 13B shows patients with hematopoietic stem cell transplantation (HSCT). FIG. 13C shows patients with liver transplantation. The y-axis of each of the three figures shows the JI-U. The x-axis of each of the three figures shows recipient-derived DNA and donor-derived DNA.

FIG. 13A shows a 6.5% decrease of JI-U in the donor DNA (median: 30.1) compared with the recipient DNA (median: 32.2) in the urine of patients with renal transplantation. By contrast, FIG. 13B and FIG. 13C show increases of JI-U in donor DNA.

FIG. 13B shows a 17.6% increase of JI-U in the donor DNA (JI-U: 39.3) compared with the recipient DNA (JI-U: 33.4) in HSCT.

FIG. 13C shows an increase of JI-U in the donor DNA (42.6) compared with the recipient DNA (38.7) in the urine of patients of liver transplantation (elevation: ~10.0%).

These results suggested that the transrenal DNA molecules may be characterized by greater jaggedness than the postrenal DNA molecules. Therefore, in one embodiment, one may use the jaggedness marker to enrich the transrenal DNA molecules by selectively analyzing the urinary DNA molecules with long jagged ends, thereby improving the performance of the monitoring of organ damages outside the urinary system (e.g. blood cells, liver, lung, and colon, etc.) using urinary DNA. The selective analysis may involve the in-silico and physical selections of desired urinary DNA molecules. Physical selections could include, but not limited to, magnetic bead-based hybridization assay mediated by DNA probes, gel electrophoresis, and microfluidics.

C. Example Enrichment Methods

FIG. 14 shows a method 1400 of enriching a biological sample obtained from an individual for clinically-relevant nucleic acid molecules. The biological sample may include a plurality of nucleic acid molecules. The plurality of nucleic acid molecules may be cell-free. The plurality of nucleic acid molecules may include the clinically-relevant nucleic acid molecules and other nucleic acid molecules. Each nucleic acid molecule of the first plurality of nucleic acid molecules may be double-stranded with a first strand having a first portion and a second strand. The first portion of the first strand of at least some of the plurality of nucleic acid molecules may have no complementary portion from the second strand. The first portion may not be hybridized to the second strand. The first portion may be at a first end of the first strand. The first portion may overhang the second strand. The clinically-relevant nucleic acid molecules may include may include fetal DNA, tumor-derived DNA, transplant DNA, or DNA associated with a disorder.

At block 1402, a subset of nucleic acid molecules within the first plurality of nucleic acid molecules may be selected. For each nucleic acid molecule of the subset of nucleic acid molecules, a length of the first strand that overhangs or is not hybridized to the second strand may be greater than a threshold value. The length of the first strand may overhang the second strand. The subset of nucleic acid molecules may include fewer nucleic acid molecules than the plurality of nucleic acid molecules.

In some embodiments, selecting the subset of nucleic acid molecules may include measuring a characteristic of the first strand and/or second strand. The characteristic may correlate to (e.g., be proportional to) the length of the first strand that overhangs or is not hybridized to the second strand for each nucleic acid molecule of the plurality of nucleic acid molecules. The characteristic may be proportional to the length of the first strand that overhangs the second strand. The characteristic may be any characteristic described herein, including the length of the first strand that overhangs or is not hybridized to the second strand. Identifying the subset of nucleic acid molecules may include selecting, by a computer system, nucleic acid molecules having the characteristic greater than a cutoff value to obtain the second plurality of nucleic acid molecules. The cutoff value may be a minimum length of an overhang. For example, the minimum length may be 1, 2, 3, 4, 5, 6, 7, 8, 9, 10, 10 to 15, 15 to 20, or greater than 20 nucleotides.

In some embodiments, selecting the subset of nucleic acid molecules may include a physical selection of molecules with a minimum length of overhang. Selecting the subset of nucleic acid molecules may include physically separating the subset of the nucleic acid molecules from the rest of the plurality of nucleic acid molecules. For example, methods may include hybridizing an oligonucleotide to the length of the first strand for each nucleic acid molecule of the first plurality of nucleic acid molecules. A characteristic of the oligonucleotide may be measured. The characteristic of the oligonucleotide may be proportional to the length of the first strand that overhangs or is not hybridized to the second strand. Nucleic acid molecules having the characteristic greater than a cutoff value may be selected to obtain the second plurality of nucleic acid molecules. The oligonucleotide may include a fluorescent marker or markers. The characteristic may be fluorescence. Oligonucleotides may be sorted based on the fluorescence. In some embodiments, the physical selection may include magnetic bead-based hybridization assay mediated by DNA probes, gel electrophoresis, and microfluidics.

Unlike other hybridization-based capture enrichment techniques, the hybridization techniques would not involve denaturing double-stranded DNA to form single-stranded DNA in order to facilitate hybridization to an oligonucleotide. The jagged end of a double-stranded DNA molecule is already single-stranded DNA, and denaturing a double-stranded DNA molecule with a jagged end may make determining the length of the jagged end more difficult.

In some embodiments, the oligonucleotide may be attached to a marker for oligonucleotides above a cutoff length. The method may include capturing nucleic acid molecules having the marker to obtain the second plurality of nucleic acid molecules. The marker may include biotin or other molecule that has a structure that can be selectively captured. The nucleic acid molecules may be captured by binding the marker. The captured nucleic acid molecules may be amplified to obtain an amplified subset of nucleic acid molecules.

The amplified subset of nucleic acid molecules may represent genomic regions having more jagged ends than other regions. As examples, a genomic region that generates more molecules with longer jagged ends in subjects with cancer (e.g., bladder cancer) than subjects without cancer may be identified. A probe targeting long jagged ends (e.g., longer than 10 nt) may be designed. The probes may preferentially bind long jagged ends over shorter jagged ends. Probes being longer than a certain length are difficult to hybridize to jagged ends shorter than the certain length. In addition, even if a probe were able to hybridize to a shorter length, the affinity between the probe and the shorter end is lower than between the probe and a longer length. As a result, the hybridized probe and shorter jagged end may not be stable and at certain temperatures (such as an incubation temperature), the hybridization may denature.

Various hybridization assays may be used. The hybridization may be accomplished in either a liquid solution or on a solid support. With a liquid solution, the assay may be followed by a separation step to isolate the hybrid product. The separation step may involve magnetic particles in magnetic fields. Magnetic beads coated with streptavidin may selectively collect the targeted long jagged ends. In some embodiments, absorption chromatography, differential precipitation, electrophoresis, affinity chromatography, or immunoprecipitation may be used for separation. With a solid support, the support may include polymer beads, glass slides, columns with resin, or a membrane. The tagged long jagged ends may be attached to the support substrate, and the non-binding fragments may be washed away (e.g., using fluidics).

At block 1404, the subset of nucleic acid molecules may be analyzed to determine a property of the clinically-relevant nucleic acid molecules. In some embodiments, analyzing the subset of nucleic acid molecules may include using the amplified subset of nucleic acid molecules.

Analyzing the subset of nucleic acid molecules may include determining a value of a parameter using the second plurality of nucleic acid molecules. Determining the value of the parameter may use the amplified subset of nucleic acid molecules. The parameter may be a statistical measure of a size profile, including mean, median, mode, percentile, minimum, or maximum. In some embodiments, the value of the parameter may be an amount of nucleic acid molecules. In some embodiments, the value of the parameter may be determined using the amount of nucleic acid molecules in certain regions. For example, the amount of nucleic acid molecules may be used to determine a number of copy number aberrations, including deletions and amplifications.

A classification of a level of a condition using the value of the parameter may be determined. Determining the classification of level of the condition may include comparing the value of the parameter to a reference value. The level of the condition may be classified as being present, likely, or severe when the value of the parameter exceeds the reference value. The reference value may be any reference value described herein. The condition may include a disease, a disorder, a pregnancy, or a transplant status. The condition may include a cancer, an auto-immune disease, a pregnancy-related condition, or a transplant rejection. The condition may include any condition described herein. The method may further include treatment following classifying that a condition exists or is severe. The treatment may include any treatment described herein.

The classification of a condition may also be based on other clinical factors. For example, an individual may be considered to be at risk of a particular condition because of genetic factors or because of age. In some examples, the individual may be exhibiting symptoms of the condition.

In some embodiments, the classification can be performed using a machine learning model, e.g., as described for block 606 of FIG. 6.

VI. Transplant Conditions

We further analyzed two renal transplant samples (RT01 and RT02), with 72 and 79 million paired reads, respectively. The donor DNA fraction was found to be 32.9% and 53.2% for RT01 and RT02, respectively.

Figure 15:
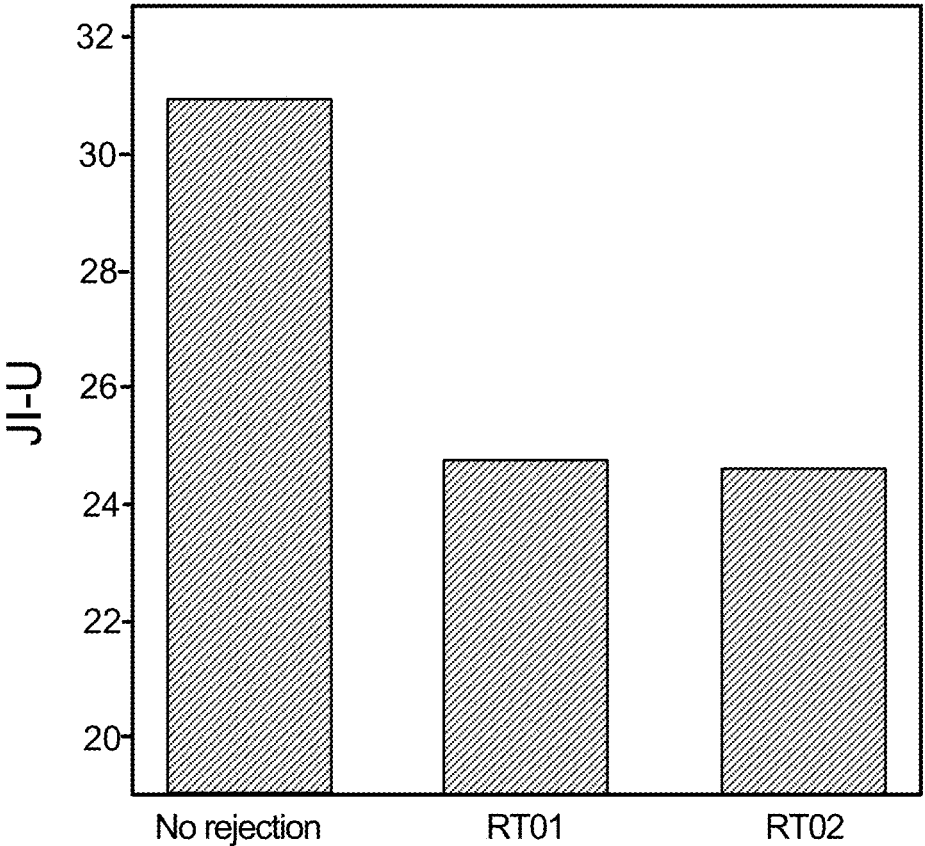
FIG. 15 shows JI-U values of urinary DNA between renal transplant patients with and without acute rejection according to embodiments of the present invention.

FIG. 15 shows JI-U values of urinary DNA between renal transplant patients with and without acute rejection. The y-axis shows the JI-U values. The x-axis shows the categories for the different samples: a sample with no rejection and the two renal transplant samples (RT01 and RT02).

As shown in FIG. 15, we observed a 20.0% decrease of JI-U in the renal transplant patient RT01 with acute rejection (JI-U: 24.7) in comparison with the 10 renal transplant patients without rejection (JI-U median: 30.9). We observed a 20.4% decrease of JI-U in the renal transplant patient RT01 with acute rejection (JI-U: 24.6) in comparison with the 10 renal transplant patients without rejection (JI-U median: 30.9). These data suggested that one could use the JI-U of urinary DNA molecules to monitor the patients with organ transplantations.

Based on FIG. 13B and FIG. 13C showing higher JI-U values for donor-derived DNA than recipient-derived DNA, we expect that HSCT and liver transplantation rejection samples have higher JI-U values than samples with no rejection.

FIG. 16 shows a method 1600 of analyzing a biological sample obtained from an individual. The individual may be a recipient of a transplant of a first tissue. The transplanted first tissue may be from a kidney, a hematopoietic stem cell, or a liver. In some embodiments, the transplanted tissue may be from an organ, including a heart, lung, pancreas, or intestine. The transplanted tissue may be transplanted with the organ. In some embodiments, the transplant may include cornea, skin, blood, bone, or a limb.

The biological sample may include blood, plasma, urine, or saliva or may be any biological sample disclosed herein. The biological sample may include a plurality of nucleic acid molecules. The plurality of nucleic acid molecules may be cell-free. Each nucleic acid molecule of the plurality of nucleic acid molecules may be double-stranded with a first strand having a first portion and a second strand. The first portion of the first strand of at least some of the plurality of nucleic acid molecules may have no complementary portion from the second strand. The first portion may overhang or may not be hybridized to the second strand. The first portion may be at a first end of the first strand.

At block 1602, a characteristic of the first strand and/or the second strand may be measured for each nucleic acid molecule of the plurality of nucleic acid molecules. The characteristic may correlate to (e.g., be proportional to) a length of the first strand that overhangs or is not hybridized to the second strand. The characteristic may be any characteristic described herein, including a length of the jagged end.

At block 1604, a jagged index value using the measured characteristics of the plurality of nucleic acid molecules may be determined. The jagged index value may provide a collective measure of the length of a strand that overhangs or is not hybridized to another strand in the plurality of nucleic acid molecules. The jagged index value may be a jagged end value (e.g., jagged index-unmethylated [JI-U]). The jagged index value may be any jagged index value described herein, including a statistical value of the lengths of jagged ends of the plurality of nucleic acid molecules.

The jagged index value may be compared to a reference value. The reference value may be determined using one or more reference samples of subjects that rejected a transplant. In some embodiments, the reference value may be determined using one or more reference samples of subjects that did not reject a transplant. The reference value may be determined using one or more reference samples obtained from the individual before the biological sample is obtained from the individual. For example, the reference value may be determined from one or more reference samples obtained before the individual received the transplant. As another example, the reference value may be determined from one or more reference samples obtained from the individual after the transplant but before the current biological sample. The jagged index value may be monitored in a recipient of a transplant over time, with a past jagged index value serving as a reference value.

At block 1606, a transplant condition of the first tissue transplanted into the individual may be determined using the jagged index value. The determination may be based on the comparison of the jagged index value to the reference value. The transplant condition may include a likelihood of rejection, graft dysfunction, or infection. In some embodiments, the transplant condition may be classified as rejected, likely to be rejected, having a graft dysfunction, likely to have a graft dysfunction, infected, or likely to be infected when the jagged index value is greater than the reference value. For example, the first tissue may be one or more hematopoietic stem cells or from a liver. In other embodiments, the transplant condition may be determined as rejected, likely to be rejected, having a graft dysfunction, likely to have a graft dysfunction, infected, or likely to be infected when the jagged index value is less than the reference value. For example, the transplant may be from a kidney.

The transplant condition may be determined as the transplant is being rejected or likely to be rejected. The method may include treating the individual for an acute rejection of the transplant. For example, the transplant may be removed from the individual. In some embodiments, the individual may be administered immunosuppressant drugs. In some embodiments, the individual may be treated with antibodies, blood transfer, bone marrow transplant, or gene therapy.

In some embodiments, the determination can be performed using a machine learning model, e.g., as described for block 606 of FIG. 6.

VII. Differential Jaggedness Around Genomic Sites

We further investigated if the jagged ends were related to nucleosomal structures. Jagged ends were studied based on their position relative to sites that may be associated with a modification of a protein in chromatin at the genomic site or a protein interaction at the genomic site. We first identified genomic regions in which there were a series of well-ordered nucleosomes, called the nucleosomal arrays. For example, the nucleosome positioning in genomic regions near CTCF (a transcription factor encoded by the CTCF gene) binding sites was known to be well-organized (Snyder et al. Cell. 2016; 164:57-68; Sun et al. Genome Res. 2019; 29:418-27). We analyzed the jaggedness of urinary and plasma DNA within 1-kb up-/downstream relative to CTCF binding sites. We calculated the occurrence of plasma DNA ends (i.e., end density) around the CTCF binding sites. The end density was the value of end occurrence normalized by the median of those values across loci spanning 1-kb up-/downstream relative to CTCF binding sites. Fragment end signals were differentially phased around open chromatin regions (Sun et al. Genome Res. 2019; 29:418-27), when one separately analyzed ends according to the orientations of the upstream and downstream ends (i.e. U-end and D-end) of plasma DNA fragment in relation to the reference genome. In other words, after aligning sequenced fragments to the human reference genome, the U-end of a fragment represented the end with a smaller value in the genome coordinate, while D-end represented the end with a bigger value in the genome coordinate (Sun et al. Genome Res. 2019; 29:418-27).

In addition to position relative to CTCF sites, jaggedness was seen to vary relative to other sites, including histone modifications and DNASE1 hypersensitive sites (DHS). Jagged index values for DNA fragments at certain locations relative to these sites can be used to determine the level of a condition, such as cancer.

A. Results Showing Differences in Jaggedness at Particular Sites

Figure 17A:
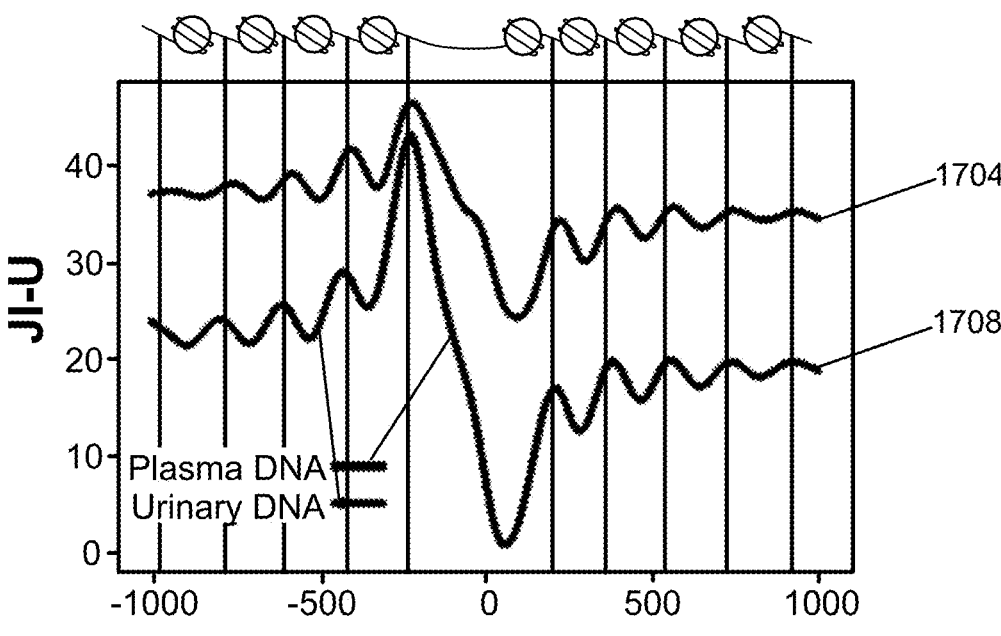
FIGS. 17A and 17B show relationships between jagged ends and nucleosome tracks according to embodiments of the present invention.
Figure 17B:
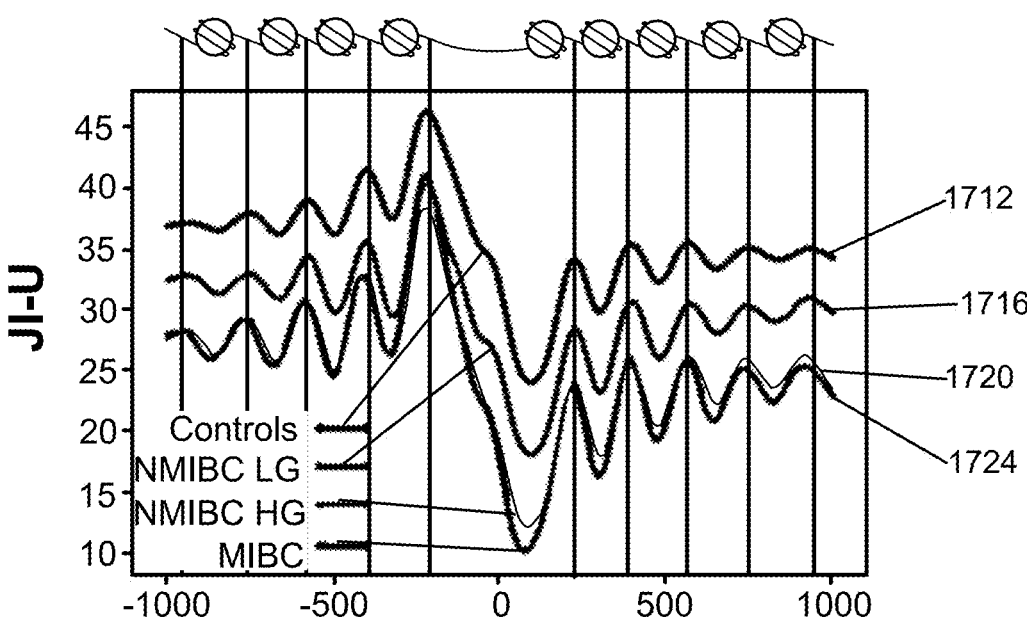

FIGS. 17A and 17B show the relationship between jagged ends and nucleosome tracks.

FIG. 17A shows JI-U values surrounding CTCF binding sites for pooled plasma and urinary DNA molecules derived from the Watson strand in non-cancerous subjects. The y-axis is the plasma DNA end density. The x-axis is the distance in base pairs from a CTCF binding site. Line 1704 represents urinary DNA. Line 1708 represents urinary DNA. Interestingly, JI-U signals of urinary DNA with respect to CTCF binding sites were also phased into patterns of nucleosomal arrays deduced from end density. The peak positions of JI-U signals were approximately aligned to the linker DNA regions, suggesting that the linker DNA cutting by DNA nucleases would be possibly accompanied with the generation of jagged ends. Such nucleosomal patterns of JI-U signals were also observed in plasma DNA molecules derived from the Watson strand. However, the amplitudes of urinary DNA JI-U waves near CTCF (median: 35.4) were higher than that of plasma DNA (median: 20.2) for control samples, whereas there is no appreciable difference in locations of periodicities between urinary and plasma DNA JI-U signals.

FIG. 17B shows JI-U values surrounding CTCF binding sites for urinary DNA molecules derived from the Watson strand in control subjects and patients with different stages of bladder cancer. The y-axis is the plasma DNA end density. The x-axis is the distance in base pairs from a CTCF binding site. The different lines show control subjects with hematuria but without bladder cancer (line 1712), low-grade non-muscle invasive bladder cancer (NMIBC LG) (line 1716), high-grade non-muscle invasive bladder cancer (NMIBC HG) (line 1720), and muscle invasive bladder cancer (MIBC) (line 1724). As shown in FIG. 17B, JI-U values nearby CTCF were also found to be lower in the urinary DNA of patients with bladder cancer and typically lowest in those with MIBC and high-grade NMIBC, compared with patients without bladder cancer. The patterns of JI-U values measured by cell DNA molecules derived from the Watson strand may be mirrored by those values from the Crick strand. These results suggested that JI-U values along the nucleosome structures could be used for cancer detection.

As described above, FIG. 7B shows JI-U values for both plasma DNA and urinary DNA relative to the distance for a nucleosomal center. JI-U values were observed to be higher for urinary DNA compared to plasma DNA for the same distance to a nucleosomal center.

To further validate whether the jagged ends would preferentially occur in nucleosomal linker DNA regions, we calculated the JI-U values using fragments relative to centers of each nucleosome track. The nucleosome tracks (1,037, 961 regions) were obtained from a previously published study (Gaffney et al. PLoS Genet. 2012; 8:e1003036).

B. Accuracy in Differentiating Condition Using Jaggedness at CTCF Sites

Figure 18:
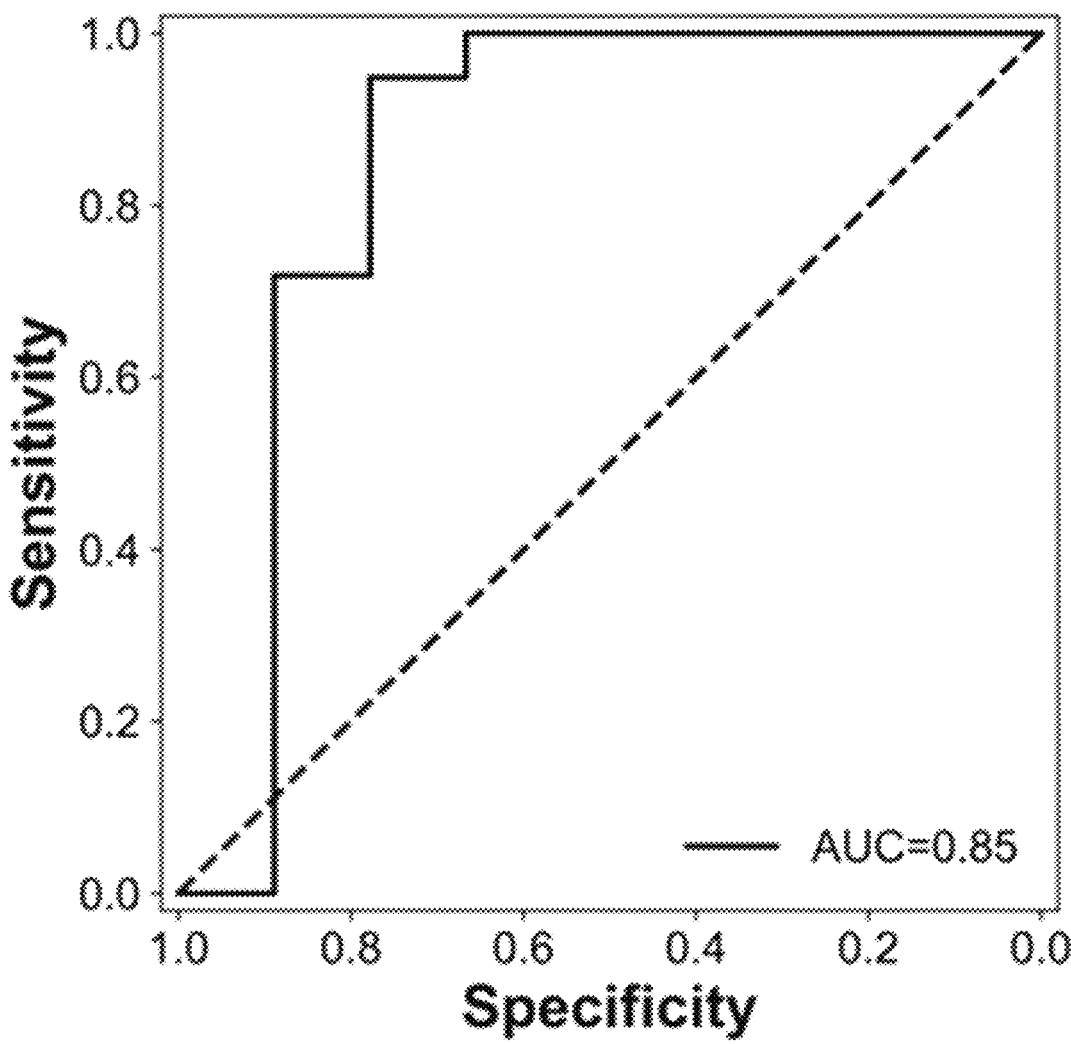
FIG. 18 shows a receiver operating characteristic (ROC) plot for differentiating between patients with MIBC and patients without bladder cancers according to embodiments of the present invention.

FIG. 18 shows an ROC plot for differentiating between patients with MIBC and patients without bladder cancers using the accumulated JI-U values of JI-U for positions ranging from 0 to 500 relative to CTCF sites. Sensitivity is show on the y-axis. Specificity is shown on the x-axis. The accumulated JI-U values of JI-U along the positions ranging from 0 to 500 relative to CTCF sites in FIG. 17B achieved an AUC of 0.85 in differentiating between patients with MIBC and patients without bladder cancers. These results demonstrate that JI-U values of urinary DNA along the nucleosome structures may be used for cancer detection.

C. Accuracy in Differentiating Condition Using Jaggedness at Regions with Histone Modifications Jaggedness at particular regions may be used for cancer detection. Particular histone modifications may be used, including, for example, H3K4me1, H3K4me3, H3K36me3, H3K27me2, H3K9Ac, H3K27Ac, H4K16Ac, H3K27me3, and H3K9me3. H3K4me1 and H3K4me3 are analyzed. H3K4me1 is an epigenetic modification acting on the DNA packaging protein Histone H3, which involves the mono-methylation at the fourth lysine residue of the histone H3 protein. H3K4me1 was reported to be related to gene enhancers. H3K4me3 is an epigenetic modification acting on the DNA packaging protein Histone H3, which involved the tri-methylation at the fourth lysine residue of the histone H3 protein. H3K4me3 was reported to be related to activating gene expression.

Figure 19A:
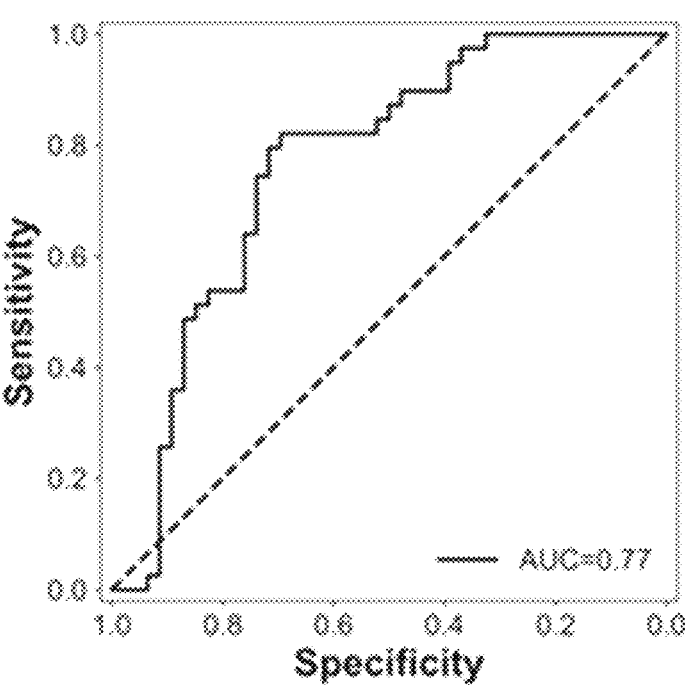
FIGS. 19A and 19B show results from analyzing urinary DNA jagged ends originating from the genomic regions associated with these histone modifications according to embodiments of the present invention.
Figure 19B:
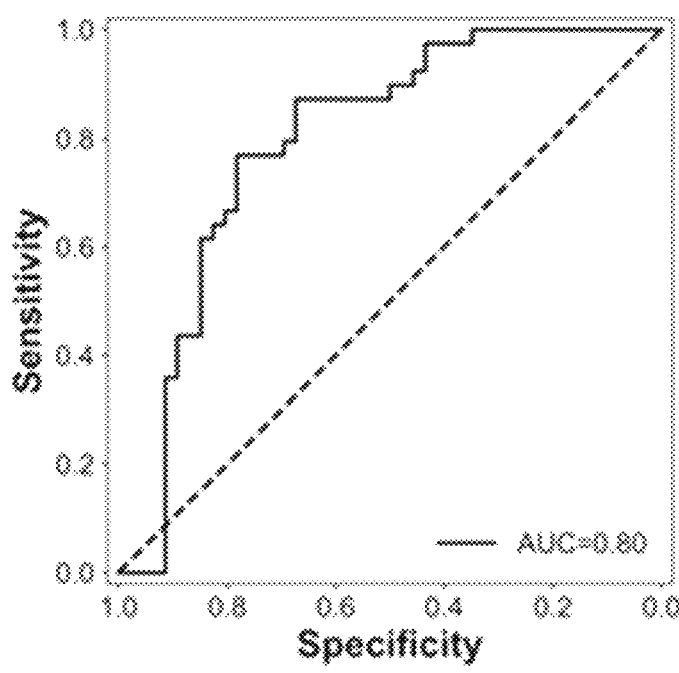

FIGS. 19A and 19B show results from analyzing urinary DNA jagged ends originating from the genomic regions associated with these histone modifications. FIGS. 19A and 19B show ROC plots for differentiating between patients with MIBC and patients without bladder cancers using the accumulated JI-U values. FIG. 19A shows results for using the genomic region associated with H3K4me1 histone modification. FIG. 19B shows results for using the genomic region associated with H3K4me3 histone modification. Sensitivity is shown on the y-axis in both graphs, and specificity is shown on the x-axis in both graphs. As seen from both figures, the JI-U values deduced from genomic regions marked by H3K4me3 gave rise to a better performance in differentiating the patients with bladder cancer from those without cancer (AUC: 0.80), compared with JI-U values associated with H3K4me1 (AUC: 0.77). This result suggested that selective analysis of jagged ends related to a particular epigenetic modification may enhance diagnostic power.

D. Example Methods

FIG. 20 shows a method 2000 of analyzing a biological sample obtained from an individual. The biological sample may be any biological sample described herein. The biological sample may include a plurality of nucleic acid molecules. The plurality of nucleic acid molecules may be cell-free. Each nucleic acid molecule of the plurality of nucleic acid molecules may be double-stranded with a first strand having a first portion at an end and a second strand. The first portion of the first strand of at least some of the plurality of nucleic acid molecules may have no complementary portion from the second strand. The first portion may not be hybridized to the second strand. The first portion also may be at a first end of the first strand. The first portion of the first strand may overhang the second strand.

At block 2002, the plurality of nucleic acid molecules may be sequenced to produce sequence reads. Sequencing may be by any technique disclosed herein.

At block 2004, the sequence reads may be aligned to a reference genome to determine genomic locations of the plurality of nucleic acid molecules. The reference genome may be a human reference genome.

At block 2006, a set of nucleic acid molecules of the plurality of nucleic acid molecules may be identified. Each nucleic acid molecule of the set of nucleic acid molecules may have a genomic location at a specified distance from a genomic site. The genomic site may be a predetermined type of site. The genomic site may be associated with a modification of a protein in chromatin at the genomic site or a protein interaction at the genomic site. The genomic site may be a CTCF binding site or a DNASE1 hypersensitive site (DHS). The genomic site may refer to a genomic region rather than being limited to a single genomic coordinate. In addition, the genomic site may include regions with particular histone modifications, such as H3K4me1, H3K4me3, H3K36me3, H3K27me2, H3K9Ac, H3K27Ac, H4K16Ac, H3K27me3, and H3K9me3. In some embodiments, the genomic site may be a nucleosomal center, an edge of nucleosome, or a region corresponding to a nucleosome. Identifying the set of nucleic acid molecules may include sequencing each nucleic acid molecule of the set of nucleic acid molecules to produce one or more reads. The sequencing may be performed in various ways, e.g., as described herein. Example techniques may use probes, sequencing by synthesis, ligation, and nanopores. The one or more reads may be aligned to a reference genome (e.g., a human reference genome). The genomic location of the nucleic acid molecule may be determined from the one or more reads.

The specified distance from the genomic site may be a range. For example, the range may be 0 to 40 nt, 40 to 70 nt, 70 to 100 nt, 100 to 130 nt, 130 to 160 nt, 160 to 190 nt, 190 to 200 nt, 200 to 250 nt, 250 to 300 nt, 300 to 350 nt, 350 to 400 nt, 400 to 500 nt, 500 to 750 nt, 750 to 1,000 nt, or greater than 1,000 nt. In some embodiments, the specified distance may be 0 nt.

At block 2008, a characteristic of the first strand and/or the second strand for each nucleic acid molecule of the set of nucleic acid molecules may be measured. The characteristic may correlate to (e.g., be proportional to) a length of the first strand that overhangs or is not hybridized to the second strand. The characteristic may be any characteristic described herein, including a directly determined length.

At block 2010, a jagged index value using the measured characteristics of the set of nucleic acid molecules may be determined. The jagged index value may provide a collective measure of the length of a strand that is not hybridized to another strand in the set of nucleic acid molecules. The jagged index value may be any jagged index value described herein, including a statistical value of the length of the jagged ends of the set of nucleic acid molecules.

The jagged index value may be compared to a reference value. The reference value may be determined from reference samples from subjects with the condition or without the condition. The reference value may be determined in any way described herein.

At block 2012, a level of a condition of the individual may be determined using the jagged index value. The determination may be based on a comparison of the jagged end value with the reference value. The condition may be any condition described herein. If the jagged index value exceeds the reference value, the condition may be determined to exist, be likely, or be severe. Methods may include treating the condition. The treatment may be any treatment described herein.

In some embodiments, the determination can be performed using a machine learning model, e.g., as described for block 606 of FIG. 6.

VIII. Jagged End Analysis Techniques without Trimming 3' Ends

The disclosure herein shows an abundance of single strand overhangs of cell-free DNA (cfDNA) are present not only in plasma, but also in urine. Our previous work has demonstrated that jagged end analysis by sequencing (Jag-seq) allows studying the characteristics of jagged ends, and we found evidence that jagged ends in plasma DNA could be used as a biomarker in molecular diagnostics (Jiang et al., 2020). However, there is a paucity of information regarding the molecular characteristics of jagged ends in urinary cfDNA. Therefore, we apply a modified version of Jag-seq (Jag-seq II) to urinary cfDNA to explore more about the nature of jagged ends, especially the length of jagged ends in urine and application of jagged end analysis in urinary DNA. The new version, Jag-seq II, unexpectedly allows for more accurate determination of jagged end lengths and more accurate determinations of levels of conditions resulting from analysis of jagged end lengths. Overhanging 5' ends are analyzing without treatments to trim overhanging 3' ends. Avoiding trimming the 3' ends increases the amount of overhanging 5' ends to be analyzed, particularly shorter 5' end overhangs.

A. Enzymatic Treatment for Examining Overhangs of cfDNA Molecules

Figure 21A:
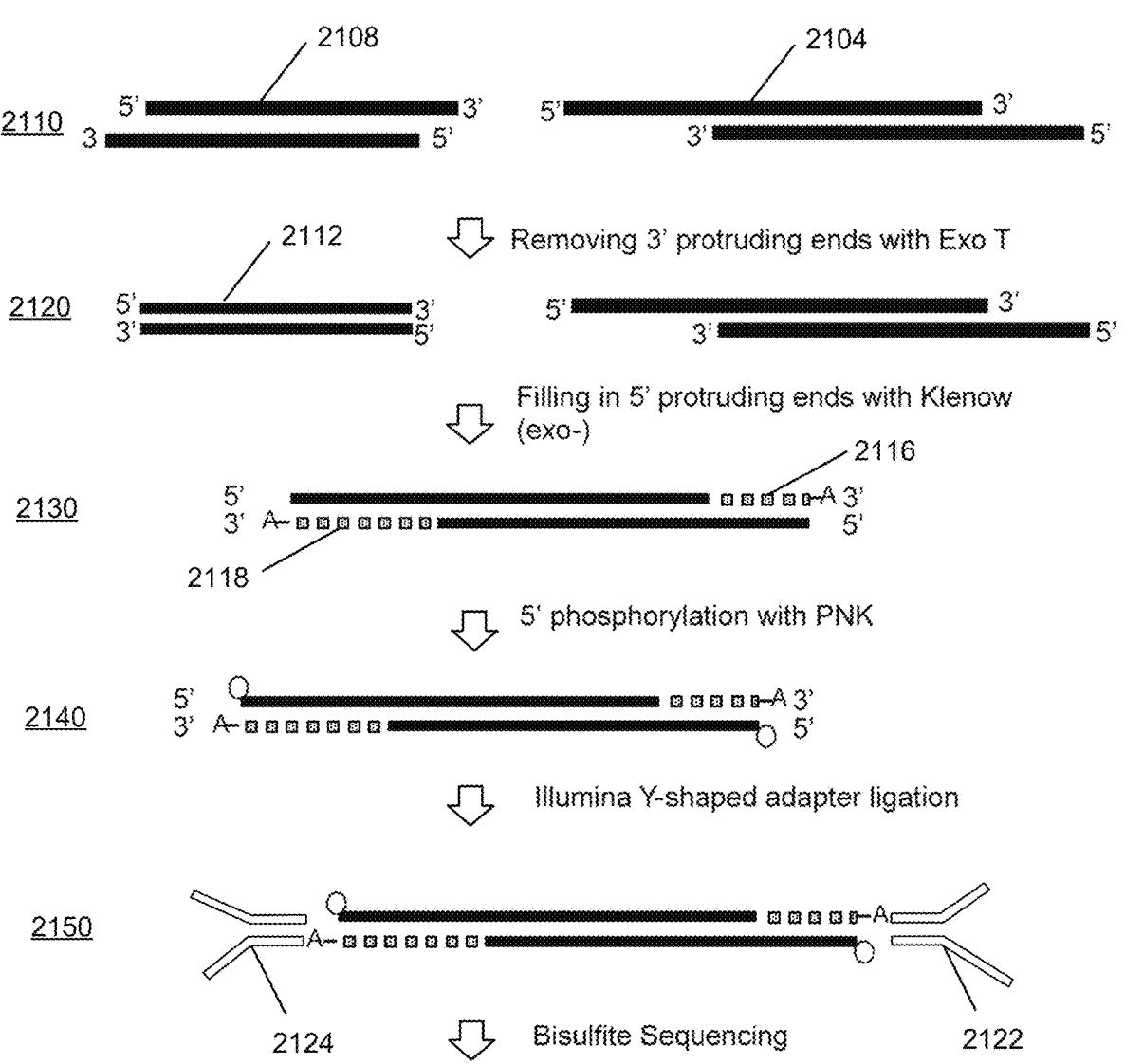
FIGS. 21A and 21B illustrate the previous Jag-seq method and the new Jag-seq II method according to embodiments of the present invention.

FIG. 21A shows the previous Jag-seq approach for determining lengths of jagged ends. The Jag-seq approach was mainly applied on determining the 5' protruding ends and blunt ends (e.g., fragment 2304). Stage 2110 shows fragment 2104 with a 5' protruding end, and fragment 2108 with a 3' protruding end. The cytosines in the fragments are mostly unmethylated.

Stage 2120 shows the fragments after 3' protruding ends are removed with Exo T, an exonuclease. Fragment 2108 becomes fragment 2112. Fragment 2104 is unaffected.

Stage 2130 shows the result of fragment 2104 after filling the 5' protruding ends with Klenow (exo-). The dashed lines (e.g., lines 2116 and 2118) represent the newly filled nucleotides of the blunt-ended fragment. The 3' ends in the 5' overhang molecules were filled by dATPs (As), dTTPs (Ts), dGTPs (Gs), and mdCTPs (mCs) to form blunt ends. Cytosines of the newly filled in nucleotides are methylated, while cytosines of the original fragment are unmethylated. The methylation difference between the newly filled in nucleotides and the original fragment allow for the methylation profile to indicate the length of the jagged ends. Fragment 2112 may still be in the sample but is no longer shown because the fragments do not affect later jagged end analysis.

Stage 2140 shows a blunt-ended fragment after 5' phosphorylation with PNK. Stage 2150 shows the blunt-ended fragment after ligation with sequencing adapters (e.g., adapters 2122 and 2124).

After stage 2150, the fragment may be followed with bisulfite treatment. Jagged end analysis may proceed as described with stage 120 in FIG. 1. Fragments that originally had a 3' overhang, such as fragment 2308, do not factor into the jagged end analysis as these fragments do not receive new nucleotides to fill in jagged ends.

Figure 21B:
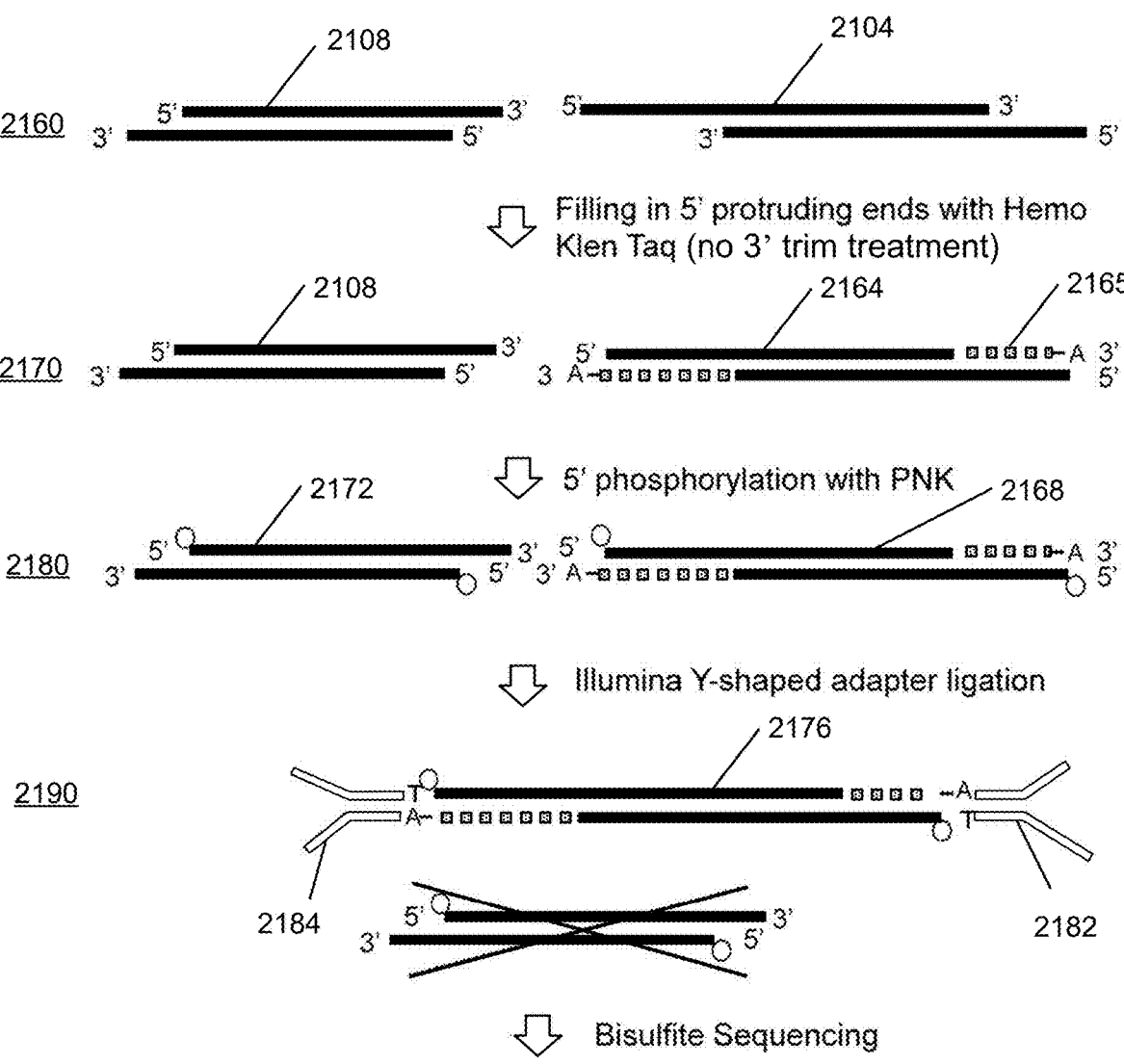

FIG. 21B shows an improved method, termed Jag-seq II, for jagged end detection to better understand the fragmentation of cfDNA. We refined the Jag-seq method by omitting a trim treatment step on the 3' protruding ends, which means the 3' protruding ends in 3' overhang molecules were not polished during the end repair procedure.

At stage 2160, both fragments with 5' protruding ends (fragment 2104) and 3' protruding ends (fragment 2108) are present. Stage 2160 may be equivalent to stage 2110. The fragments are then treated with Hemo Klen Taq to fill in the 5' protruding ends, but no 3' trim treatment is added.

Stage 2170 shows the fragments after the 5' protruding ends are filled in to form a blunt-ended fragment. Fragment 2104 becomes fragment 2164. The dashed lines correspond to the newly filled nucleotides of the blunt-ended fragment. Cytosines of the newly filled in nucleotides are methylated, while cytosines of the original fragment are unmethylated. In other embodiments, the newly filled in nucleotides may be unmethylated, while the nucleotides of the original fragment are methylated. Fragment 2108 remains unchanged.

Stage 2180 shows the fragments after 5' phosphorylation with PNK. Fragment 2164 is phosphorylated to become fragment 2168. Fragment 2108 is phosphorylated to become fragment 2172.

Stage 2190 shows fragments after ligation with sequencing adapters (e.g, adapters 2182 and 2184). The sequencing adapters are added to the blunt-ended fragment to become fragment 2176. Fragment 2176 can then undergo bisulfate sequencing and be analyzed for jagged ends as described with stage 120 in FIG. 1. Fragment 2172 is not blunt-ended, and sequencing adapters are not ligated to the fragment. As a result, fragment 2172 does not undergo bisulfite sequencing (denoted by the red X).

This improved approach would conserve the configuration of the protruding 3' ends without artificial alteration through enzyme trimming. This new approach achieves a more precise performance on jagged end length deduction than previous one, especially for the molecules containing short 5' protruding ends or blunt ends. The improvement with short 5' protruding ends is described in more detail below, where a few nucleotide errors in analysis of a protruding end makes a larger percentage difference in the length of the jagged end. Avoiding trimming 3' protruding ends would not artificially increase the count of blunt ends determined after bisulfite sequencing.

Figures 22A, 22B, 22C:
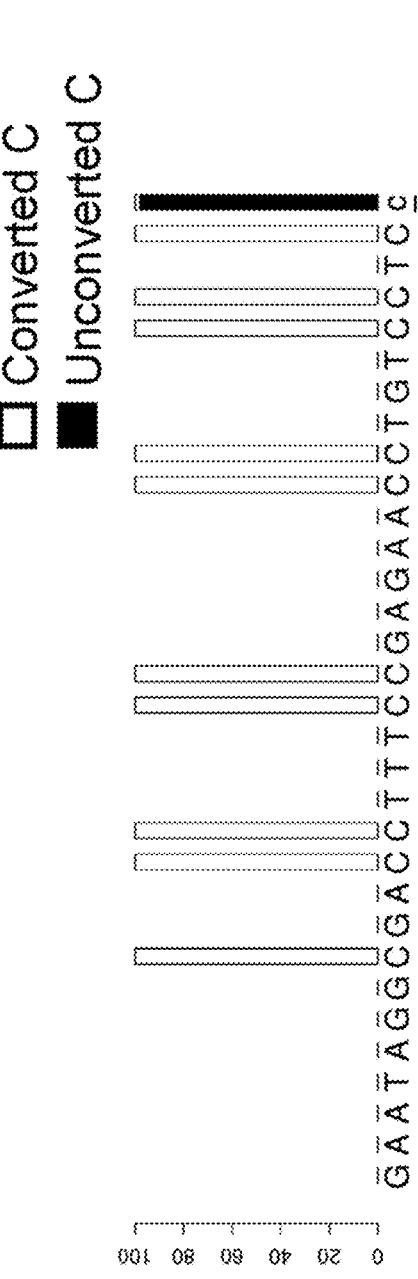
FIGS. 22A-22F illustrate the effects of using the Jag-seq and Jag-seq II techniques on spike-in molecules with 5' protruding jagged ends according to embodiments of the present invention.

FIGS. 22A-22F illustrate the effects of using the Jag-seq and Jag-seq II techniques on spike-in molecules with 5' protruding jagged ends. A spike-in DNA molecule is a DNA molecule of a known sequence. FIG. 22A shows the sequence structure of a 1 nt spike-in jagged end. FIG. 22B shows the sequence structure of a 14 nt spike-in jagged end. The bases in bold and underlined represent the 5' protruding ends.

The two molecules were designed to study if molecules containing shorter jagged ends would be affected more seriously by the 3' end trim step used in Jag-seq but not Jag-seq II. Both molecules include C nucleotide(s) at the 3' end of the strand hybridized to the strand with the 5' protruding end. FIG. 22A shows a single C nucleotide at the end.

Figure 22D:
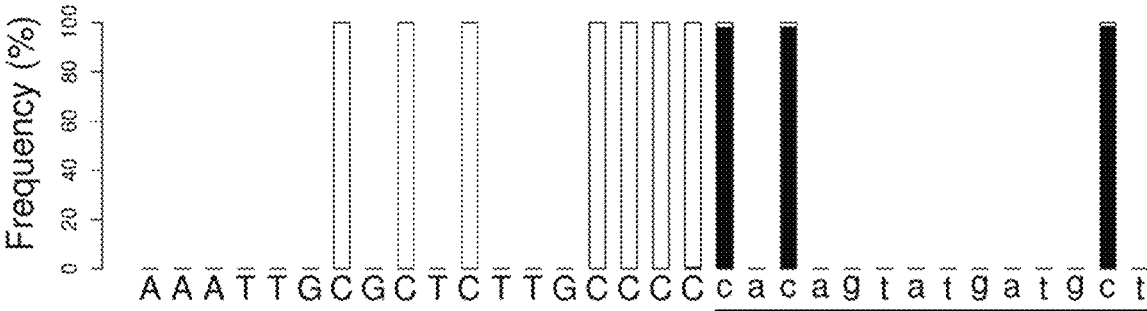

As shown in FIG. 22B, we designed the 46 bp molecule bearing a 14 nt 5' protruding end with four consecutive Cs at the end of 3' on the shorter strand. Additionally, the first overhang base of the longer strand is G, which enabled mC, the complementary base of G, to be incorporated as the first base during the end repair step. Therefore, through this special sequence base composition, we were able to detect any artificial jagged end created during library preparation. We added this molecule as an internal control during library preparation, as shown in FIG. 22D. This molecule allows us to confirm that the new sequencing protocol fills in jagged ends during the end repair process.

Figure 22E:
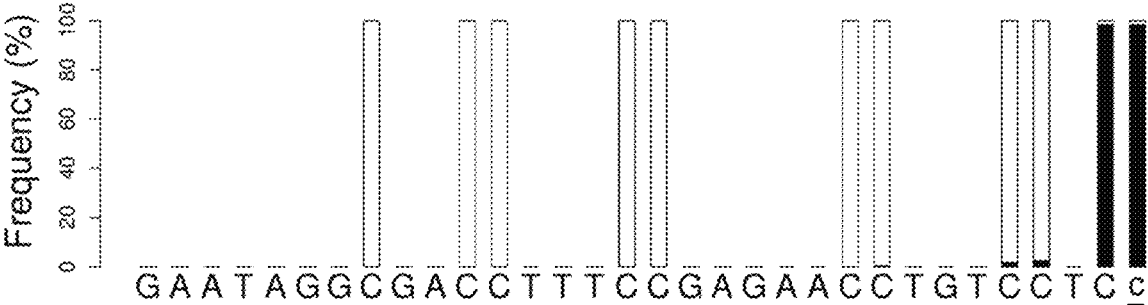
Figure 22F:
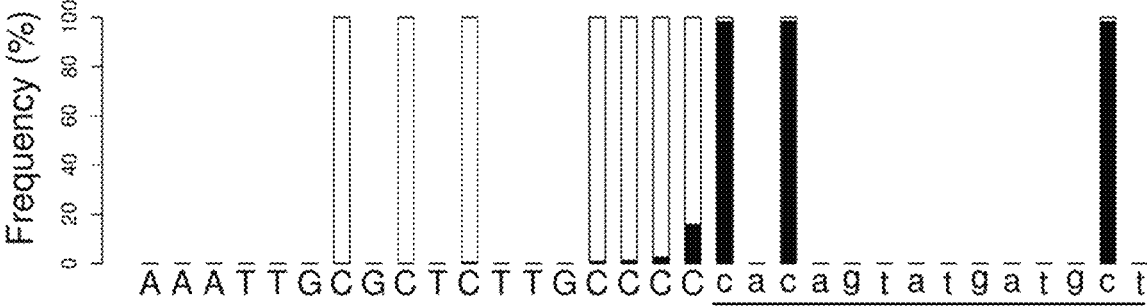

FIGS. 22C-22F show graphs of conversion of C for the spike-in sequences with known jagged ends. Cs that are added to fill in the jagged ends are methylated and are not converted to T. Cs that are part of the original molecule are unmethylated and are converted to T. The partial sequences of the spiked-in sequences with a 1 nt and a 14 nt jagged end are indicated on the x-axis. The nucleotides denoted in upper case alphabet indicate that the sequences are in double-stranded form. The nucleotides in lower cases alphabet and underlined indicate that the sequences are newly filled in during end repair. The shaded portion of a vertical bar indicates the frequency of T (converted C). The white portion of a vertical bar indicates the frequency of C (unconverted C). FIGS. 22C and 22D are results using the Jag-seq II technique. FIGS. 22E and 22F are results using the Jag-seq technique. Since we used methylated Cs in the incorporation step, the nucleotides corresponding to the original fragment before end repair should be converted C (i.e., T, denoted in gray), while the nucleotides corresponding to the nucleotides for end repair should be unconverted C (i.e., C, denoted in white).

As shown in FIG. 22D, with the Jag-seq II technique after bisulfite sequencing, we observed that 99.96% of the Cs located in the original double-stranded portion of the DNA molecule were converted to Ts, while 98.32% of the newly filled Cs (methylated) remained as Cs since we used methylated Cs in the incorporation step.

By contrast, as shown in FIG. 22F, 15.85% of the Cs at last base in the short strand was unconverted C (i.e., filled with mC before bisulfite treatment) in Jag-seq, which may potentially affect the accuracy on the jagged end length deduction or subsequent analysis with the jagged end lengths. The unwanted filling in of mC at the 3' shorter end on double strand was caused by the 3' end trim process in Jag-seq even though the 3' shorter end was not the protruding end. Compared to 15.85% of the Cs in the last base in the short strand that were unconverted C with Jag-seq in FIG. 22F, FIG. 22D shows that with Jag-seq II has significantly less unconverted C—only about 0.04% of the Cs in the last base in the short strand were unconverted C.

FIG. 22C shows that with the Jag-seq II technique, the C on last base of the double strand was only 0.19% unconverted. By contrast, FIG. 22E shows that with the Jag-seq technique the C on the last base was 98.23% unconverted. In other words, 99.81% of fragments were determined to be consistent with a length of 1-nt jagged end as originally designed with the modified Jag-seq II protocol while only 1.77% of fragments were determined to be consistent with a length of 1-nt jagged end with the previous Jag-seq protocol. These results indicated that the refined approach did not influence the nature of molecular ends, and we have thus successfully improved the accuracy of exact jagged end length deduction especially for the short 5' jagged ends. These improved accuracy results are surprising because the treatment to trim 3' overhang ends was not expected to affect the accuracy of fragments with a 5' overhang end.

B. Jagged End Index Values and Average Jagged End Length in Urinary cfDNA

The use of Jag-seq II in jagged end analysis was verified. Fragments in urine samples were analyzed for jagged end length and for methylation level, which is correlated with jagged end length.

Figure 23:
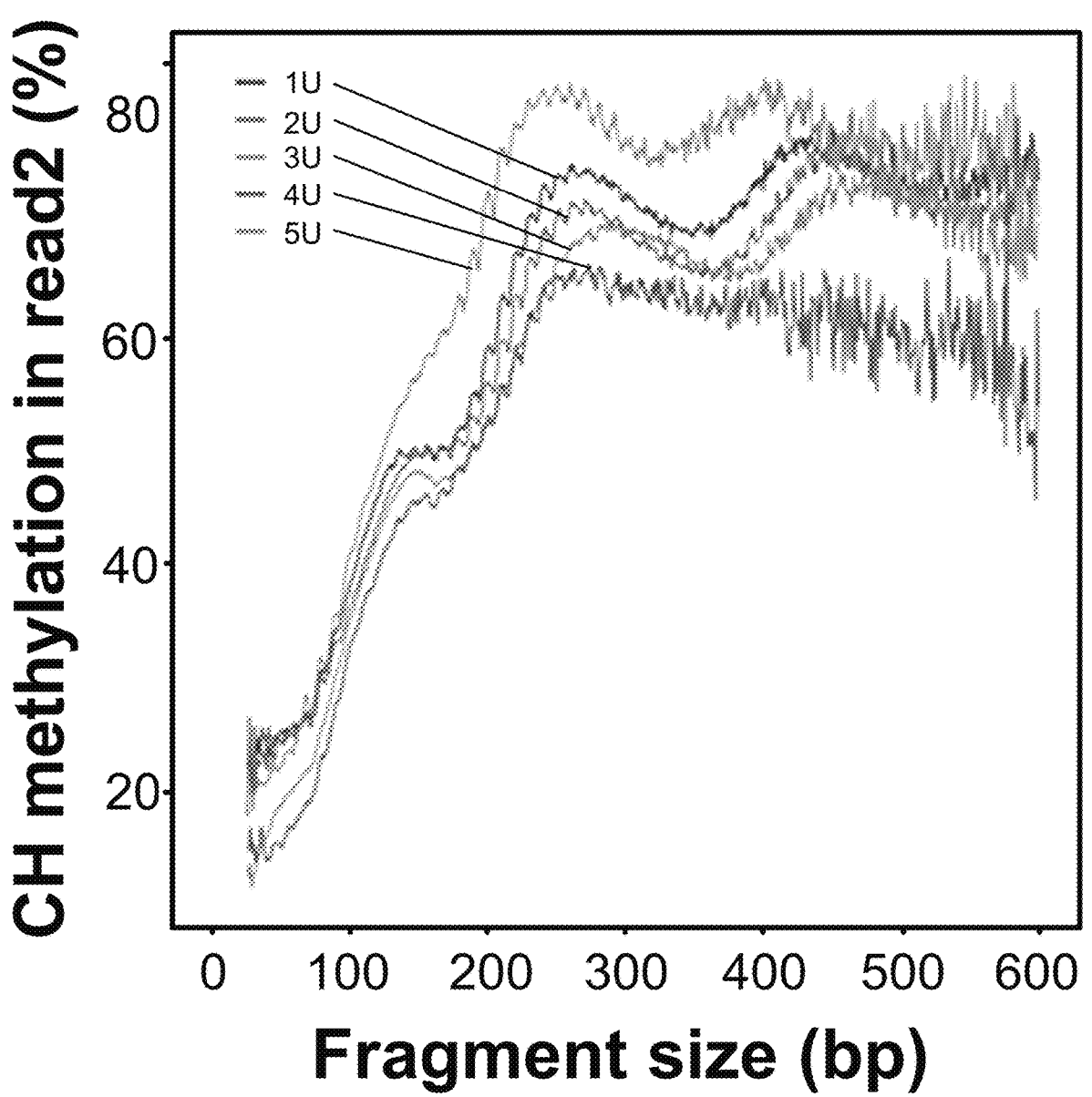
FIG. 23 shows a graph of the profile of CH methylation levels in read2 (JI-M) across different size ranges in urinary cfDNA according to embodiments of the present invention.

FIG. 23 shows a graph of the profile of CH methylation levels in read2 (JI-M) across different size ranges in urinary cfDNA using Jag-seq II. Here, CH methylation includes methylation of any C where H is A, C, or T but not where H is G. Read2 corresponds to the read including nucleotides added to fill in the 5' protruding end. With this figure, read2 includes the end 75 nucleotides. JI-M is Jagged Index-Methylated, which is the CH methylation level in read2. A higher JI-M indicates more methylation and a longer jagged end. The different lines represent different samples from different healthy individuals.

We conducted Jag-seq II on healthy urine samples to see the basic features of the urinary jagged ends. The y-axis shows CH methylation levels in read 2 (JI-M) as a percent. The x-axis shows the fragment size (bp). The different lines for 1 U to 5 U represent different healthy individuals. The value of JI-M varied across different sizes of molecules, showing wave-like patterns. The JI-M rapidly increased and reached a minor peak around 50% when the fragment size was around 130 bp. The JI-M continuously grew to the first major peak at 65%-80% near the molecule size of 240 bp. Subsequently, the second major peak appeared at approximately 410 bp fragment size.

Our previous study (Jiang et al., 2020) has found that the CC-tag strategy, which uses a methylated C next to an unmethylated C to infer the start of a jagged end, provided a solution to deduce the exact jagged end length. For example, the C at the very end of the 3' end of the original fragment may be methylated. The next nucleotide on the other strand with the 5' protruding end is a G. As a result, a newly added nucleotide to fill in the jagged end would be an unmethylated C. The pattern of a methylated C next to an unmethylated C then can identify the exact start of a jagged end. We examined average and median jagged end length under different molecular sizes and observed a similar wave-like pattern with that of JI-M.

Figure 24B:
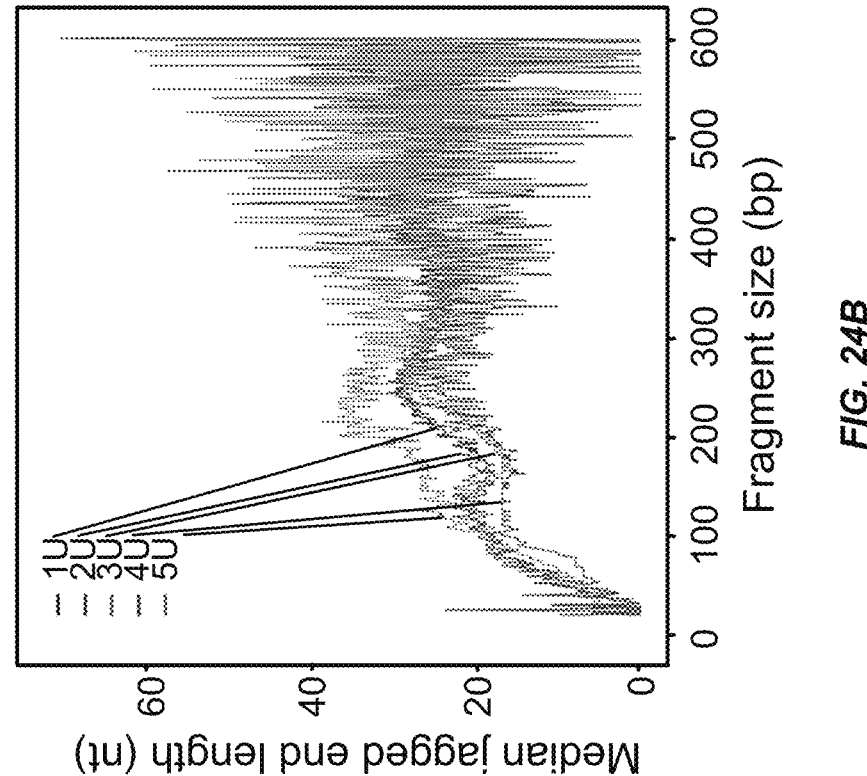
FIGS. 24A and 24B show the average and median jagged end length across different size ranges in urinary cfDNA according to embodiments of the present invention.
Figure 24A:
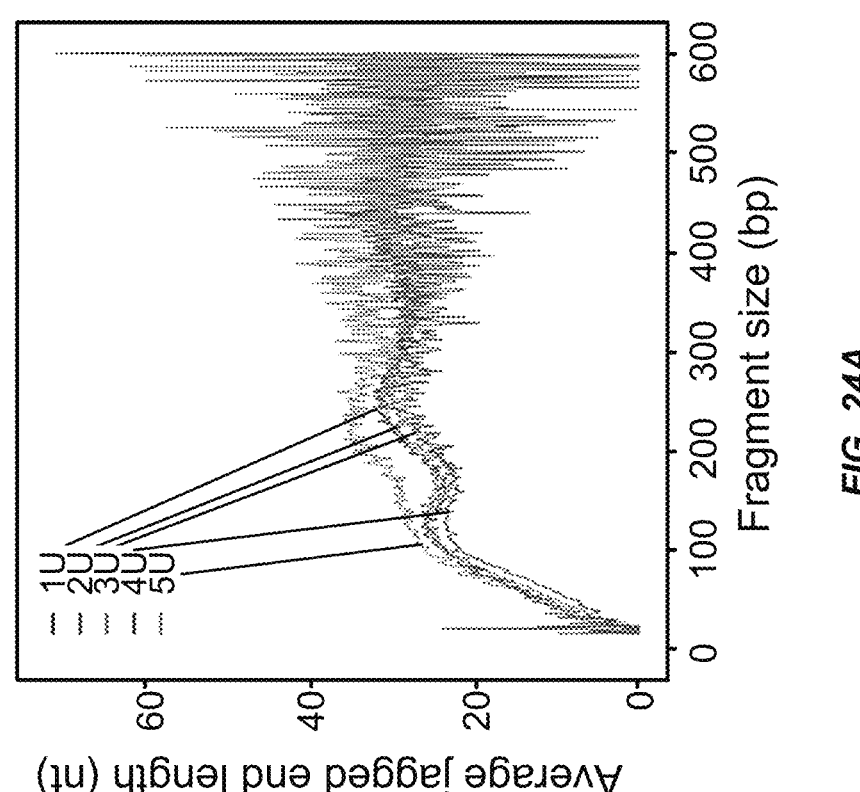

FIGS. 24A and 24B show the average and median jagged end length across different fragment sizes in urinary cfDNA. The x-axis shows the fragment size (bp) in both figures. The y-axis in FIG. 24A shows the average (mean) jagged end length. The y-axis in FIG. 24B shows the median jagged end length. The different lines for 1 U to 5 U represent different healthy individuals. Both graphs show wave-like patterns for the jagged end length. The distance between the two peaks is about 170 bp, which corresponds to nucleosome footprinting. These figures show that jagged end profiling may be used to determine and monitor nucleosome patterns.

C. Cancer Biomarker

To further examine whether the characteristics of jagged ends of urinary cfDNA could serve as a new biomarker to provide an additional field of cancer diagnosis, we applied Jag-seq II on urinary cfDNA of cancer patients.

Figure 25B:
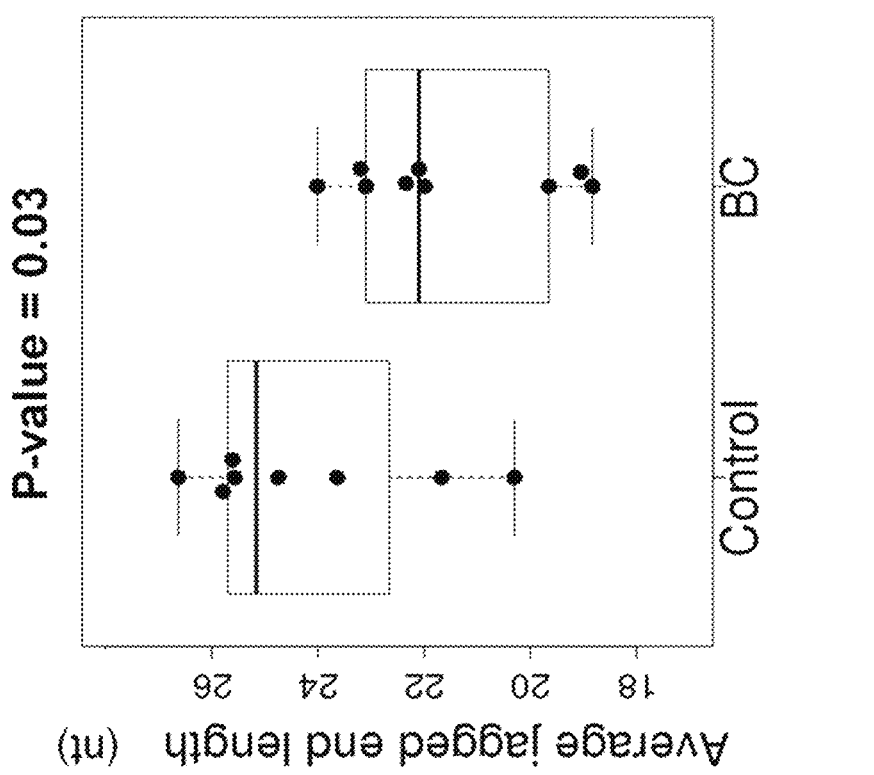
FIGS. 25A and 25B show box-and-whisker plots for JI-M and average jagged end lengths for bladder cancer subjects and for control subjects according to embodiments of the present invention.
Figure 25A:
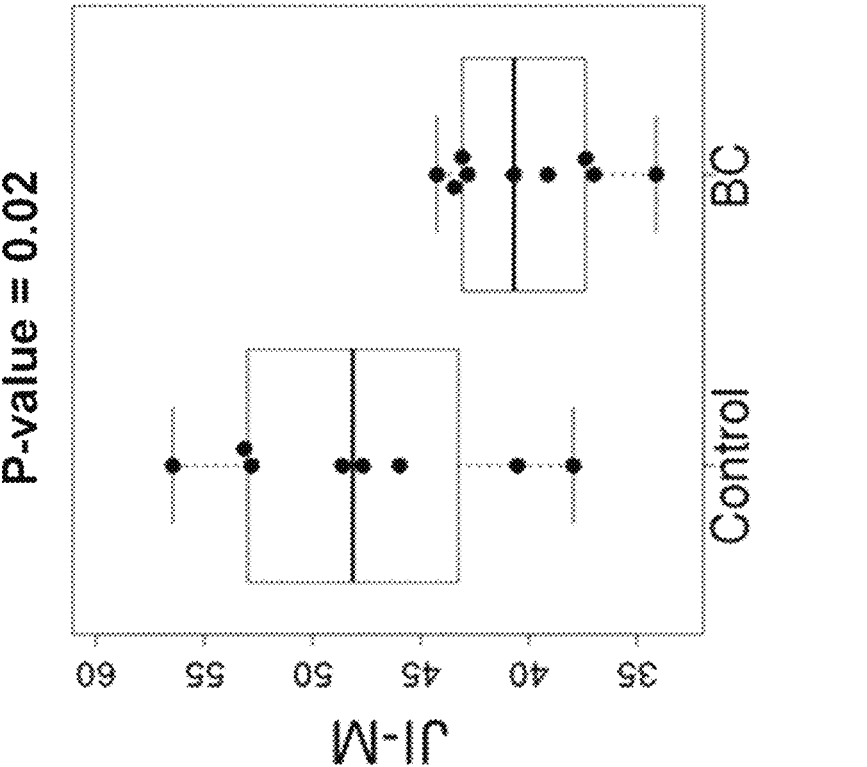

FIGS. 25A and 25B show box-and-whisker plots for JI-M and average jagged end lengths for bladder cancer patients and for control subjects. The average jagged end length is the mean value for all the lengths of jagged ends determined from CC-tags. The x-axis in the graphs show the control subjects and the bladder cancer patients. The y-axis in FIG. 25A shows the JI-M value. The y-axis in FIG. 25B shows the average jagged end length (nt). Clearly, both the JI-M and average jagged end length in bladder cancer patients (JI-M: median, 40.69; range, 34.11-44.25; average jagged end length: median, 22.10; range, 18.83-24.01) statistically decreased compared to those of healthy controls (JI-M: median, 48.14; range, 37.94-56.46; average jagged end length: median, 25.16; range, 20.30-26.63). The JI-M value or the average jagged end length is demonstrated to be a possible biomarker for bladder cancer.

D. Example Methods

FIG. 26 is a flowchart of an example process 2600 associated with analyzing a biological sample obtained from an individual without trimming 3' ends of fragments in the sample. In some implementations, one or more process blocks of FIG. 26 may be performed by a system (e.g., system 3400 in FIG. 34). In some implementations, one or more process blocks of FIG. 26 may be performed by another device or a group of devices separate from or including the system. Additionally, or alternatively, one or more process blocks of FIG. 26 may be performed by one or more components of system 3400, such as processor 3450, memory 3435, external memory 3440, storage device 3445, sample holder 3410, detector 3420, and/or logic system 3430.

The biological sample includes a first plurality of nucleic acid molecules, where the 5' end overhangs the 3' end. For example, the first plurality of nucleic acid molecules may include fragment 2104 in FIG. 21B. The first plurality of nucleic acid molecules may be cell-free. Each nucleic acid molecule of the first plurality of nucleic acid molecules is double-stranded with a first strand and a second strand. Each first strand includes a first portion not hybridized to the second strand. Each first portion is at a 5' end of the first strand. The biological sample may be any biological sample described herein.

The biological sample may include a second plurality of nucleic acid molecules, where the 3' end overhangs the 5' end. For example, the second plurality of nucleic acid molecules may include fragment 2108 of FIG. 21B. The second plurality of nucleic acid molecules may be cell-free. Each nucleic acid molecule of the second plurality of nucleic acid molecules is double-stranded with a third strand and a fourth strand (for terms different than the first strand and second strand for the first plurality of nucleic acid molecules). Each third strand includes a first portion not hybridized to the fourth strand. Each first portion is at a 3' end of the third strand. The biological sample may not include double-stranded nucleic acid molecules having a 3' end of one strand not hybridized to the other strand other than the nucleic acid molecules in the second plurality of nucleic acid molecules. In some embodiments, the second plurality of nucleic acid molecules includes at least 50%, 60%, 70%, 80%, 90%, or 95% of all nucleic acid molecules having an overhanging 3' end in the biological sample. In some embodiments, the number of the second plurality of nucleic acid molecules may be at least 50%, 60%, 70%, 80%, 90%, or 95% of the number of the first plurality of nucleic acid molecules. In some embodiments, the first plurality of nucleic acid molecules and/or the second plurality of nucleic acid molecules may be in a certain size range, including any size range described herein.

A first type of nucleotide in a nucleic acid molecule of the first plurality of nucleic acid molecules may all be methylated or may all be unmethylated. The first type of nucleotide may be cytosine or any nucleotide described herein. For example, in FIG. 21B, all cytosines in fragment 2104 of FIG. 21B may be methylated. In some embodiments, the first type of nucleotide in the nucleic acid molecule may be methylated or unmethylated above a certain percentage (e.g., 60%, 70%, 80%, 90%, or 95%).

At block 2604, a first compound including one or more nucleotides may be hybridized to the first portion of the first strand of a nucleic acid molecule of the first plurality of nucleic acid molecules. The first compound may fill in the 5' end overhang and remove jagged end to form a blunt end. For example, the first compound may be the dashed line 2165 in fragment 2164 in FIG. 21B. The first compound is attached to a 3' end of the second strand to form an extended nucleic acid molecule. The extended nucleic acid molecule has an elongated second strand with a 3' end including the first compound. The first compound has a 3' end that does not contact the second strand. For example, in stage 2170 of FIG. 21B, the 3' end of the dashed line 2165 of fragment 2164 does not contact the original strand that it elongates. The first compound may include the first type of nucleotide that is methylated differently than in the second strand. For example, if the first type of nucleotide in the second strand is methylated, then the first type of nucleotide in the first compound is unmethylated. Conversely, if the first type of nucleotide in the second strand is unmethylated, then the first type of nucleotide in the first compound is methylated. Each first type of nucleotide in the first compound may have an opposite methylation status as each of the first type of nucleotide in the second strand. Block 2604 may be repeated for each nucleic acid molecule of the first plurality of nucleic acid molecules.

The biological sample may include the second plurality of nucleic acid molecules during hybridizing. For example, no enzyme configured to remove the first portion of a nucleic acid molecule of the second plurality of nucleic acid molecules may be added to the biological sample. For instance, no exonuclease is added to the biological sample. The biological sample may not have the overhanging 3' ends of the second plurality of nucleic acid molecules trimmed to form blunt ended nucleic acid molecules. The second plurality of nucleic acid molecules may maintain the 3' overhang rather than having the 3' protruding end trimmed, similar to fragment 2108 in FIG. 21B.

In some embodiments, process 2600 may include phosphorylating the plurality of extended nucleic acid molecules. Process 2600 may also include phosphorylating the second plurality of nucleic acid molecules. For example, the 5' ends may be phosphorylated as in stage 2180 of FIG. 21B. Adapters may be added to the extended nucleic acid molecules. The second plurality of nucleic acid molecules may not have adapters added.

At block 2606, either the first type of nucleotide in the first compound or the first type of nucleotide in the second strand may be converted to a second type of nucleotide. The second type of nucleotide may be different from the first type of nucleotide. The conversion may be by bisulfite treatment. For example, the second type of nucleotide may be uracil, while the first type of nucleotide is cytosine. The cytosines, specifically unmethylated cytosines, may be converted to uracils by bisulfite treatment. The conversion may occur in the biological sample, and the biological sample may include the second plurality of nucleic acid molecules during conversion.

In some embodiments, the first type of nucleotide in the second strand may be converted. The method may then also include converting the first type of nucleotide in the second plurality of nucleic acid molecules. For example, second plurality of nucleotides may include uracils resulting from converting unmethylated cytosines.

At block 2608, a first methylation status may be determined for each of one or more sites corresponding to the first type of nucleotide in the first compound. The methylation status may be determined by determining the identity of nucleotides of the second type of nucleotide. For example, the first type of nucleotide in the first compound may be converted to the second type of nucleotide. The second type of nucleotide may be different from the first type of nucleotide. For example, uracils may be identified in the first compound, which means that the uracils were unmethylated cytosines before bisulfite treatment in block 2608 and the first methylation status is unmethylated. The identity of the nucleotides may be determined by any suitable sequencing technique, including those described herein.

As another example, if the first type of nucleotide in the second strand is converted to the second type of nucleotide, then the nucleotides in the first compound may be determined to be cytosines, which means that the first compound included methylated cytosines. The first methylation status is then methylated. Block 2608 may be repeated for each nucleic acid molecule of the first plurality of nucleic acid molecules.

In some embodiments, a methylation level using the first methylation statuses may be calculated. The methylation level may be a percentage, fraction, or number of sites that are methylated (or unmethylated) in the first plurality of nucleic acid molecules.

In some embodiments, a jagged index value using the methylation level may be determined. The jagged index value may provide a collective measure of the length of a strand that is not hybridized to another strand in the first plurality of nucleic acid molecules. The jagged index value may include JI-U, JI-M, or any index value described herein. The jagged index value may be for a certain fragment size.

In some embodiments, process 2600 may include determining the length of each first compound of the first plurality of nucleic acid molecules using the plurality of first methylation statuses. The length may be determined based on the amount of methylation. In some embodiments, the exact length may be determined based on consecutive sites of the same type showing different methylation statuses (e.g., using CC nucleotides to measure length in FIGS. 24A and 24B). The first type of nucleotide would be adjacent to the second type of nucleotide.

Although FIG. 26 shows example blocks of process 2600, in some implementations, process 2600 may include additional blocks, fewer blocks, different blocks, or differently arranged blocks than those depicted in FIG. 26. Additionally, or alternatively, two or more of the blocks of process 2600 may be performed in parallel.

IX. Periodicity Pattern of Jagged End Length in Urinary CFDNA

Cell-free DNA in urine shows a periodic behavior in frequency of jagged end lengths. The periodicity of cell-free DNA fragments in urine may help classify a level of condition of a subject. The condition may include cancer, e.g., kidney cancer.

Figure 27:
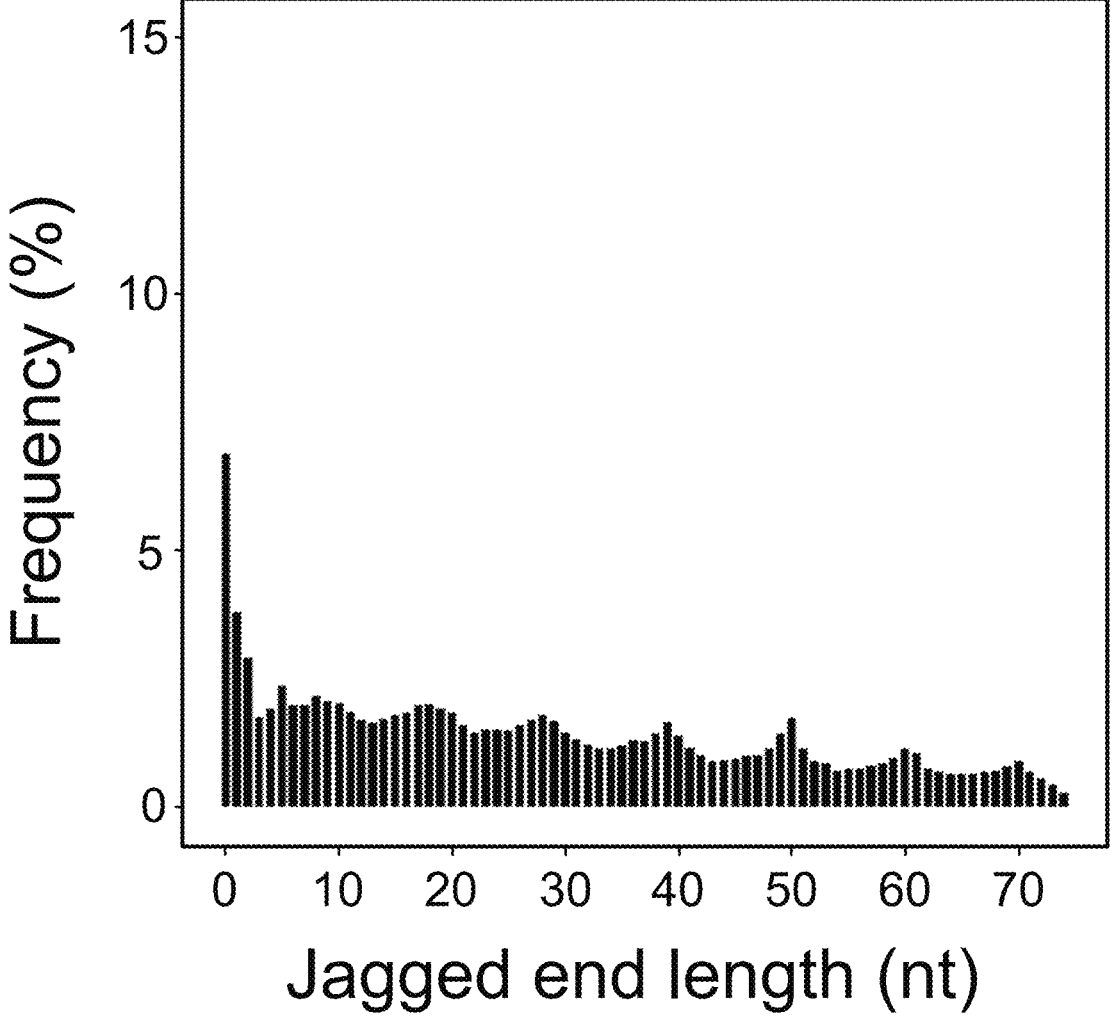
FIG. 27 shows a graph of the distribution of jagged end lengths deduced by using CC-tag technique in urine according to embodiments of the present invention.

FIG. 27 shows a graph of the distribution of jagged end lengths deduced by using CC-tag technique, described in section VIII.B, in urine. The x-axis shows the jagged end length in nucleotides. The y-axis shows the frequency (%) of the jagged end length size from 0 to 74 nt. The CC-tag technique is described above with FIGS. 24A and 24B.

FIG. 27 shows that, generally, when the jagged ends become longer, the relative frequency slowly decreases. For example, there are fewer fragments with a jagged end of 40 nt than 10 nt. On top of this gradual decrease, the jagged end lengths of urinary cfDNA showed a ~10 nt periodicity pattern, which was not seen for jagged ends in plasma DNA. By taking a more detailed look at the periodicity pattern, the amplitude of jagged end periodicity attracted our attention since it varied among different individuals. To analyze the amplitude of jagged end periodicity, we calculated the strength of the wave (e.g., for a total of seven peaks) by a mathematical approach shown in the following equation:

$$\text{Jagged end length periodicity index} = \left( \sum_{i=1}^{n=7} \frac{2p - vl - vr}{2p + vl + vr} \right) \Big/ 7$$

Where the p is the frequency of a particular peak, and vl (vr) is the frequency of the relative left (right) valley. The jagged end length periodicity index provides a measure of the difference between peaks and valleys. Other indices that quantify the differences between peaks and valleys may also be used.

A higher jagged end length periodicity index indicates a stronger 10 nt periodicity pattern of the distribution of jagged end length. We analyze further to see if the jagged end length periodicity index might be affected by the length of the fragments.

Figure 28:
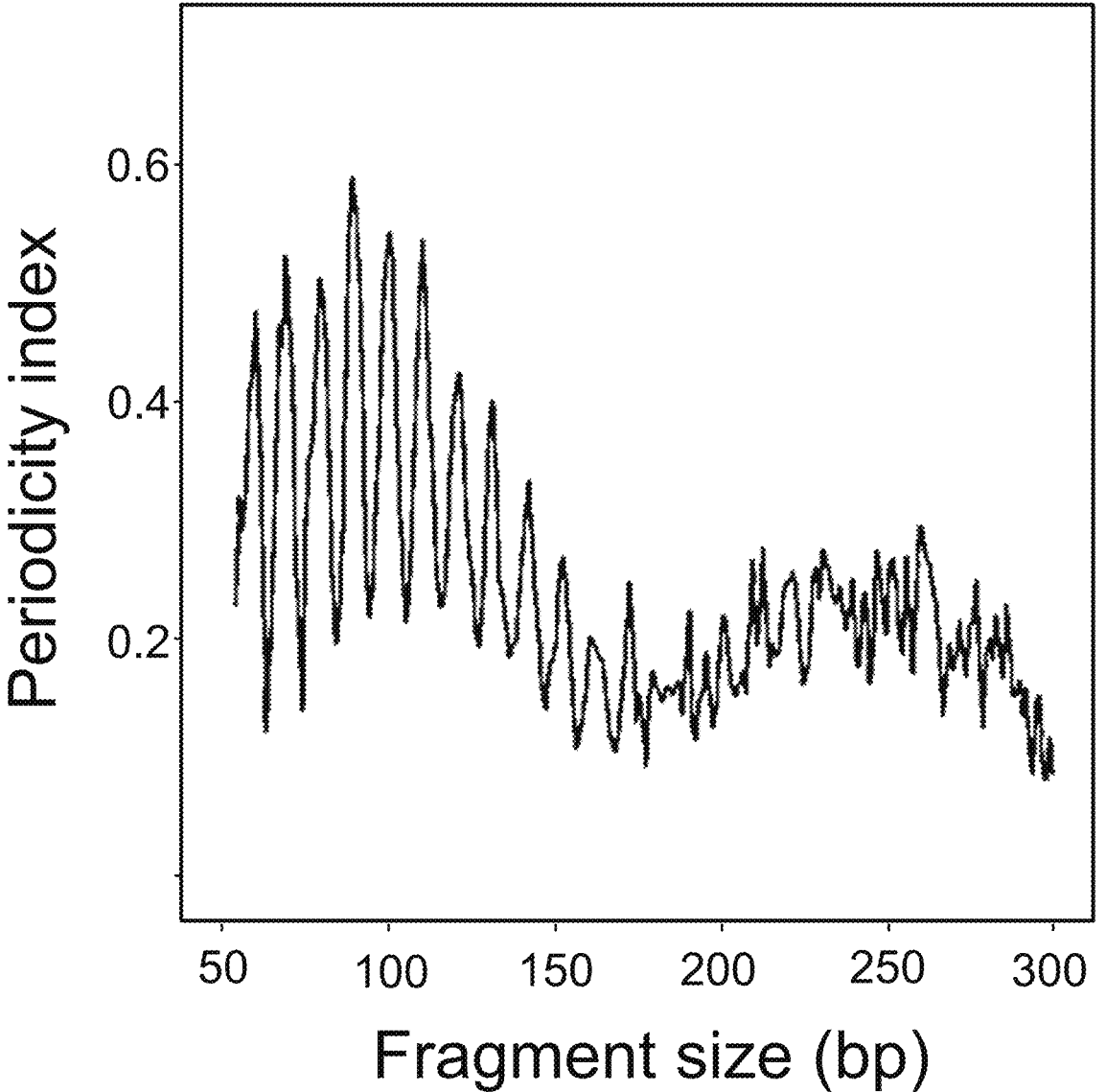
FIG. 28 shows a graph of the periodicity index of jagged end lengths across different fragment sizes according to embodiments of the present invention.

FIG. 28 shows a graph of periodicity index across different fragment sizes. The x-axis shows the fragment size in base pairs. The y-axis shows the jagged end length periodicity index. As shown in FIG. 28, the periodicity index of jagged end length revealed a 10-nt periodicity pattern across different fragment sizes when the fragment length was less than 170 bp. For example, we observed a number of peaks of periodicity index of jagged end length at 90 bp, 100 bp, 111 bp, 121 bp, 132 bp, and 142, and a number of troughs of periodicity index of jagged end length at 85 bp, 95 bp, 106 bp, 116 bp, 127 bp, 137 bp and 148 bp.

A. Jagged End Length Periodicity Index for Determining Renal Cell Cancer

The jagged end length periodicity index may be used to differentiate between subjects with renal cell cancer (RCC) and healthy control subjects. The jagged end length periodicity index may be a more effective biomarker than using jagged end values.

Figure 29A:
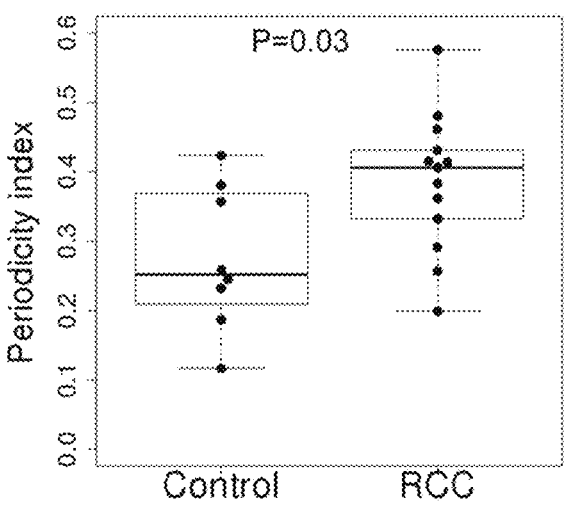
FIGS. 29A, 29B, and 29C show results from using periodicity index and average jagged end length in distinguishing control subjects from subjects with renal cell cancer (RCC) according to embodiments of the present invention.

FIG. 29A shows a graph of jagged end length periodicity index for control subjects and for subjects with RCC. The x-axis shows control subjects and subjects with RCC (i.e., kidney cancer). The y-axis shows the jagged end length periodicity index. As shown in FIG. 29A, kidney cancer urine samples were associated with a higher jagged end length periodicity index value. Jagged end length periodicity index values of RCC subjects (median, 0.41; range, 0.21-0.58) were found to be significantly higher than healthy control subjects (median, 0.25; range, 0.12-0.42).

Figure 29B:
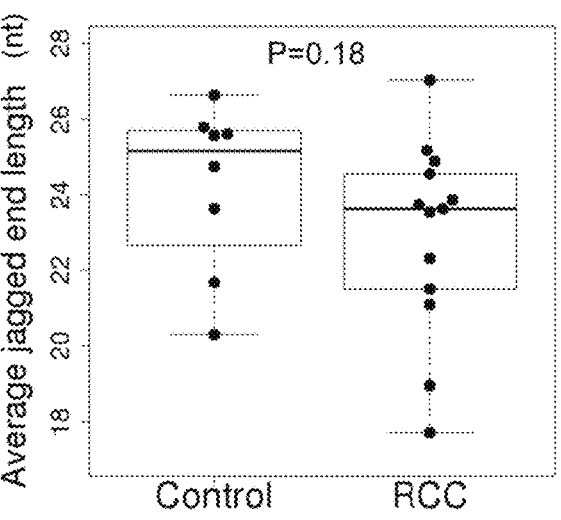

FIG. 29B shows a graph of average jagged end length for control subjects and for subjects with RCC. The x-axis shows control subjects and subjects with RCC (i.e., kidney cancer). The y-axis shows the average jagged end length (nt). The graph shows that there is not a statistically significant difference for average jagged end length between control subjects and RCC subjects. Control subjects and RCC subjects also did not show a statistically significant different with JI-M.

Figure 29C:
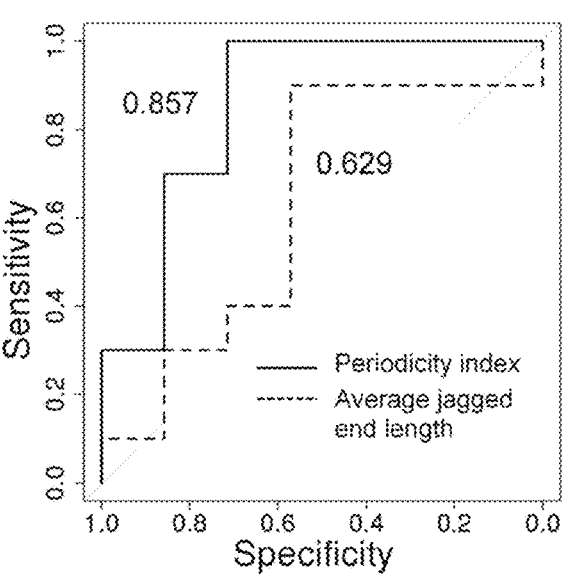

FIG. 29C shows ROC curves for using periodicity index and average jagged end length to differentiate between control subjects and subjects with RCC. The area under the curve (AUC) for using the periodicity index is 0.857. By contrast, the AUC for using average jagged end length was 0.629, showing that average jagged end length would not be effective in differentiating between healthy control subjects and those with RCC. Surprisingly, jagged end length periodicity index is a signature that enables discrimination between kidney cancer and non-cancer patients in urine samples.

B. The Effects of Heparin Treatment on Jagged End Length Periodicity in Urinary cfDNA The peculiar periodicity patterns appeared in urinary jagged end length motivated us to further investigate the mechanism underlying the production of jagged ends.

It is unknown as to whether the 10-bp periodicities of jagged length distribution would be related to nucleosomal conformations. It was reported that the 10 nt periodicity cleavage pattern of the DNA fragment size was likely caused by digestion of DNase I, which prefers single cut on double-strand DNA, and at the same time, heavily depended on histone-DNA binding structure (Suck, 1994). A previous study also found that heparin could disrupt chromatin structure by relaxing histone binding and thus increase the DNA accessibility (Villeponteau, 1992). Therefore, this altered nucleosome conformation displayed a higher sensitivity to digestion by one of the major nucleases, DNase I (Brotherton et al., 1989). Based on these studies, we then performed a set of heparin treatment experiments aimed at understanding whether nucleosome structure might involve the generation of 10 nt periodicity pattern of jagged end length in urinary cfDNA.

Figure 30:
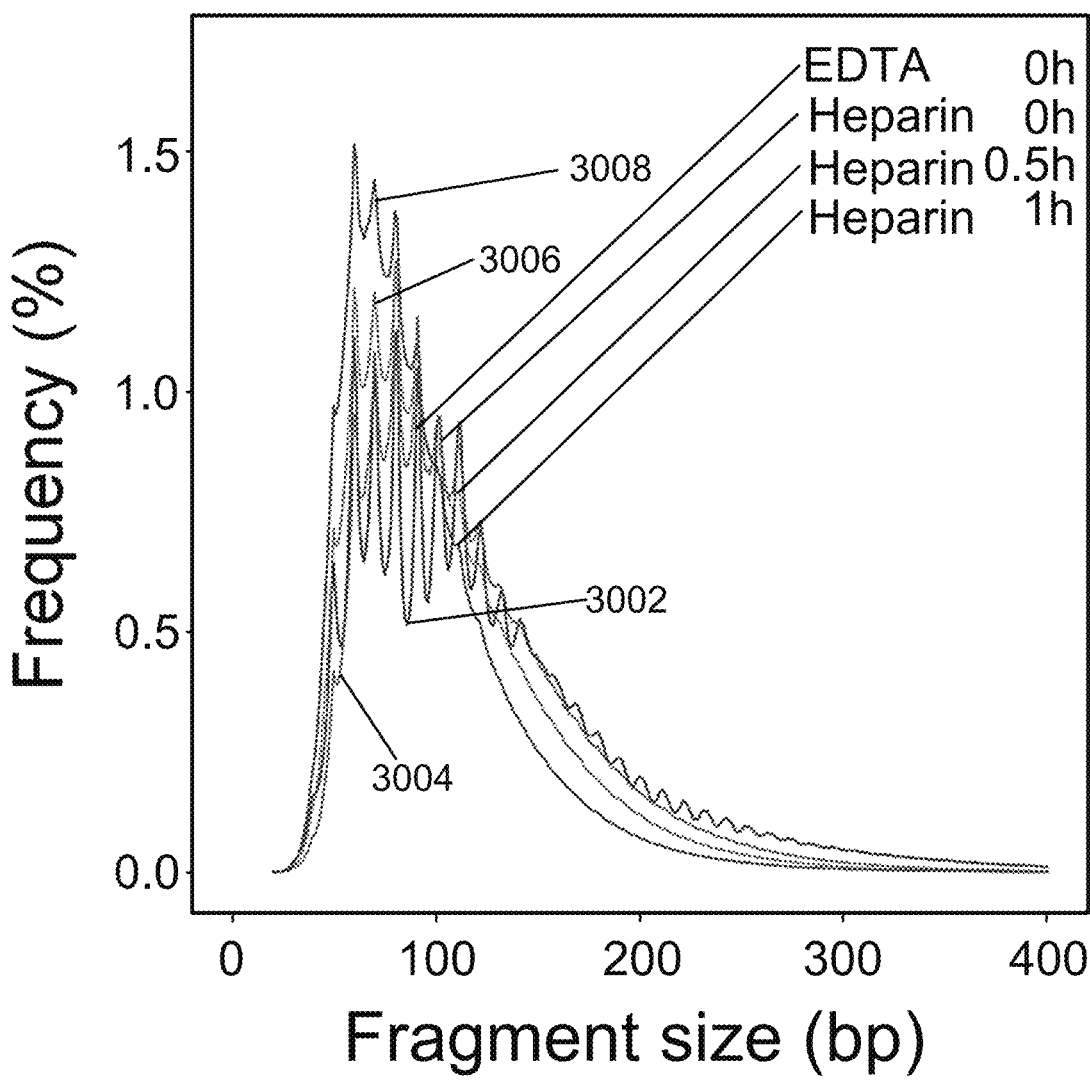
FIG. 30 shows a size profile of urinary cfDNA with heparin incubation treatment according to embodiments of the present invention.

FIG. 30 shows a size profile of urinary cfDNA with heparin incubation treatment. The x-axis shows the fragment size (bp). The y-axis shows the frequency (%). The different lines show different treatments. Lines 3002, 3004, 3006, and 3008 represent EDTA 0 h, heparin 0 h, heparin 0.5 h, and heparin 1 h treatment, respectively. The time represents the duration of in vitro incubation at room temperature. The treatment was followed by Jag-seq II. Treatment with EDTA is not expected to change jagged end length periodicity and serves as a control for comparison to treatments with heparin.

Compared with the EDTA 0 h treatment (line 3002), the amplitude of the 10 nt jagged end length periodicity was slightly weaker than when treated by heparin for 0 h (line 3004). Interestingly, as the incubation time of heparin increases, the periodicity started to gradually disappear. Notably, treatment with heparin for 1 h (line 3008) resulted in a loss of mostly all the 10 bp jagged end length periodicity patterns in urinary cfDNA due to the increasing disruption of chromatin structures.

Figure 31:
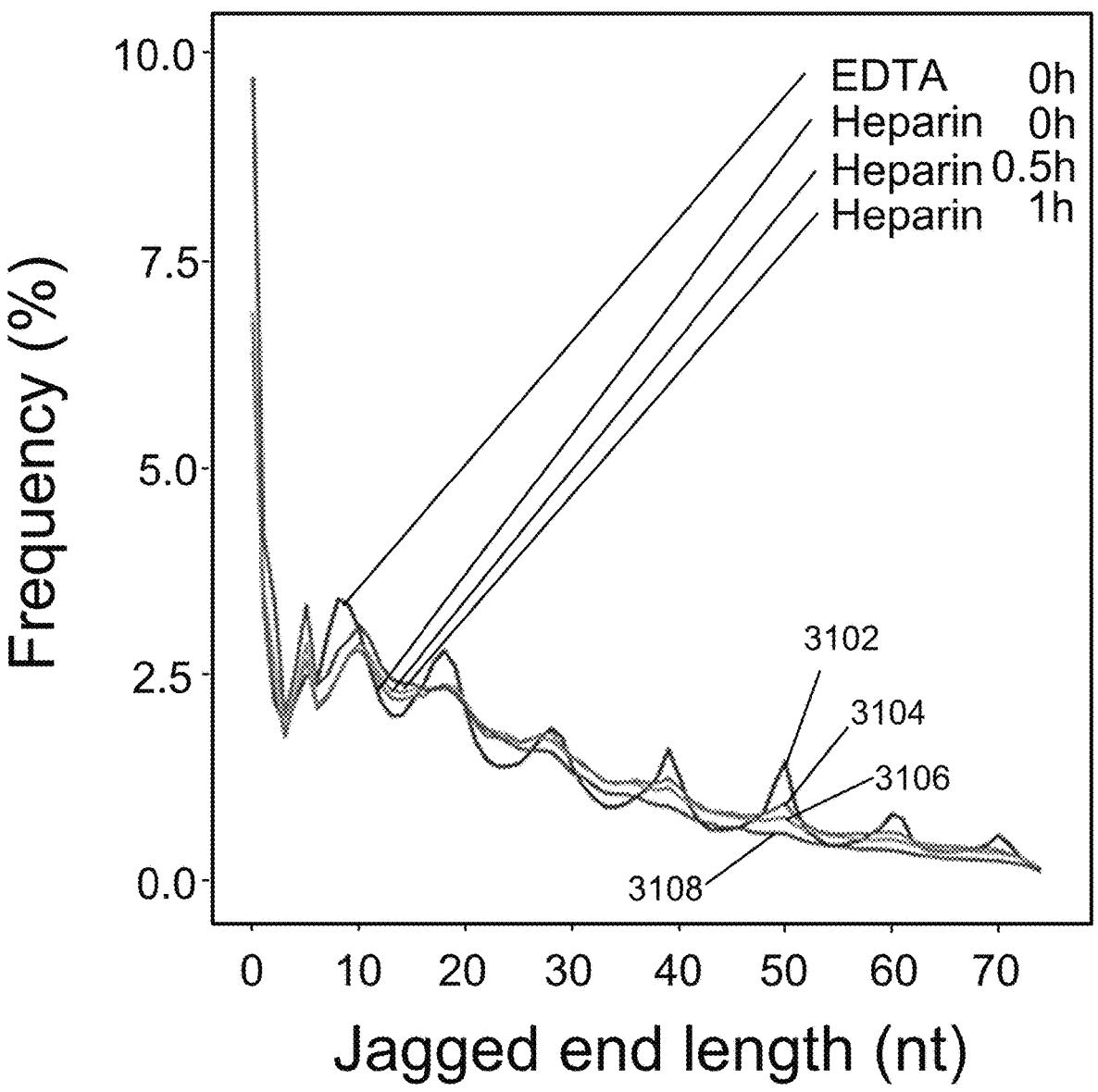
FIG. 31 shows jagged end length distribution in urinary cfDNA with heparin incubation treatment according to embodiments of the present invention.

FIG. 31 shows jagged end length distribution in urinary cfDNA with heparin incubation treatment. The x-axis shows the jagged end length (nt). The y-axis shows the frequency (%). Lines 3102, 3104, 3106, and 3108 represent EDTA 0 h, heparin 0 h, heparin 0.5 h, and heparin 1 h treatment, respectively. The underlying data for FIG. 31 is the same as for FIG. 30.

We explored whether heparin treatment affects the generation and distribution of urinary jagged ends through changing chromatin structure. As shown in FIG. 31, the 10 nt jagged end length periodicity pattern was remarkably weaker when the urine samples were treated with heparin for 0 h. As the heparin incubation time reached 1 h, the periodicity pattern nearly disappeared. FIG. 31 shows that increased heparin treatment time appears to decrease periodicity.

Figures 32A, 32B, 32C:
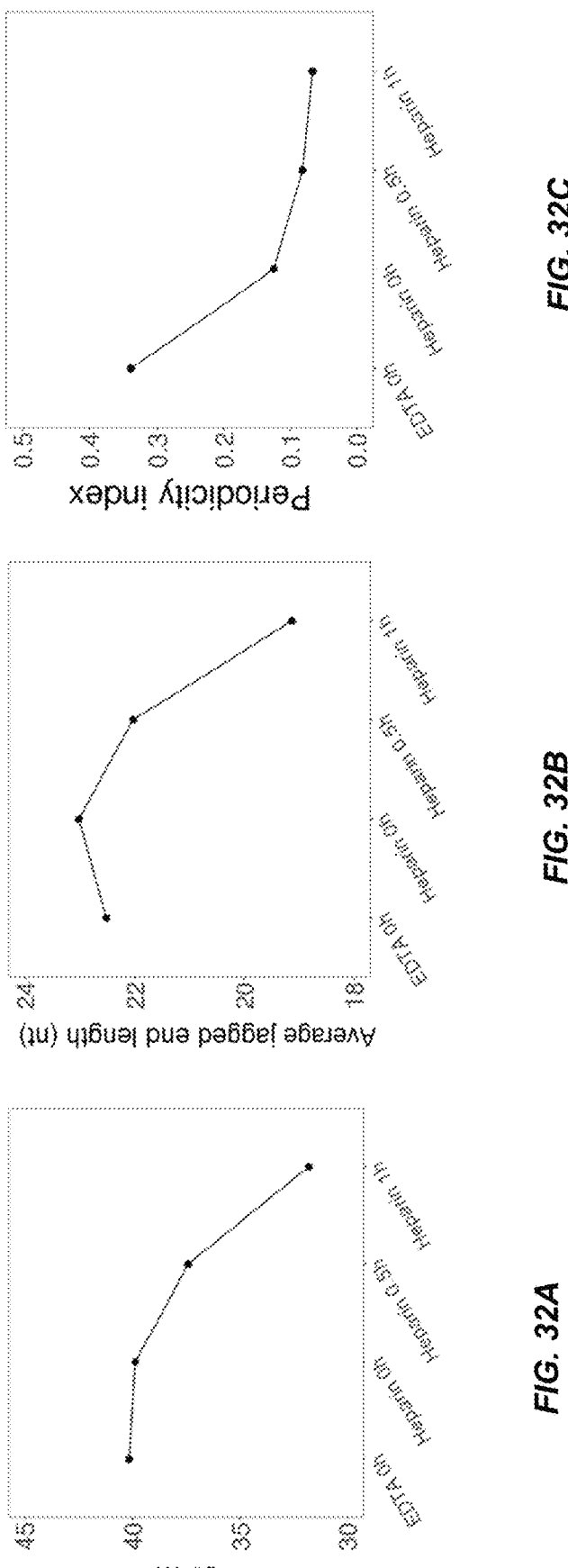
FIGS. 32A, 32B, and 32C show analysis of JI-M, average jagged end length, and periodicity index for different EDTA and heparin treatment in urine according to embodiments of the present invention.

FIGS. 32A, 32B, and 32C show analysis of JI-M, average jagged end length, and jagged end length periodicity index for different time periods of EDTA and heparin incubation. The underlying data in FIGS. 32A-32C are the same as in FIGS. 30 and 31. In FIGS. 32A-32C, the x-axis shows the different treatments (EDTA or heparin for different incubation times).

In FIG. 32A, the y-axis is the JI-M index. In FIG. 32B, the y-axis is the average jagged end length (nt). In FIGS. 32A and 32B, we found the value of JI-M and the average jagged end length did not differ significantly between EDTA 0 h and heparin 0 h treatment. Then, with prolonged periods (0.5 hour or 1 hour) of heparin incubation, JI-M and average jagged end length gradually decreased.

FIG. 32C shows jagged end length periodicity index on the y-axis. FIG. 32C shows a large reduction in periodicity index with heparin 0 h treatment compared to EDTA 0 h treatment. The longer heparin treatment times resulted in smaller reductions in jagged end length periodicity index.

Taking FIGS. 32A-32C together, these results strongly suggested that the 10 nt periodicity pattern of jagged end length is closely related with the histone and urinary cfDNA binding structures, combined the activity level of DNase I.

C. Example Methods

FIG. 33 is a flowchart of an example process 3300 associated with analyzing a biological sample to classify a level of a condition using periodicity related to jagged end lengths of cell-free DNA fragments. In some implementations, one or more process blocks of FIG. 33 may be performed by a system (e.g., system 3400 in FIG. 34). In some implementations, one or more process blocks of FIG. 33 may be performed by another device or a group of devices separate from or including the system. Additionally, or alternatively, one or more process blocks of FIG. 33 may be performed by one or more components of system 3400, such as processor 3450, memory 3435, external memory 3440, storage device 3445, sample holder 3410, detector 3420, and/or logic system 3430.

The biological sample may include a plurality of nucleic acid molecules. In some embodiments, the biological sample may be urine, serum, saliva, or any sample described herein other than plasma. The plurality of nucleic acid molecules may be cell-free. Each nucleic acid molecule of the plurality of nucleic acid molecules is double-stranded with a first strand having a first portion and a second strand. The first portion of the first strand of at least some of the plurality of nucleic acid molecules has no complementary portion from the second strand, is not hybridized to the second strand, and is at a first end of the first strand. The plurality of nucleic acid molecules have a size in a range of 50 to 170 nt, 50 to 100 nt, 100 to 140 nt, 140 to 170 nt, 170 to 200 nt, 200 to 240 nt, or greater than 240 nt. The plurality of nucleic acid molecules may be a statistically significant number for analysis, which may be any number for cell-free nucleic acid molecules described herein.

At block 3302, a characteristic of each nucleic acid molecule of the plurality of nucleic acid molecules is measured. The characteristic correlates to (e.g., is proportional to) a length of the first strand that overhangs or is not hybridized to the second strand. The characteristic may be length. In some embodiments, the characteristic may be a methylation level. The characteristic may be measured for the first strand and/or the second strand for each nucleic acid molecule.

At block 3304, a histogram may be created. The histogram may be created by measuring an amount of nucleic acid molecules having each of a plurality of values of the measured characteristic. The histogram may plot the amount (e.g., frequency) against different jagged end lengths. Examples of histograms include FIG. 27 or FIG. 31. A histogram may not be presented as a graph. In some embodiments, the histogram may be in a tabular form.

At block 3306, a plurality of peak amounts and a plurality of local minimum amounts may be identified using the histogram. The peak amounts may be local maximum amounts. The peak amounts and the local minimum amounts may be determined visually from the histogram. In some embodiments, the peak amounts and the local minimum amounts may be determined mathematically. For example, a peak amount or a local minimum amount may be determined when the derivative of the histogram is zero. The peak amounts may be when the second derivative is negative. The minimum amounts may be when the second derivative is positive.

The plurality of peak amounts may appear at periodic intervals of the measured characteristic. For example, the peak amounts may appear at the top of a wave-like pattern. The periodic interval of the measured characteristic may correspond to a length of 9 to 11 nt, 5 to 9 nt, 12 to 15 nt, 15 to 20 nt, 20 to 25 nt, or more. The local minimum amounts may appear at periodic intervals of the measured characteristic. For example, the plurality of local minimum amounts may appear at the bottom of a wave-like pattern. The plurality of peak amounts may number 2, 3, 4, 5, 6, 7, 8, 9, 10, or more peaks. The plurality of local minimum amounts may number 2, 3, 4, 5, 6, 7, 8, 9, 10, or more local minima. In some embodiments, the plurality of peak amounts and the plurality of local minimum amounts may not include all peak amounts and all local minimum amounts present in the histogram. For example, peak amounts and local minimum amounts at short (e.g., less than 5 nt) jagged end lengths or long jagged end lengths may be excluded.

At block 3308, a jagged index value may be determined. The jagged index value may be determined using the plurality of peak amounts and the plurality of local minimum amounts. The jagged index value may provide a collective measure of the peak amounts relative to the local minimum amounts. In some embodiments, the jagged index value may be determined using only the plurality of peak amounts or only the plurality of local minimum amounts. For example, the jagged index value may be determined using a frequency, period, or amplitude of the plurality of peak amounts. In some examples, the jagged index value may be determined using a frequency, period, or amplitude of the plurality of local minimum amounts. An average or median frequency, period, or amplitude may be used.

The jagged index value may be determined using amplitudes of a plurality of local minimum amounts. The jagged index value may be determined using a comparison of each peak amount of the plurality of peak amounts with at least one adjacent local minimum amount. The comparison may include a difference, a sum, a ratio, or a product. The jagged index value may be the periodicity index described above.

The jagged index value may be compared to a reference value. The reference value may be determined using one or more reference samples of subjects that have the condition, or the reference value may be determined using one or more reference samples of subjects that do not have the condition. The reference value may be a threshold value that indicates a statistically significant difference from an expected value for subjects with the condition or for subjects without the condition. For example, the reference value may be set at 1, 2, or 3 standard deviations from an average jagged index value for the reference subjects. In some embodiments, the reference value may be a jagged index value from the same subject at an earlier time (e.g., before cancer treatment or from a healthy baseline condition).

At block 3310, a level of a condition of the individual may be determined using the jagged index value. The determination may be based on comparing the jagged index value to the reference value. The condition may be a cancer. For example, the condition may be kidney cancer. The classification may be that cancer exists when the jagged index value exceeds the reference value. The classification may be any classification described herein. The classification may be a severity of cancer, which may include a stage of cancer. The classification may be that the cancer is becoming more or less severe.

Process 3300 may further include treating the condition, which may be any treatment described herein, including with method 600.

Although FIG. 33 shows example blocks of process 3300, in some implementations, process 3300 may include additional blocks, fewer blocks, different blocks, or differently arranged blocks than those depicted in FIG. 33. Additionally, or alternatively, two or more of the blocks of process 3300 may be performed in parallel.

X. Example Systems

Figure 34:
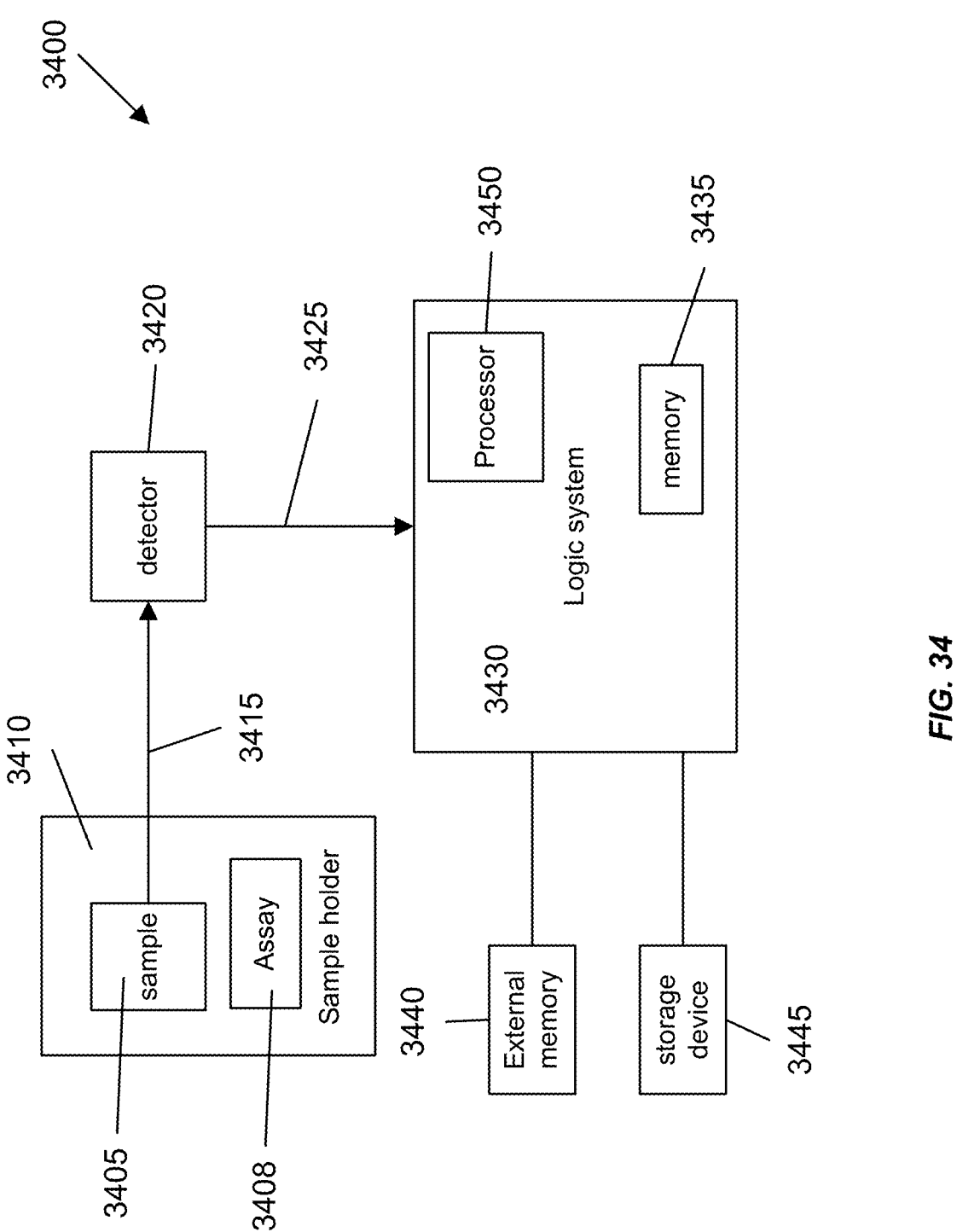
FIG. 34 illustrates a measurement system according to embodiments of the present invention.

FIG. 34 illustrates a measurement system 3400 according to an embodiment of the present invention. The system as shown includes a sample 3405, such as cell-free DNA molecules within a sample holder 3410, where sample 3405 can be contacted with an assay 3408 to provide a signal of a physical characteristic 3415. An example of a sample holder can be a flow cell that includes probes and/or primers of an assay or a tube through which a droplet moves (with the droplet including the assay). Physical characteristic 3415 (e.g., a fluorescence intensity, a voltage, or a current), from the sample is detected by detector 3420. Detector 3420 can take a measurement at intervals (e.g., periodic intervals) to obtain data points that make up a data signal. In one embodiment, an analog-to-digital converter converts an analog signal from the detector into digital form at a plurality of times. Sample holder 3410 and detector 3420 can form an assay device, e.g., a sequencing device that performs sequencing according to embodiments described herein. A data signal 3425 is sent from detector 3420 to logic system 3430. Data signal 3425 may be stored in a local memory 3435, an external memory 3440, or a storage device 3445.

Logic system 3430 may be, or may include, a computer system, ASIC, microprocessor, etc. It may also include or be coupled with a display (e.g., monitor, LED display, etc.) and a user input device (e.g., mouse, keyboard, buttons, etc.). Logic system 3430 and the other components may be part of a stand-alone or network connected computer system, or they may be directly attached to or incorporated in a device (e.g., a sequencing device) that includes detector 3420 and/or sample holder 3410. Logic system 3430 may also include software that executes in a processor 3450. Logic system 3430 may include a computer readable medium storing instructions for controlling system 3400 to perform any of the methods described herein. For example, logic system 3430 can provide commands to a system that includes sample holder 3410 such that sequencing or other physical operations are performed. Such physical operations can be performed in a particular order, e.g., with reagents being added and removed in a particular order. Such physical operations may be performed by a robotics system, e.g., including a robotic arm, as may be used to obtain a sample and perform an assay.

Figure 35:
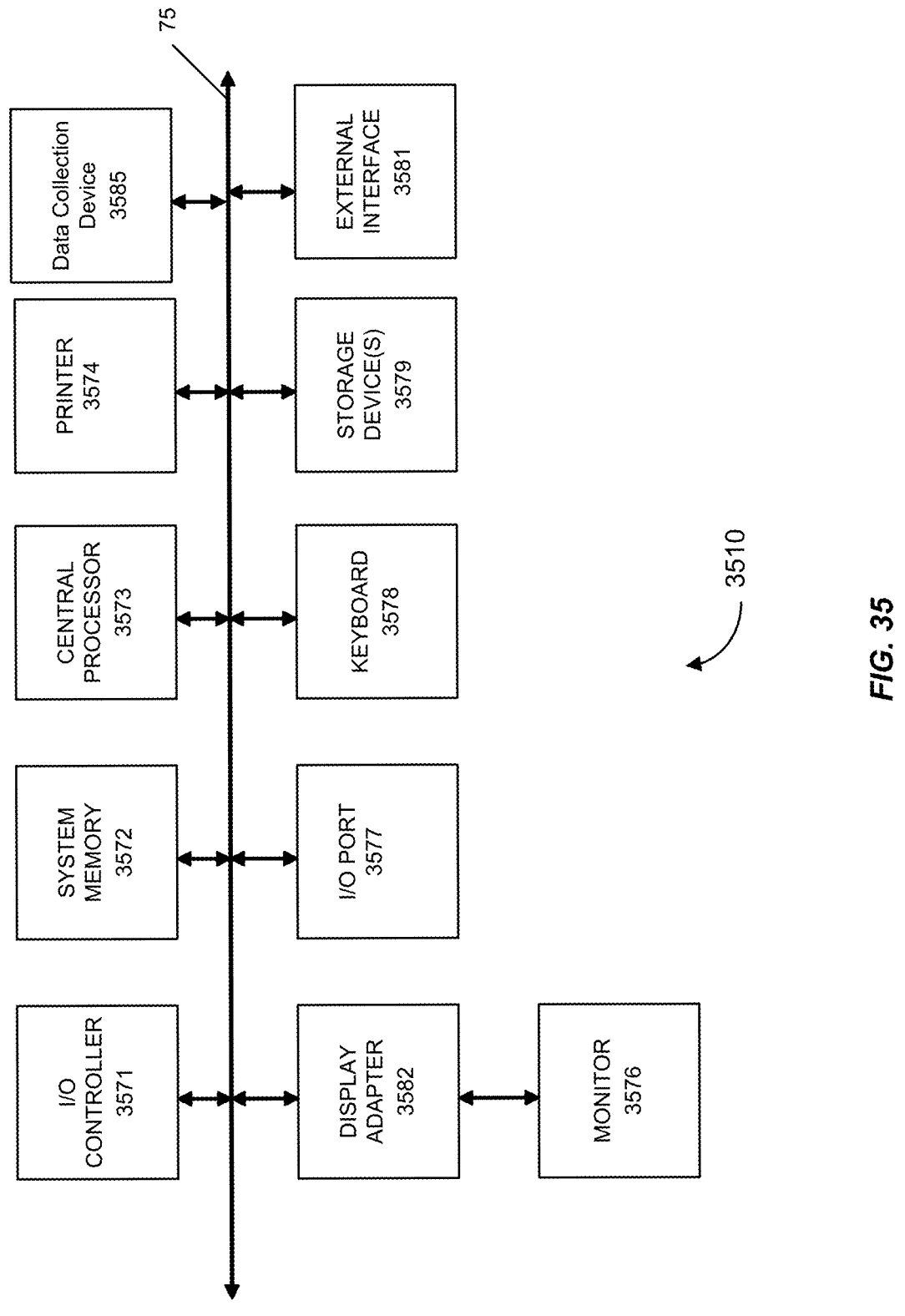
FIG. 35 shows a block diagram of an example computer system usable with systems and methods according to embodiments of the present invention.

Any of the computer systems mentioned herein may utilize any suitable number of subsystems. Examples of such subsystems are shown in FIG. 35 in computer system 10. In some embodiments, a computer system includes a single computer apparatus, where the subsystems can be the components of the computer apparatus. In other embodiments, a computer system can include multiple computer apparatuses, each being a subsystem, with internal components. A computer system can include desktop and laptop computers, tablets, mobile phones and other mobile devices.

The subsystems shown in FIG. 35 are interconnected via a system bus 3575. Additional subsystems such as a printer 3574, keyboard 3578, storage device(s) 3579, monitor 3576 (e.g., a display screen, such as an LED), which is coupled to display adapter 3582, and others are shown. Peripherals and input/output (I/O) devices, which couple to I/O controller 3571, can be connected to the computer system by any number of means known in the art such as input/output (I/O) port 3577 (e.g., USB, FireWire®). For example, I/O port 3577 or external interface 3581 (e.g. Ethernet, Wi-Fi, etc.) can be used to connect computer system 3510 to a wide area network such as the Internet, a mouse input device, or a scanner. The interconnection via system bus 3575 allows the central processor 3573 to communicate with each subsystem and to control the execution of a plurality of instructions from system memory 3572 or the storage device(s) 3579 (e.g., a fixed disk, such as a hard drive, or optical disk), as well as the exchange of information between subsystems. The system memory 3572 and/or the storage device(s) 3579 may embody a computer readable medium. Another subsystem is a data collection device 3585, such as a camera, microphone, accelerometer, and the like. Any of the data mentioned herein can be output from one component to another component and can be output to the user.

A computer system can include a plurality of the same components or subsystems, e.g., connected together by external interface 3581, by an internal interface, or via removable storage devices that can be connected and removed from one component to another component. In some embodiments, computer systems, subsystem, or apparatuses can communicate over a network. In such instances, one computer can be considered a client and another computer a server, where each can be part of a same computer system. A client and a server can each include multiple systems, subsystems, or components.

Aspects of embodiments can be implemented in the form of control logic using hardware circuitry (e.g. an application specific integrated circuit or field programmable gate array) and/or using computer software with a generally programmable processor in a modular or integrated manner. As used herein, a processor can include a single-core processor, multi-core processor on a same integrated chip, or multiple processing units on a single circuit board or networked, as well as dedicated hardware. Based on the disclosure and teachings provided herein, a person of ordinary skill in the art will know and appreciate other ways and/or methods to implement embodiments of the present invention using hardware and a combination of hardware and software.

Any of the software components or functions described in this application may be implemented as software code to be executed by a processor using any suitable computer language such as, for example, Java, C, C++, C#, Objective-C, Swift, or scripting language such as Perl or Python using, for example, conventional or object-oriented techniques. The software code may be stored as a series of instructions or commands on a computer readable medium for storage and/or transmission. A suitable non-transitory computer readable medium can include random access memory (RAM), a read only memory (ROM), a magnetic medium such as a hard-drive or a floppy disk, or an optical medium such as a compact disk (CD) or DVD (digital versatile disk) or Blu-ray disk, flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium may be created using a data signal encoded with such programs. Computer readable media encoded with the program code may be packaged with a compatible device or provided separately from other devices (e.g., via Internet download). Any such computer readable medium may reside on or within a single computer product (e.g. a hard drive, a CD, or an entire computer system), and may be present on or within different computer products within a system or network. A computer system may include a monitor, printer, or other suitable display for providing any of the results mentioned herein to a user.

Any of the methods described herein may be totally or partially performed with a computer system including one or more processors, which can be configured to perform the steps. Any operations performed with a processor (e.g., aligning, determining, comparing, computing, calculating) may be performed in real-time. Thus, embodiments can be directed to computer systems configured to perform the steps of any of the methods described herein, potentially with different components performing a respective step or a respective group of steps. Although presented as numbered steps, steps of methods herein can be performed at a same time or at different times or in a different order. Additionally, portions of these steps may be used with portions of other steps from other methods. Also, all or portions of a step may be optional. Additionally, any of the steps of any of the methods can be performed with modules, units, circuits, or other means of a system for performing these steps.

The specific details of particular embodiments may be combined in any suitable manner without departing from the spirit and scope of embodiments of the invention. However, other embodiments of the invention may be directed to specific embodiments relating to each individual aspect, or specific combinations of these individual aspects.

The above description of example embodiments of the present disclosure has been presented for the purposes of illustration and description. It is not intended to be exhaustive or to limit the disclosure to the precise form described, and many modifications and variations are possible in light of the teaching above.

A recitation of "a", "an" or "the" is intended to mean "one or more" unless specifically indicated to the contrary. The use of "or" is intended to mean an "inclusive or," and not an "exclusive or" unless specifically indicated to the contrary. Reference to a "first" component does not necessarily require that a second component be provided. Moreover, reference to a "first" or a "second" component does not limit the referenced component to a particular location unless expressly stated. The term "based on" is intended to mean "based at least in part on."

All patents, patent applications, publications, and descriptions mentioned herein are incorporated by reference in their entirety for all purposes. None is admitted to be prior art.

XI. References

Brotherton, T. W., Jagannadham, M. V., & Ginder, G. D. (1989). Heparin Binds to Intact Mononucleosomes and Induces a Novel Unfolded Structure. Biochemistry. https://doi.org/10.1021/bi00434a055

Jiang, P., Xie, T., Ding, S. C., Zhou, Z., Cheng, S. H., Chan, R. W. Y., Lee, W. S., Peng, W., Wong, J., Wong, V. W. S., Chan, H. L. Y., Chan, S. L., Poon, L. C. Y., Leung, T. Y., Chan, K. C. A., Chiu, R. W. K., & Lo, Y. M. D. (2020). Detection and characterization of jagged ends of double-stranded DNA in plasma. Genome Research, 30(8). https://doi.org/10.1101/gr.261396.120

Suck, D. (1994). DNA recognition by DNase I. In Journal of Molecular Recognition. https://doi.org/10.1002/jmr.300070203

Villeponteau, B. (1992). Heparin increases chromatin accessibility by binding the trypsin-sensitive basic residues in histones. Biochemical Journal. https://doi.org/10.1042/bj2880953

What is claimed is:

1. A method of analyzing a urine sample, the method comprising:

measuring a characteristic of each nucleic acid molecule of a cell-free plurality of nucleic acid molecules from the urine sample of an individual, the cell-free plurality of nucleic acid molecules comprising at least 10,000 cell-free nucleic acid molecules, wherein:

each nucleic acid molecule of the cell-free plurality of nucleic acid molecules is double-stranded with a first strand having a first portion and a second strand, the first portion of the first strand of at least some of the cell-free plurality of nucleic acid molecules overhangs the second strand, an extent of overhang varies among the cell-free plurality of nucleic acid molecules;

the characteristic correlates to a length of the first strand that overhangs the second strand, wherein:

the characteristic is the length of the first strand that overhangs the second strand, or the characteristic is a methylation status at one or more sites at end portions of the first strands, the second strands, or the first strands and the second strands of each of the cell-free plurality of nucleic acid molecules;

determining a jagged index value using the measured characteristics of the cell-free plurality of nucleic acid molecules, wherein the jagged index value provides a collective average measure that a strand overhangs another strand in the plurality of nucleic acid molecules, wherein the collective average measure is proportional to an average length that the first strands overhang the second strands in the plurality of nucleic acid molecules;

comparing the jagged index value to a reference value, wherein the reference value is determined using at least one of one or more reference samples of subjects that have a condition and one or more reference samples of subjects that do not have the condition; and determining a level of the condition of the individual using the comparison, wherein the level of the condition is whether the condition exists or a severity of the condition, and wherein the condition is bladder cancer or kidney cancer.

2. The method of claim 1, wherein the measuring comprises measuring a characteristic of a first strand, a second strand, or the first strand and the second strand for each nucleic acid molecule.

3. The method of claim 1, wherein the first portion is at a first end of the first strand, and the first end is a 5' end.

4. The method of claim 1, further comprising:

measuring sizes of nucleic acid molecules present in the urine sample, and filtering the nucleic acid molecules for molecules having sizes within a size range to obtain the cell-free plurality of nucleic acid molecules.

5. The method of claim 4, wherein the size specified range is 140 to 160 bp.

6. The method of claim 4, wherein:

the cell-free plurality of nucleic acid molecules is a first plurality of nucleic acid molecules, and the size range is a first size range, the method further comprising:

filtering the nucleic acid molecules for molecules having sizes with a second range to obtain a second plurality of nucleic acid molecules, and measuring the characteristic of a strand of each nucleic acid molecule of the second plurality of nucleic acid molecules, wherein determining the jagged index value comprises calculating a ratio using the measured characteristics of the first plurality of nucleic acid molecules and the measured characteristics of the second plurality of nucleic acid molecules.

7. The method of claim 1, wherein the characteristic is the methylation status at the one or more sites at end portions of the first strands, the second strands, or the first strands and the second strands of each of the cell-free plurality of nucleic acid molecules, and wherein the jagged index value is determined using a methylation level over the cell-free plurality of nucleic acid molecules at one or more sites of end portions of the first strands, the second strands, or the first strands and the second strands.

8. The method of claim 1, wherein the characteristic is the length of the first strand that overhangs the second strand.

9. The method of claim 1, further comprising:

analyzing nucleic acid molecules to produce reads, aligning the reads to a reference genome, and filtering the nucleic acid molecules for molecules having reads within a certain distance relative to a transcription start site to obtain the cell-free plurality of nucleic acid molecules.

10. The method of claim 1, further comprising:

analyzing nucleic acid molecules to produce reads, aligning the reads to a reference genome, and filtering the nucleic acid molecules for molecules having reads within a distance range relative to CTCF site or a DNASE1 hypersensitive site to obtain the cell-free plurality of nucleic acid molecules.

11. The method of claim 1, wherein the reference value is determined using one or more reference samples of subjects that have the condition.

12. The method of claim 1, wherein a machine learning model is used to perform the comparing of the jagged index value to the reference value and the determining of the level of the condition of the individual.

13. A method of analyzing a urine sample, the method comprising:

sequencing a cell-free plurality of nucleic acid molecules from the urine sample of an individual to produce sequence reads, wherein each nucleic acid molecule of the cell-free plurality of nucleic acid molecules is double-stranded with a first strand having a first portion and a second strand, and wherein the first portion of the first strand of at least some of the cell-free plurality of nucleic acid molecules overhangs the second strand;

aligning the sequence reads to a reference genome to determine genomic locations of the cell-free plurality of nucleic acid molecules;

filtering the cell-free plurality of nucleic acid molecules for nucleic acid molecules having a genomic location at a specified distance from a predetermined type of genomic site to obtain a set of nucleic acid molecules of the cell-free plurality of nucleic acid molecules, the set of cell-free nucleic acid molecules comprising at least 10,000 cell-free nucleic acid molecules, and wherein the type of genomic site is determined prior to aligning the sequence reads and wherein the predetermined type of genomic site is associated with a modification of a protein in chromatin at the genomic site or a protein interaction at the genomic site;

measuring a characteristic of each nucleic acid molecule of the set of nucleic acid molecules, wherein:

the characteristic correlates to a length of the first strand that overhangs the second strand, wherein:

the characteristic is the length of the first strand that overhangs the second strand, or the characteristic is a methylation status at one or more sites at end portions of the first strands, the second strands, or the first strands and the second strands of each of the cell-free plurality of nucleic acid molecules;

determining a jagged index value using the measured characteristics of the set of nucleic acid molecules, wherein the jagged index value provides a collective average measure that a strand overhangs another strand in the set of nucleic acid molecules, wherein the collective average measure is proportional to an average length that the first strands overhang the second strands in the set of nucleic acid molecules;

comparing the jagged index value to a reference value, wherein the reference value is determined using at least one of one or more reference samples of subjects that have a condition and one or more reference samples of subjects that do not have the condition; and determining a level of the condition of the individual using the jagged index value, wherein the level of the condition is whether the condition exists or a severity of the condition, and wherein the condition is bladder cancer or kidney cancer.

14. The method of claim 13, wherein the distance is a range.

15. The method of claim 13, wherein the distance is 0 nt.

16. The method of claim 13, wherein the genomic site is a CTCF binding site, a DNASE1 hypersensitive site (DHS), or a region with a histone modification.

17. The method of claim 16, wherein the genomic site is the region with the histone modification.

18. The method of claim 17, wherein the histone modification comprises H3K4me1, H3K4me3, H3K36me3, H3K27me2, H3K9Ac, H3K27Ac, H4K16Ac, H3K27me3, or H3K9me3.

19. The method of claim 7, wherein the jagged index value is further determined using a methylation level over one or more sites of a complementary portion hybridized to the first strand, the method further comprising hybridizing the complementary portion to the first strand.

20. The method of claim 1, wherein determining the level of the condition comprises determining the condition is present in the individual, the method further comprising treating the condition in the individual, wherein the treating includes one or more of chemotherapy, immunotherapy, radiation therapy, and/or surgery.

* * * * *